United States Patent [19]

Itoh et al.

[11] Patent Number: 5,350,843
[45] Date of Patent: Sep. 27, 1994

[54] HALOGENATED PHTHALOCYANINE COMPOUND, METHOD FOR PREPARING SAME

[75] Inventors: Hisato Itoh; Takahisa Oguchi; Shin Aihara; Kenichi Sugimoto, all of Yokohama, Japan

[73] Assignees: Mitsui Toatsu Chemicals, Incorporated, Tokyo; Yamamoto Chemicals, Incorporated, Yao, both of Japan

[21] Appl. No.: 877,174

[22] PCT Filed: Oct. 11, 1991

[86] PCT No.: PCT/JP91/01384

§ 371 Date: Jul. 6, 1992

§ 102(e) Date: Jul. 6, 1992

[87] PCT Pub. No.: WO92/07911

PCT Pub. Date: May 14, 1992

[30] Foreign Application Priority Data

Nov. 6, 1990 [JP] Japan .................. 2-298792

[51] Int. Cl.⁵ .............................. C07D 487/22
[52] U.S. Cl. ........................................ 540/138
[58] Field of Search ........................... 540/138

[56] References Cited

U.S. PATENT DOCUMENTS

| | | | |
|---|---|---|---|
| 2,214,469 | 8/1935 | Linstead et al. ............. | 540/138 |
| 4,948,884 | 8/1990 | Nonaka et al. .............. | 540/138 |
| 5,153,313 | 10/1992 | Kazmaier et al. ............ | 540/138 |

FOREIGN PATENT DOCUMENTS

| | | |
|---|---|---|
| 0272565 | 6/1988 | European Pat. Off. . |
| 0353394 | 2/1990 | European Pat. Off. . |
| 0373643 | 6/1990 | European Pat. Off. . |
| 0451718 | 10/1991 | European Pat. Off. . |
| 0462368 | 12/1991 | European Pat. Off. . |
| 2252386 | 6/1975 | France . |
| 50-85630 | 7/1975 | Japan . |
| 61-197280 | 9/1986 | Japan . |
| 2168372 | 6/1986 | United Kingdom . |

OTHER PUBLICATIONS

Cook et al., J. Chem. Soc., Perk Trans. I., 1988, pp. 2453–2458.

Chemical Abstracts, vol. 112, No. 10, 86672m (Mar. 1990), Bernstein P. A. et al. "Two–electron oxidation of cobalt phthalocyannes by thionyl chloride. Implications for lithium/thionyl chloride batteries." p. 626.

Cleavage of Alkyl 0-Hydroxphenyl Ethers, Robert G. Lange, Organic Chemicals Division, Nov. 27, 1961, pp. 2037–2039.

Chem. Ber., 2761 (1960), Walter Mayer, et al.

Structural Models of Cortin Compounds in the Naphthalene Series, JOC 6, 852 (1941), Louis Long, et al.

Chem. Ber., 76B, 900 (1943), Richard Kuhn, et al.

*Primary Examiner*—Mukund J. Shah
*Assistant Examiner*—P. K. Sripada
*Attorney, Agent, or Firm*—Oblon, Spivak, McClelland, Maier & Neustadt

[57] ABSTRACT

A method for preparing a mixture of the halogenated alkoxyphthalocyanines represented by the formula (8) which comprises the step of reacting alkoxyphthalocyanines represented by the formula (7) and a mixture thereof with a halogenating agent in a mixed solvent of an organic solvent and water.

(7)

(Abstract continued on next page.)

-continued
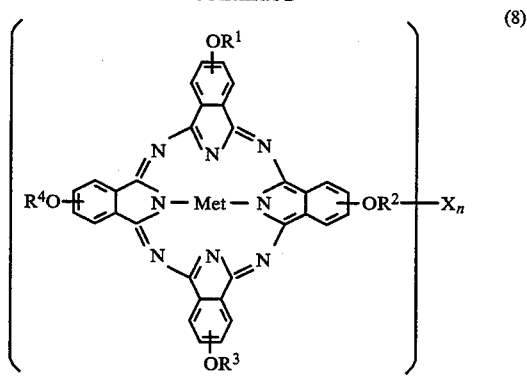
(8)
14 Claims, 9 Drawing Sheets

HPLC
SAMPLE: 2.0mg/ml (THF), 5 μ 1
COLUMN: YMC - PACK AQ - 312
(S - 5 120A ODS)
⌀ 6 mm x 150 mm x 2
MOBILE PHASE: THF: MeOH = 1:1
DEVICE: JASCO 880 - PU,
SHIMADZU SPD - 6AV
FLOW VELOCITY: 1.0 ml/min.
PRESSURE: 45kg/cm$^2$
TEMP.: ROOM TEMP.
DETECTOR: D2 320nm, ABS 0.08
CHART SPEED: 3.0 mm/min.

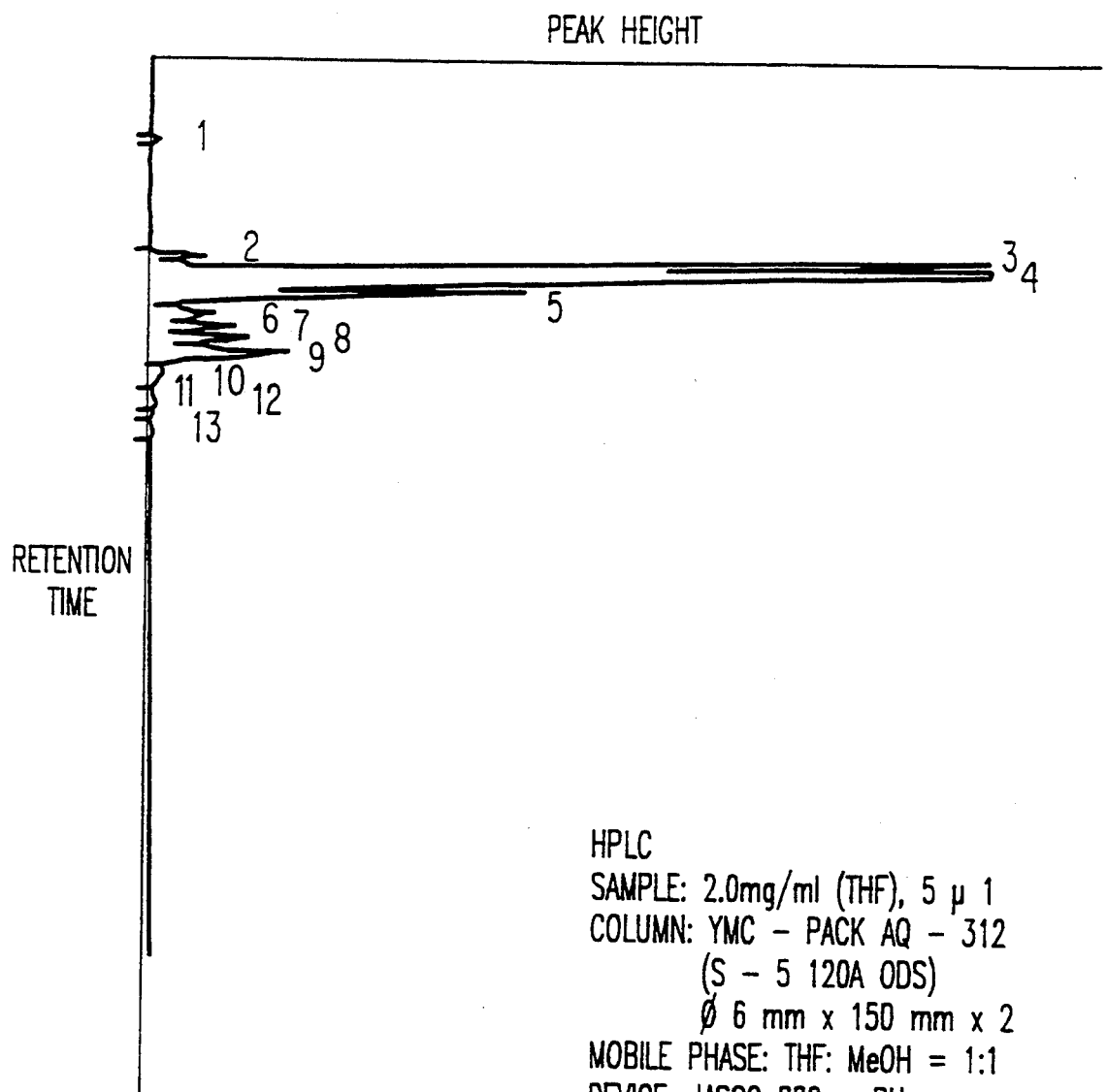

HALOGENATED PHTHALOCYANINE COMPOUND, METHOD FOR PREPARING SAME

TECHNICAL FIELD

The present invention relates to a halogenated alkoxyphthalocyanine which is useful as a dye, a pigment, a filter, a liquid crystal display material and a recording material. Furthermore, the present invention relates to an optical recording medium using the compound and a mixture thereof as well as a method for preparing the compound and the mixture.

BACKGROUND ART

Halogenated alkoxyphthalocyanines are disclosed in EP 0373643 and Japanese Patent Application Laid-open Nos. 197280/1986 and 85630/1975.

Techniques of using the halogenated alkoxyphthalocyanines as optical recording media are described in EP 373643, Japanese Patent Application Laid-open No. 197280/1986, U.S. Pat. No. 4,298,975, EP 353394 and U.S. Pat. No. 4,769,307. However, the optical recording media using the compounds described in the above-mentioned patents are insufficient in sensitivity, a refractive index, recording properties and reflectance.

In particular, EP 373643 discloses the phthalocyanines each having four alkoxy groups, or four alkoxy groups and four substituents. However, among the phthalocyanines disclosed in this patent, for example, the compounds shown in Examples 93 to 100 had a small refractive index of 2 or less at 780 nm and insufficient sensitivity and recording properties. On the other hand, the compounds shown in Examples 100 to 103 could not provide an industrially homogeneous recording layer, because the solubility of these compounds in a coating solvent was 10 g/l which was too low to prepare the optical recording medium therefrom in accordance with a spin coating process by the use of a polycarbonate substrate. In addition, the sensitivity, recording properties and reflectance of the media were insufficient.

With regard to the halogenation of the phthalocyanine, Publication Board Report No. 65,657 describes a method in which antimony trisulfide or aluminum chloride is used as a catalyst. However, this method could not be applied to such a phthalocyanine containing the alkoxy group as in the present invention, since the alkoxy group substituted on a benzene ring, for example, a phenyl alkyl ether decomposes in the presence of aluminum chloride into phenol and an alcohol. This decomposition reaction is described in the literatures of Chem. Ber., 76B, 900 (1943), J. Org. Chem. 27, 2037 (1962) and Chem. Ber., 93, 2761 (1960).

Furthermore, J. Org. Chem., 6, 852 (1941) and Chemical Industries, 1138 (1967) describe the decomposition reaction in which an acid byproduced in the halogenation reaction, for example, hydrogen chloride or hydrogen bromide produced at the halogenation with chlorine or bromine decomposes a phenyl ether into phenol and an alcohol.

DISCLOSURE OF THE INVENTION

A first object of the present invention is to provide a phthalocyanine compound or mixture which is useful as a recording layer for writable compact disks (abbreviate to "CD-WO") having excellent sensitivity and reflectance, a high refractive index and excellent recording properties.

A second object of the present invention is to provide a synthetic route of a halogenated alkoxyphthalocyanine compound or mixture thereof according to the present invention and optimum conditions for the synthesis.

A third object of the present invention is to provide a recording medium, particularly a CD-WO recording medium in which the halogenated alkoxyphthalocyanine compound or mixture thereof is contained in a recording layer.

The present inventors have intensively investigated with the intention of solving the above-mentioned problems, and as a result, they have found that a compound and mixture into which alkoxy groups having a large steric hindrance and halogen atoms are introduced are excellent in sensitivity, reflectance and recording properties and have a high refractive index as the CD-WO recording layer. It has also been found that the phthalocyanine compound and mixture containing the alkoxy groups in which the total number of the secondary, tertiary or quaternary carbons is from 2 to 4, and containing 1 to 4 halogen atoms, preferably bromine atoms are particularly preferable.

In preparing the optical recording medium, a substrate prepared from polycarbonate by extrusion molding is preferable from the viewpoints of transparency and economy. For the mass production, the recording layer is preferably applied by a spin coating method. That is, it has been found that in order to apply the recording layer in an optimum shape on the polycarbonate substrate without destroying guide grooves on the substrate, among the halogenated alkoxyphthalocyanines which can be provided in accordance with the present invention, what is particularly preferable is an isomer in which the symmetry of the alkoxy groups substituted is low, or an isomer of a phthalocyanine molecule in which the symmetry is low, that is, an isomer having no symmetrical center. Furthermore, it has been found that when five or more isomers are mixed, there can be achieved the optimization of solubility in a coating solvent, the stability of a coating solution and the shape of the applied recording layer.

Moreover, according to the present invention, there can be provided a method for preparing the halogenated alkoxyphthalocyanine. That is, there is a method for forming a phthalocyanine ring by mixing 2 to 4 kinds of isomers of halogenated alkoxyphthalonitriles and their derivatives, or a method for halogenating an alkoxyphthalocyanine. It has been found that particularly as the method for inexpensively preparing a mixture having different halogenation ratios by mixing of optimum isomers, it is preferable to carry out reaction in a mixed two-layer solvent system of water and an organic solvent which can form two layers with water. It has been found that when this method is used, the mixing of the isomers and the control of halogenation ratio are easy, and the halogenated alkoxyphthalocyanine having optimum maximum absorption wave length, a high refractive index, high reflectance, high sensitivity and excellent recording properties can be obtained in a high yield.

BRIEF DESCRIPTION OF THE DRAWINGS

FIG. 9 is a liquid chromatogram of a brominated alkoxyphthalocynine mixture obtained in Example 27.

BEST MODE FOR CARRYING OUT THE INVENTION

Figure 1:
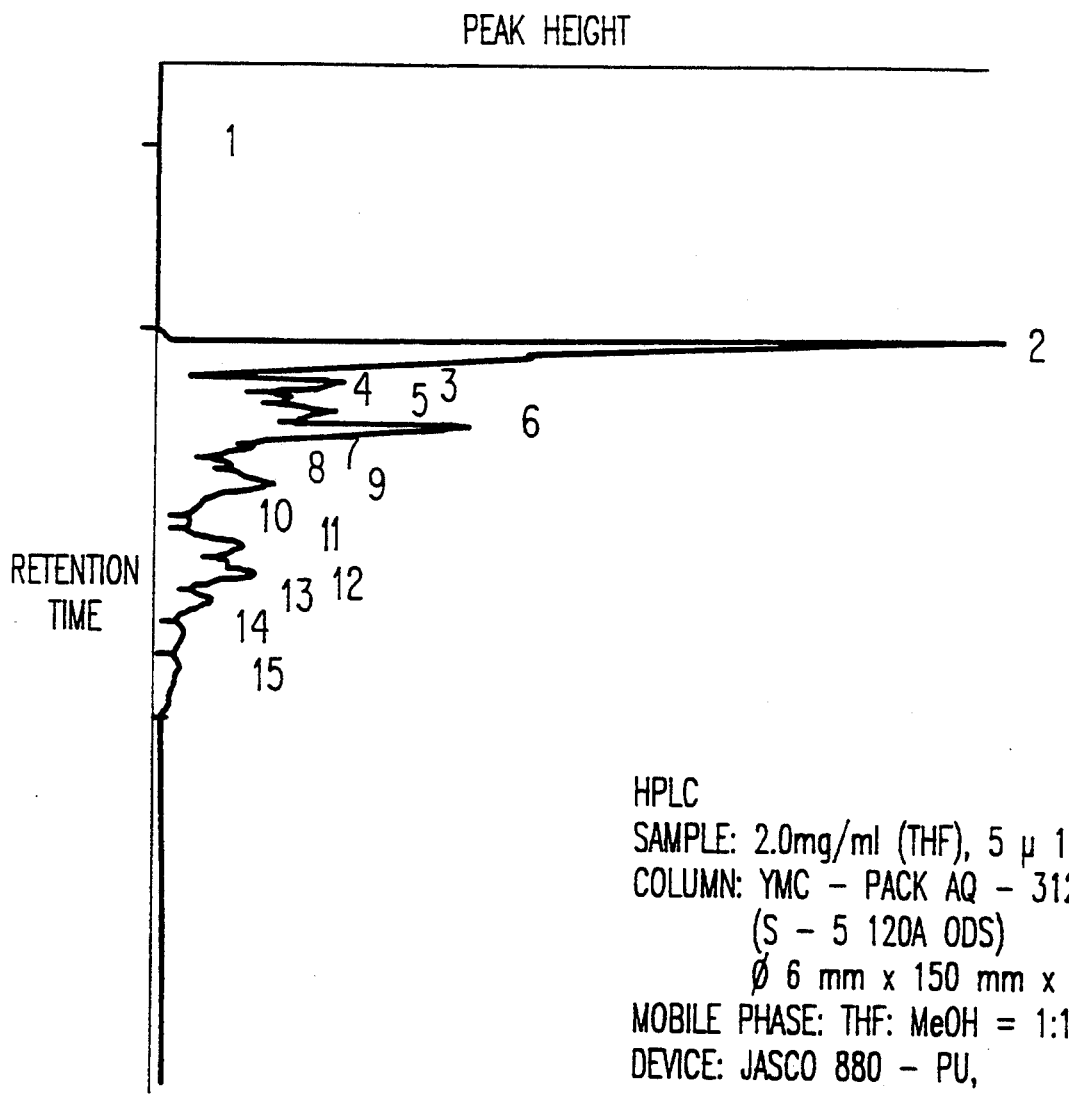
FIG. 1 is a liquid chromatogram of a brominated alkoxyphthalocynine mixture obtained in Example 18.

The present inventors have investigated compounds suitable for CD-WO, and they have found that it is particularly important to possess the following five features.

(1) Since CD-WO utilizes a laser beam at about 780 nm to write and read records, a recording material preferably has high sensitivity, a high refractive index and high reflectance at about 780 nm.

Therefore, the desirable recording material is a compound which has an absorbance at a maximum absorption wave length ($\lambda_{max}$), i.e., a maximum molecular extinction coefficient ($\epsilon_{max}$) of 150,000 or more and which can provide a recording medium having a refractive index of 1.8 or more, particularly preferably 2.0 or more at 780 nm.

(2) A phthalocyanine having a large steric hindrance, particularly a phthalocyanine having the combination of bromine atoms and alkoxy groups which has 2 to 4 of the secondary, tertiary or quaternary carbons and in which the total number of the carbon atoms is from 6 to 9 has good decomposability (a balance between a thermal decomposition starting temperature and a melting temperature) in a writing machine equipped with a semiconductor laser for carrying out CD-WO record.

A preferable substitution site of the alkoxy group is an α-position. That is, an isomer having any one of the following formulae (1) to (4) and particularly, having no symmetrical center and a mixture containing 50% or more of this kind of isomer is preferable.

(3) In order to have the high refractive index, the central metal is preferably an atom having a large atomic radius, i.e., Pd, Pt, Rh, Ru, In, VO or a derivative of Sn, or Cu, Ni, Co, Fe, Pd, Pt or VO in the viewpoint of durability.

(4) In the case that the symmetry of the molecule is low, for example, compounds represented by the following formulae (2), (3) and (4) as well as the undermentioned formulae (1-3), (1-4), (1-5), (1-6), (1-7) and (1-8) are excellent in solubility in a coating solvent. As a result, the uniform coating of the recording layer is possible, and it is also possible to form the recording layer in an optimum shape on a substrate.

(5) CD-WO is required a reflectance of 65% or more. Therefore, it is preferable to introduce, into a phthalocyanine, a substituent having a large steric hindrance and a halogen atom, preferably bromine or iodine having a large atomic refractive index as an auxiliary group for improving its steric hindrance effect.

That is, the present inventors have intensively investigated to solve the above-mentioned problems, and as a result, they have found that a halogenated alkoxyphthalocyanine substituted by alkoxy groups having 2 to 4 of the secondary to quaternary carbon atoms which can be represented by the formulae (1) to (4) is a preferable compound:

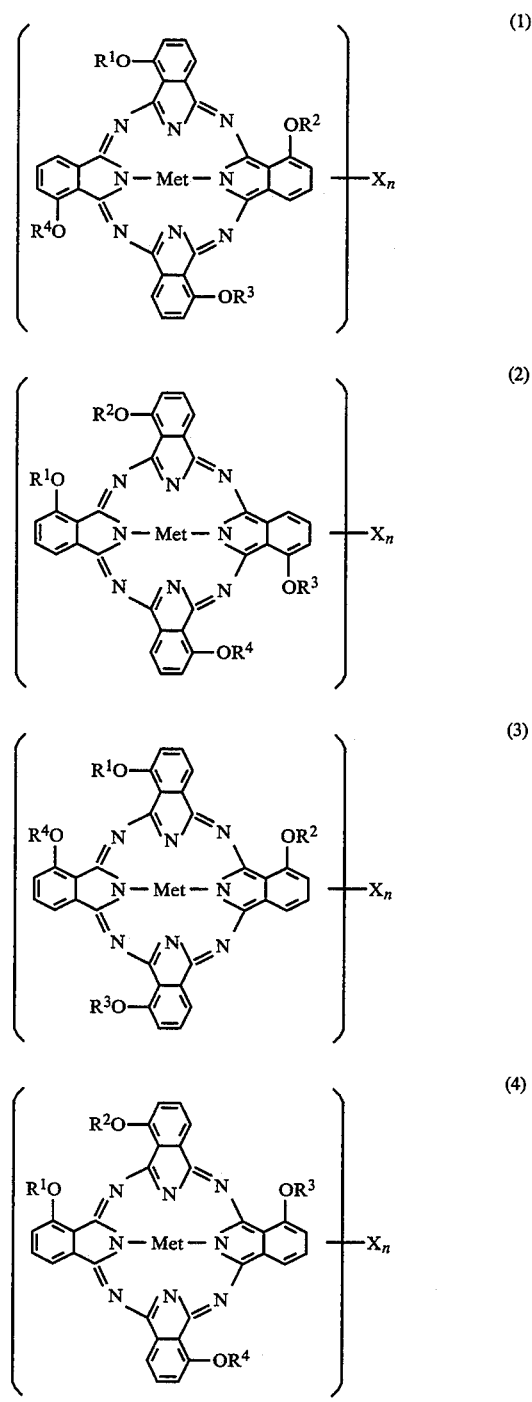

wherein each of $R^1$ to $R^4$ is independently an alkyl group which has 2 to 4 of the secondary, tertiary or quaternary carbon atoms and in which the total number of the carbon atoms is from 6 to 9; Met is a divalent metallic atom, a trivalent one-substituted metallic atom or a tetravalent two-substituted metallic atom; X is a halogen atom such as chlorine, bromine or iodine; and n is the substitution number of X and it is from 1 to 4.

That is, the increase of the steric hindrance of the alkoxy groups leads to drop a decomposition temperature and to elevate a melting point. Accordingly, the writing can be effected by a small laser power, and the shape of each written signal is good.

Among the halogenated alkoxyphthalocyanines represented by the formulae (1) to (4), the following compounds are particularly preferable. That is, it has been found that compounds which are particularly desirable to solve the above-mentioned problems are the halogenated alkoxyphthalocyanine compounds in which the substituent represented by each of $R^1$ to $R^4$ is one selected from the group consisting of a 1-iso-propyl-2-methylbutyl group, 1-t-butyl-2-methylpropyl group, 1-iso-propyl-2-methylpropyl group, 1,2-dimethylbutyl group, 1-iso-propylpropyl group and 1-isopropylbutyl group; the central metal Met is one selected from the group consisting of VO (vanadium oxide), divalent metallic atoms such as iron, cobalt, nickel, copper, zinc, ruthenium, rhodium, palladium and platinum and their derivatives; and the halogen atom is a bromine atom; and the number of the bromine atoms is from 1 to 4.

A compound which is preferable as a raw material in the method for preparing the compound of the present invention is one to four kinds of alkoxyphthalonitriles or alkoxydiiminoisoindolines represented by the formula (5) or (6)

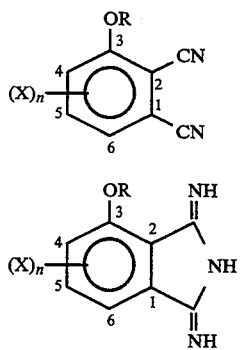

wherein R is an alkyl group which has 2 to 4 of the secondary, tertiary or quaternary carbon atoms and in which the total number of the carbon atoms is from 6 to 9; X is a halogen atom such as chlorine, bromine or iodine and is bonded at the 4-position or 6-position; and n is 0 or 1, and at least one of these compounds has the substituent X.

The particularly preferable raw material is a compound of the formula (5) or (6) in which R is one selected from the group consisting of a 1-iso-propyl-2-methylbutyl group, 1-t-butyl-2-methylpropyl group, 1-iso-propyl-2-methylpropyl group, 1,2 -dimethylbutyl group, 1-iso-propylpropyl group and 1-iso-propylbutyl group; and X is bromine.

Examples of a metal or a metallic compound which is another raw material of the present invention include aluminum, silicon, titanium, vanadium, chromium, manganese, iron, cobalt, nickel, copper, zinc, gallium, germanium, ruthenium, rhodium, palladium, indium, tin, platinum and chlorides, bromides, iodides, acetates and oxides thereof. Examples of the particularly preferable raw material include iron chloride, iron bromide, iron acetate, cobalt chloride, cobalt bromide, cobalt acetate, nickel chloride, nickel bromide, nickel acetate, copper chloride, copper bromide, copper iodide, copper acetate, zinc chloride, zinc bromide, zinc acetate, ruthenium chloride, rhodium chloride, rhodium bromide, palladium chloride, palladium bromide, palladium acetate, platinum chloride and platinum bromide.

With regard to conditions for the synthesis of a phthalocyanine ring, one to four kinds of alkoxyphthalonitriles or alkoxydiiminoisoindolines which are the raw materials are heated and reacted at 10° to 300° C. in a solvent, preferably an alcohol. When the raw material is the alkoxyphthalonitrile represented by the formula (5), a reaction temperature is preferably from 80° to 160° C. Furthermore, when the raw material is the alkoxydiiminoisoindoline represented by the formula (6), the reaction temperature is preferably from 140° to 200° C. In addition, an auxiliary such as diazabicycloundecene (DBU) or diazabicylononene (DBN) may be added as a catalyst for the ring formation reaction.

The alkoxyphthalonitrile (5) or the diiminoisoindoline (6) which is used in the present invention can be synthesized by the following procedure:

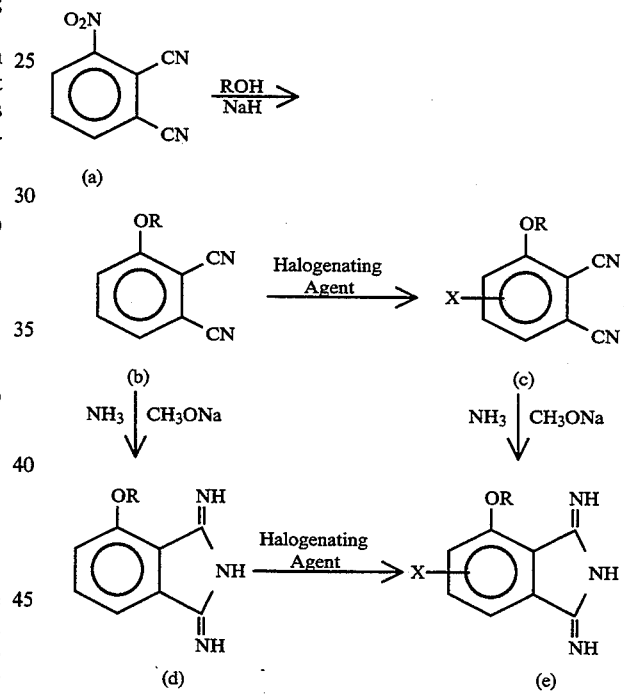

3-nitrophthalonitrile is available, for example, from Tokyo Chemicals, Inc. The synthesis of an alkoxyphthalonitrile (b) from a nitrophthalonitrile (a) can be achieved by a method described in NOUVEAU JOURNAL DE CHIMIE, Vol. 6, No. 12, p 653–58 (1982). That is, an alcohol is converted into sodium alkoxide with the aid of sodium hydride, and it is successively reacted with nitrophthalonitrile at 0° to 100° C. to form the alkoxyphthalonitrile.

A halogenated alkoxyphthalonitrile (c) can be synthesized by halogenating an alkoxyphthalonitrile in accordance with a method described in I. T. Harrison and S. Harrison, "COMPENDIUM OF ORGANIC SYNTHETIC METHODS", Vol. 1-6, Wiley-Interscience Co., Ltd., and then carrying out separation/purification by column chromatography. Preferable examples of a halogenating agent which can be used in the above-mentioned halogenation include chlorine, bromine, iodine, sulfuryl chloride, thionyl chloride, antimony chloride, ICl₃, FeCl₃, phosphorus pentachloride, phosphorus oxychloride, t-butyl hypochlorite, N-chlorosuccinic acid imide, cupric bromide, quaternary ammonium bromide, N-bromosuccinimide, iodine monochloride, quaternary ammonium iodide and potassium triiodide. The halogenating agent can be suitably used in the range of 1 to 2 moles per mole of the alkoxyphthalonitrile.

Moreover, an alkoxydiiminoisoindoline (d) can be synthesized from the above-mentioned alkoxyphthalonitrile (b), and a halogenated alkoxydiiminoisoindoline (e) can be synthesized from the above-mentioned halogenated alkoxyphthalonitrile (c) by a reaction with ammonia. In addition, the compound (e) can be synthesized by halogenating the compound (d) in the same manner as mentioned above.

The present inventors have found an economically excellent procedure of synthesizing a mixture of isomers having different halogenation degrees in which the halogenated alkoxyphthalocyanine having a controlled halogenation ratio can be obtained by reacting the alkoxyphthalocyanine at an adjusted reaction temperature in an adjusted amount of a two-layer system mixed solvent containing, as the main components, water and an organic solvent which is not substantially mixed with water such as an aliphatic hydrocarbon, a halogenated hydrocarbon and a straight-chain or cyclic ether. In consequence, the present invention has been attained. If this reaction is carried out by a conventional technique, it does not wonder that a hydroxyphthalocyanine which is product obtained from a decomposition reaction of the alkoxy groups is produced in large quantities as a by-product. However, surprisingly, the present inventors have found that when the present invention is carried out, the by-production of the hydroxyphthalocyanine is so extremely small as not to affect the quality of the aimed product.

In general, the method for preparing the halogenated alkoxyphthalocyanine is described in Japanese Patent Laid-Open No. 50-85630 and J. Chem. Soc., Perkin Trans. I, p. 2453-58 (1988). The former describes a method comprising the step of substituting the halogenated phthalocyanine by an alkali metal salt of an aliphatic alcohol or an alkali metal salt of an aromatic alcohol to prepare the desired halogenated alkoxyphthalocyanine or halogenated aryloxyphthalocyanine. The latter describes a method comprising the step of subjecting a dialkoxydihalogenophthalonitrile to a ring closure reaction to prepare the desired halogenated alkoxyphthalocyanine. However, this method could not be applied to a process for introducing 1 to 4 halogen atoms into a tetraalkoxyphthanocyanine.

In general, a halogenation method comprises the step of dissolving a substrate in a solvent which is inert to the halogenating agent to accomplish the halogenation. However, the inventors have found that when the reaction is carried out in a halogenating agent such as chloroform or carbon tetrachloride or acetic acid at the time of the halogenation of the alkoxyphthalocyanine compound, a solid precipitates during the reaction, so that the halogenating reaction does not proceed sufficiently and it is difficult to control the amount of the halogen atom to be introduced.

That is, the present invention is directed to a method for preparing a halogenated phthalocyanine compound represented by the formula (8)

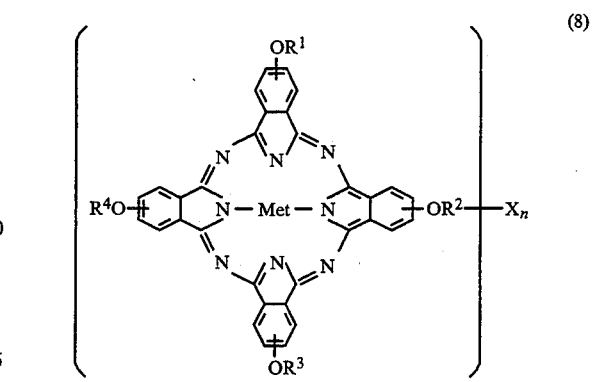

wherein each of $R^1$, $R^2$, $R^3$ and $R^4$ independently is an alkyl group having 1 to 20 carbon atoms, preferably a substituted or unsubstituted alkyl group having 3 to 10 carbon atoms; and Met is two hydrogen atoms, a divalent metallic atom, a trivalent or a tetravalent metallic derivative; X is chlorine, bromine or iodine; and n is $1 \leq n \leq 12$, which comprises the step of reacting a phthalocyanine compound represented by the formula (7)

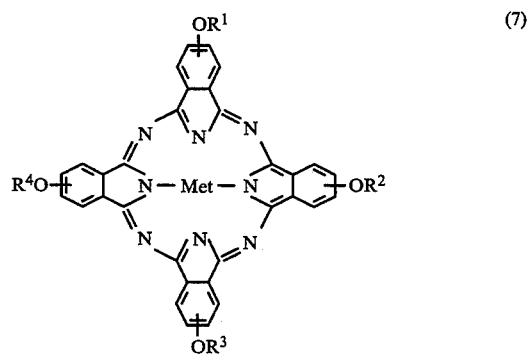

wherein $R^1$, $R^2$, $R^3$, $R^4$ and Met have the same meanings as in the formula (8), with a halogenating agent at 20° to 90° C. in a mixed solvent of an organic solvent and water. The compounds represented by the formulae (7) and (8) in which two or more of $OR^1$, $OR^2$, $OR^3$ and $OR^4$ are bonded to one benzene ring are also in the category of the present invention.

It can be presumed that when the phthalocyanine compound is reacted with the halogenating agent in the mixed solvent of water and the organic solvent which is not substantially mixed with water in accordance with the present invention, a hydrogen halide or a salt of the halogenating agent and the like which are by-products of the reaction are dissolved in water, whereby the phthalocyanine compound is prevented from precipitating together with the by-products of the reaction from the organic solvent which is the reaction solvent. In the case of the alkoxy group having the large steric hindrance, the compound substituted by 2 or more halogen atoms cannot be synthesized sometimes, if water is not present.

The particularly preferable alkoxyphthalocyanines as the raw material of the present invention are α-alkoxyphthalocyanines represented by the formulae (9) to (12). As the raw material, it is preferable to use a mixture of (9) to (12)

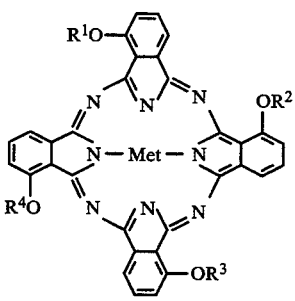

(9)

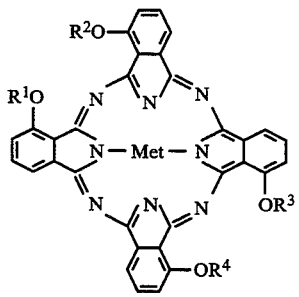

(10)

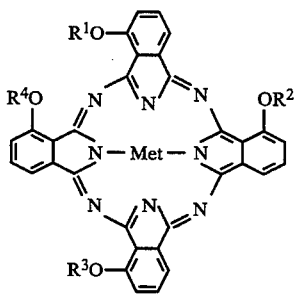

(11)

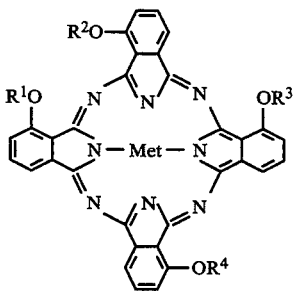

(12)

wherein each of $R^1$, $R^2$, $R^3$ and $R^4$ is independently an alkyl group having 1 to 20 carbon atoms, preferably a substituted or unsubstituted alkyl group having 3 to 10 carbon atoms; Met is two hydrogen atoms, a divalent metallic atom, a trivalent or a tetravalent metallic derivative.

In the preferable raw material, $R^1$, $R^2$, $R^3$ and $R^4$ of the formulae (9) to (12) are the branched alkyl groups. In the particularly preferable raw material, $R^1$, $R^2$, $R^3$ and $R^4$ of the formulae (9) to (12) are the secondary alkyl groups.

Examples of the substituted and unsubstituted alkyl groups of $R^1$, $R^2$, $R^3$ and $R^4$ in the formulae (7) and (9) to (12) include hydrocarbon groups such as a methyl group, ethyl group, n-propyl group, iso-propyl group, n-butyl group, iso-butyl group, sec-butyl group, t-butyl group, n-pentyl group, iso-pentyl group, neo-pentyl group, 1,2-dimethylpropyl group, n-hexyl group, cylcohexyl group, 1,3-dimethylbutyl group, 1-iso-propyl- propyl group, 1,2-dimethylbutyl group, n-heptyl group, 1,4-dimethylpentyl group, 2-methyl-1-iso-propylpropyl group, 1-ethyl-3-methylbutyl group, n-octyl group, 2-ethylhexyl group, 3-methyl-1-iso-propylbutyl group, 2-methyl-1-isopropylbutyl group, 1-t-butyl-2-methylpropyl group and n-nonyl group; alkoxyalkyl groups such as a methoxymethyl group, methoxyethyl group, ethoxyethyl group, propoxyethyl group, butoxyethyl group, methoxyethoxyethyl group, ethoxyethoxyethyl group, dimethoxymethyl group, diethoxymethyl group, dimethoxyethyl group and diethoxyethyl group; and halogenated alkyl groups such as a chloromethyl group, 2,2,2-trichloroethyl group, trifluoromethyl group, 1,1,1,3,3,3-hexafluoro-2-propyl group.

Above all, the preferable alkyl group is the alkyl group having 2 to 4 of the secondary, tertiary and quaternary carbon atoms in all, and particularly, examples of such an alkyl group include a 1,2-dimethylpropyl group, 1,3-dimethylbutyl group, 1-iso-propylpropyl group, 1,2-dimethylbutyl group, 1,4-dimethylpentyl group, 2-methyl-1-iso-propylpropyl group, 1-ethyl-3-methylbutyl group, 3-methyl-1-isopropylbutyl group, 2-methyl-1-iso-propylbutyl group and 1-t-butyl-2-methylpropyl group.

Examples of the divalent metal represented by Met in the formulae (7) and (9) to (12) include Cu, Zn, Fe, Co, Ni, Ru, Rh, Pd, Pt, Mn and Sn; examples of the monosubstrated trivalent metal include Al-Cl, Al-Br, In-Cl, In-Br and In-I; examples of the divalent tetravalent metal include $SiCl_2$, $SiBr_2$, $SiF_2$, $SnCl_2$, $SnBr_2$, $SnF_2$, $GeCl_2$, $GeBr_2$, $GeF_2$, $Si(OH)_2$, $Sn(OH)_2$ and $Ge(OH)_2$; and examples of the metallic oxide include VO and TiO. Particularly preferable examples include Cu, Ni, Pd and Pt.

The halogenating agent which can be used in the present invention is a compound represented by the formula (13)

$$X-Y \qquad (13)$$

wherein X is a halogen atom, and Y is a residue of the halogenating agent. Examples of the halogen atoms include F, Cl, Br and I, and Br is preferable. Examples of the residue of the halogenating agent include Cl, Br, I, $SO_2Cl$, SOCl, $FeCl_2$, $PCl_4$, $POCl_2$, CuBr and quaternary ammonium.

Typical examples of the halogenating agent include chlorine, bromine, iodine, sulfury chloride, thionyl chloride, antimony chloride, $ICl_3$, $FeCl_3$, phosphorus pentachloride, phosphorus oxychloride, t-butyl hypochlorite, N-chlorosuccinic imide, cupric bromide, quaternary ammonium bromide, N-bromosuccinimide, iodine monochloride, quaternary ammonium iodide and potassium tri-iodide. Particularly, bromine is preferable. The halogenating agent can be suitably used in the molar ratio of 1 to 6 moles followed by the desirably introduced halogen quantity. It has been found that when bromine is used, there is a particularly definite feature. That is, when bromine is used in a molar ratio of 2 moles per mole of the alkoxyphthalocyanine, 1, 2, 3 or 4 bromine atoms are introduced. When bromine is used in a molar ratio of 2.5 to 4.0 moles, 2, 3 or 4 bromine atoms are introduced. Even if 4 moles or more of bromine are used, the maximum number of the bromine atoms to be introduced is 4.

A reaction temperature is in the range of 20° to 90° C., preferably 40° to 70° C. When the reaction temperature is less than 20° C. the reaction does not proceed successively, and when it is more than 90° C., it is difficult to control a halogenation ratio.

The organic solvent is a solvent which is substantially immiscible with water, i.e., a solvent which forms two layers with water and which can dissolve the phthalocyanine compounds of the formulae (7) and (9) to (12). The preferable organic solvent is one or more selected from saturated hydrocarbons, ethers and halogenated hydrocarbons. The further preferable organic solvent is one or more selected from the group consisting of n-hexane, n-pentane, n-octane, cyclohexane, methylcyclohexane, ethylcyclohexane, tetrahydrofuran, n-butyl ether, n-propyl ether, isopropyl ether, carben tetrachloride, chloroform, dichloromethane, 1,1,1-trichloroethane, 1,1,2-trichloroethane and 1,1,2,2-tetrachloroethane.

The amount of the organic solvent is 2 to 500 times by weight, preferably 3 to 200 times by weight as much as that of the phthalocyanine which is the raw material. It is necessary to completely dissolve the phthalocyanine. However, when the amount of the organic solvent is less than 2 times by weight, a solid tends to precipitate during the reaction and impedes the reaction, and conversely when it is more than 500 times by weight, the reaction is improperly too slow. In particular, when 1,1,2-trichloroethane or 1,1,2,2-tetrachloroethane is used, the amount of the organic solvent is preferably from 4 to 10 times by weight.

The amount of water is 0.05 to 10 times by weight, preferably 0.1 to 5 times by weight as much as that of the organic solvent. It is necessary to obtain such a ratio that many interfaces are formed between water and the organic solvent. When the amount of water is less than 0.05 times by weight, there is no effect of mixing water, and the solid easily precipitates during the reaction and impedes the reaction. Conversely, when it is more than 10 times by weight, the amount of the solvent is too much and the efficiency of the reaction deteriorates improperly.

The halogenated alkoxyphthalocyanine prepared under the above-mentioned conditions is represented by the formula (8):

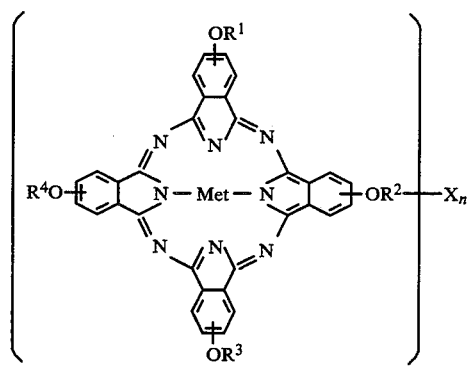

(8)

wherein $R^1$, $R^2$, $R^3$, $R^4$ and Met have the same meanings as in the formula (7); X is chlorine, bromine or iodine; and n is $1 \leq n \leq 12$. Preferable examples of the halogenated alkoxyphthanocyanine are compounds represented by the following formulae (1) to (4) and mixtures thereof:

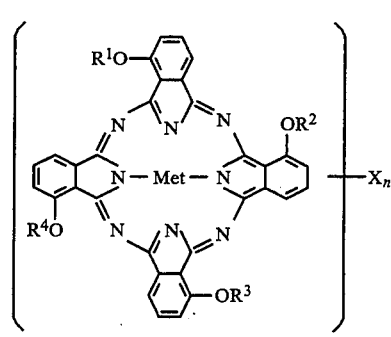

(1)

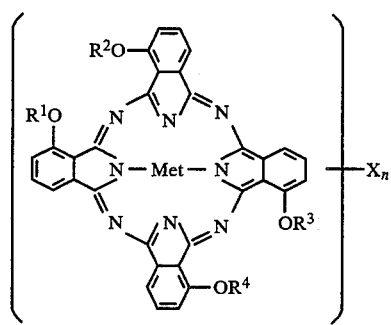

(2)

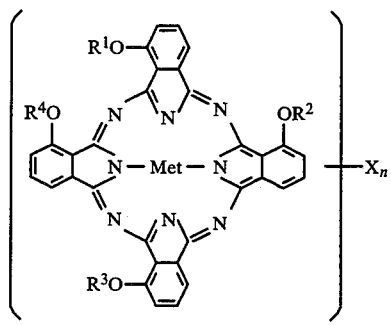

(3)

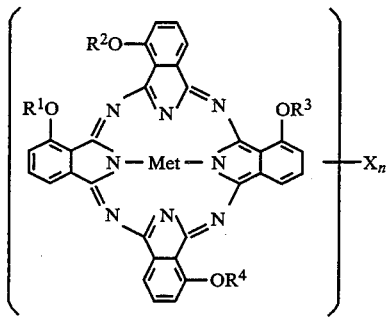

(4)

wherein $R^1$, $R^2$, $R^3$, $R^4$, Met and X have the same meanings as in the formula (8).

In the halogenated alkoxyphthalocyanines represented by the formulae (1) to (4) and the mixtures thereof, it is most preferable that each of $R^1$ to $R^4$ is a secondary alkyl group, particularly an alkyl group having 2 to 4 of the secondary, tertiary and quaternary carbon atoms in all.

The thus prepared halogenated alkoxyphthalocyanine is a mixture of 5 or more kinds of isomers or compounds having different contents of bromine. When this mixture is used without separation to prepare an optical recording medium, the medium which can solve the above-mentioned problems can be obtained. Even if the composition ratio of this mixture alters, the performance of the mixture as the optical recording medium does not deteriorate, but one or a mixture of 2 or 3 of the halogenated alkoxyphthalocyanines cannot solve the above-mentioned problems to a sufficient degree.

The recording medium which is suitable for the compound of the present invention has a constitution in which a recording layer, a reflective layer and a protective layer are laminated in this order on a substrate.

A resin for use in the substrate of the present invention should be optically transparent. Example of the material for the substrate include a polyacrylic resin, polyolefin resin, polycarbonate resin and polyester resin. In this case, the surface of the substrate maybe covered with a photosetting resin or thermosetting resin.

Examples of the resin for the protective layer include a thermosetting resin and photosetting resin such as an acrylic resin and a urethane resin. The thickness of the protective layer is preferably from 1 μm to 1 mm.

Examples of the material for the reflective layer include metals such as aluminum, gold and silver. The thickness of the reflective layer is preferably from 20 to 200 nm.

The recording layer can be prepared by applying, on the substrate, a coating solution containing the compound of the present invention and a binder resin in an amount of 20% by weight or less based on the compound by the use of a spin coater. The concentration of the coating solution is preferably from 5 to 100 g/l. Any coating solvent can be used, so long as it does not attack the substrate. Preferable examples of the coating solvent include n-hexane, cyclohexane, n-octane, ethylcyclohexane, methylcyclohexane, cyclooctane, tetrachloroethane, carbon tetrachloride, dichloromethane, chloroform, THF, dioxane and a mixture thereof. The thickness of the recording layer is preferably from 50 to 300 nm.

The alkoxyphthalocyanines represented by the formulae (7), (9) to (12) can be prepared by methods described in U.S. Pat. No. 4,769,307 and NOUVEAU JOURNAL DE CHIMIE, Vol. 6, No. 12, p. 653–58 (1982). That is, the alkoxyphthalocyanine can be synthesized in accordance with the following reaction (14):

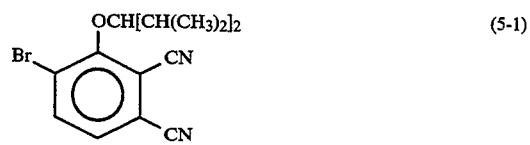

In the first place, an alcohol is reacted with sodium hydride at 0° to 30° C. to form a sodium alkoxide, and nitrophthalonitrile is successively added thereto and reaction is then carried out at 0° to 100° C. to obtain an alkoxyphthalonitrile. Next, the thus obtained alkoxyphthalonitrile is reacted with a metallic salt being a molar ratio of 0.8 to 1.2 at 100° to 300° C. in an alcohol to obtain an alkoxyphthalocyanine. Alternatively, a diiminoisoindoline may be derived from the alkoxyphthalonitrile and then reacted with a metallic salt to similarly obtain the alkoxyphthalocyanine.

Now, the present invention will be described in detail with reference to examples, but the scope of the present invention should not be limited only to these examples.

EXAMPLE 1

Ten grams of phthalonitrile represented by the following formula (5-1) were mixed with 2 g of palladium chloride, 4 g of DBU and 200 g of n-amyl alcohol, and reaction was then carried out at 95° C. for 24 hours.

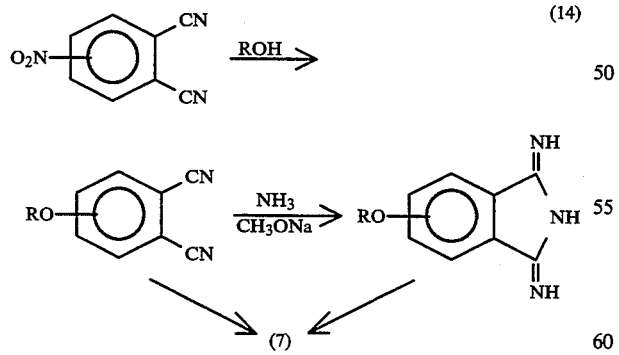

The resultant reaction mixture was poured into 1 liter of methanol, and the precipitated tar was then separated/purified by column chromatography to obtain 2 g of the following formula (1-1), 2 g of (2-1), 0.5 g of (3-1) and 0.5 g of (4-1). Physical properties of these compounds are set forth in Table 1.

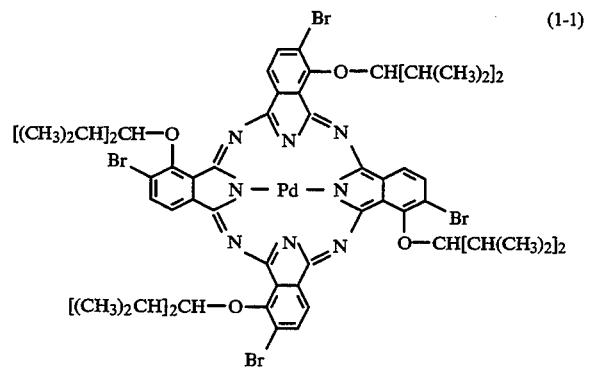

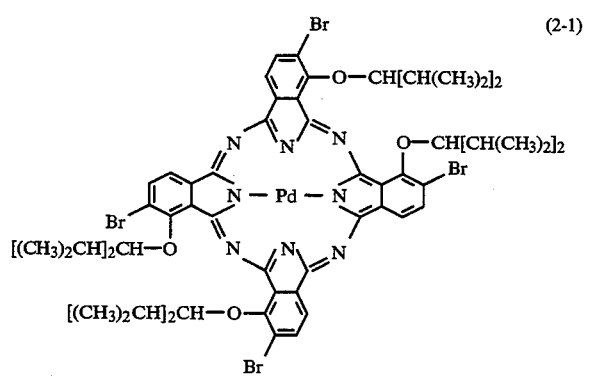

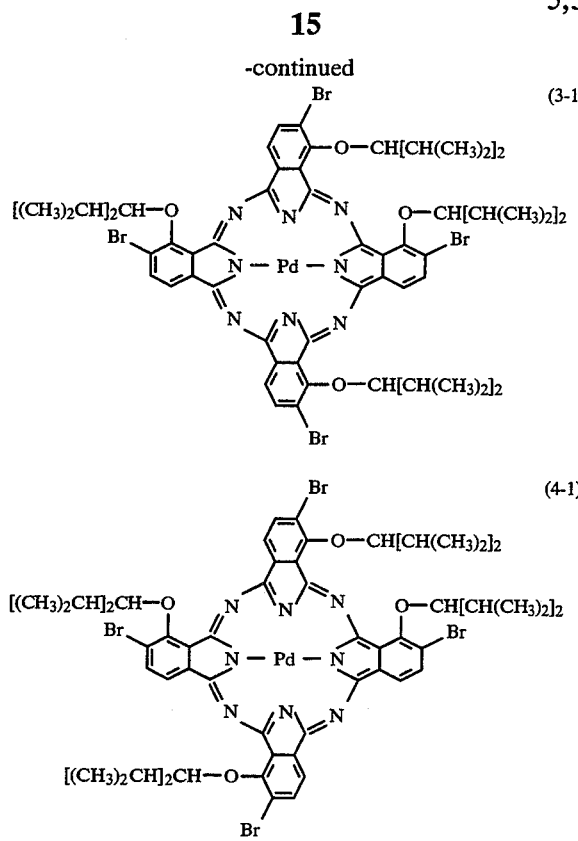

EXAMPLE 2

Ten grams of diiminoisoindoline represented by the following formula (6-1), 2 g of palladium chloride, 4 g of DBU and 200 g of n-octyl alcohol where mutually mixed, and reaction was then carried out under reflux for 4 hours.

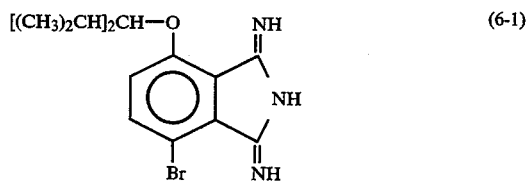

The resultant reaction mixture was poured into 1 liter of methanol, and the precipitated tar was then separated/purified by column chromatography to obtain 0.5 g of the following formula (1-2), 0.1 g of (2-2), 5.1 g of (3-2) and 0.5 g of (4-2). Physical properties of these compounds are set forth in Table 2.

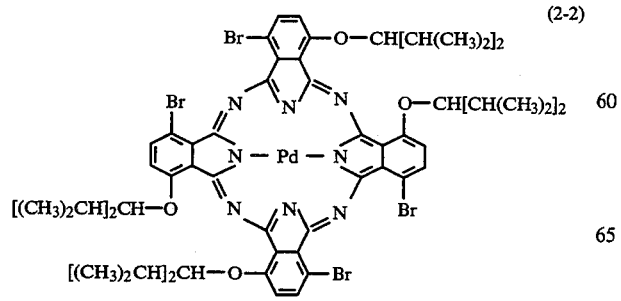

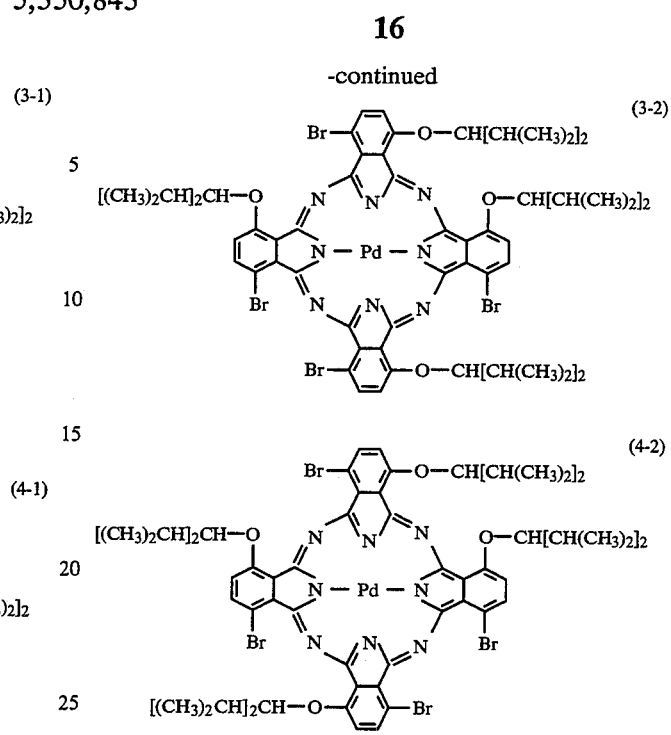

TABLE 2

| Compound No. | $\lambda_{max}$(nm) ($\epsilon_{max} \times 10^{-5}$) | mass (m/e) | Elemental Analysis (C,H,N) Found (Calcd.) |
|---|---|---|---|
| (1-2) | 716 (2.2) | 1391 | 51.79, 4.92, 8.04 (51.80, 4.93, 8.05) |
| (2-2) | 715 (2.2) | 1391 | 51.81, 4.90, 8.06 (51.80, 4.93, 8.05) |
| (3-2) | 716 (2.1) | 1391 | 51.82, 4.92, 8.06 (51.80, 4.93, 8.05) |
| (4-2) | 715 (2.2) | 1391 | 51.79, 4.90, 8.04 (51.80, 4.93, 8.05) |

EXAMPLE 3

Five grams of phthalonitrile represented by said formula (5-1), 5 g of phthalonitrile represented by the following formula (5-2), 2 g of palladium chloride, 4 g of DBU and 200 g of n-amyl alcohol were mutually mixed, and reaction was then carried out at 95° C. for 4 hours.

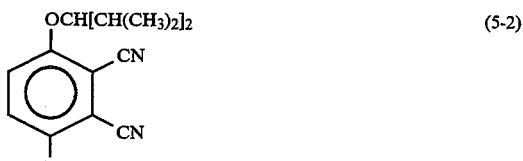

The resultant reaction mixture was poured into 1 liter of methanol, and the precipitated tar was then separated/purified by column chromatography to obtain 0.1 g of the following formula (1-3), 0.1 g of (1-4), 0.5 g of (1-5) and 0.3 g of (1-6). Physical properties of these compounds are set forth in Table 3.

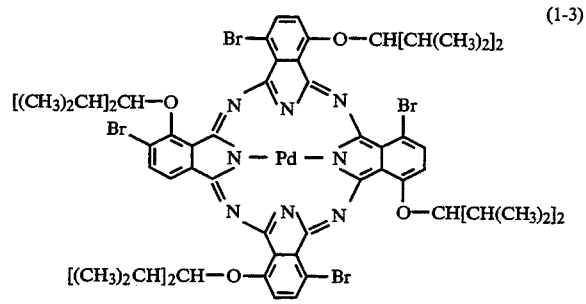
(1-3)

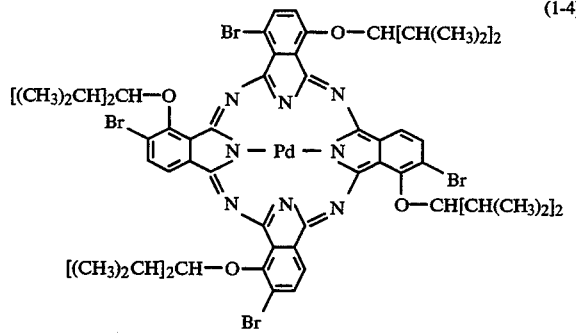
(1-4)

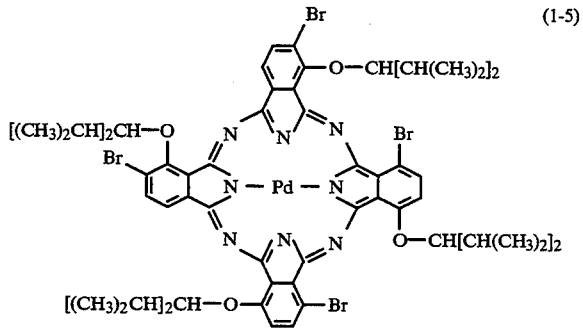
(1-5)

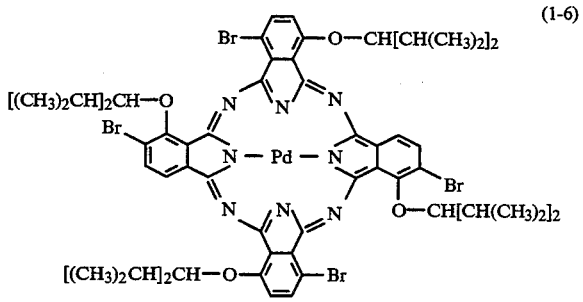
(1-6)

TABLE 3

| Compound No. | $\lambda_{max}$(nm) ($\epsilon_{max} \times 10^{-5}$) | mass (m/e) | Elemental Analysis (C,H,N) Found (Calcd.) |
|---|---|---|---|
| (1-3) | 716 (2.2) | 1391 | 51.67, 4.95, 8.10 (51.80, 4.93, 8.05) |
| (1-4) | 716 (2.2) | 1391 | 51.90, 4.88, 7.99 (51.80, 4.93, 8.05) |
| (1-5) | 716 (2.2) | 1391 | 51.85, 4.87, 8.11 (51.80, 4.93, 8.05) |
| (1-6) | 715 (2.2) | 1391 | 51.78, 4.87, 7.99 (51.80, 4.93, 8.05) |

EXAMPLE 4

Eight grams of phthalonitrile represented by said formula (5-1), 2 g of phthalonitrile represented by the following formula (5-3), 2 g of palladium chloride, 4 g of DBU and 300 g of n-amyl alcohol were mutually mixed, and reaction was then carried out at 95° C. for 24 hours.

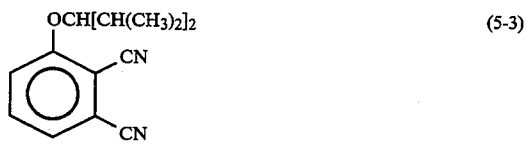
(5-3)

The resultant reaction mixture was poured into 1 liter of methanol, and the precipitated tar was then separated/purified by column chromatography to obtain 0.2 g of the following formula (3-3), 0.5 g of (3-4), 0.3 g of (3-5), 0.2 g of (1-7), 0.2 g of (1-1) and 0.2 of (3-1). Physical properties of these compounds are set forth in Table 4.

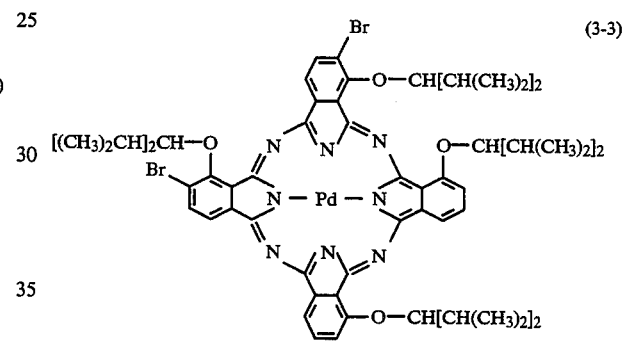
(3-3)

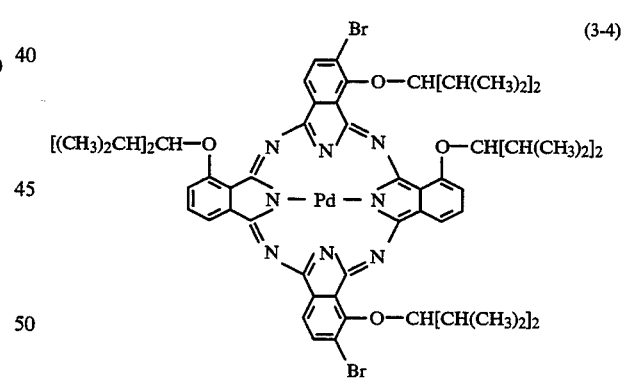
(3-4)

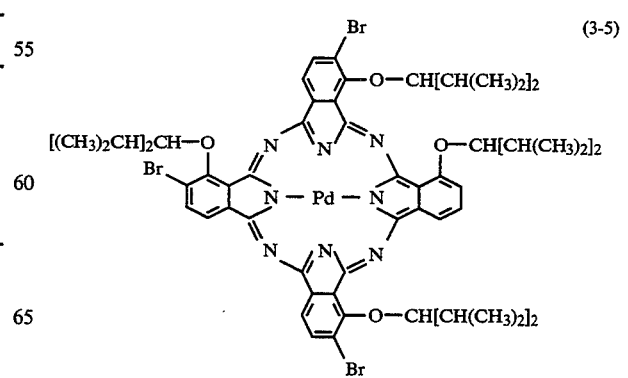
(3-5)

-continued

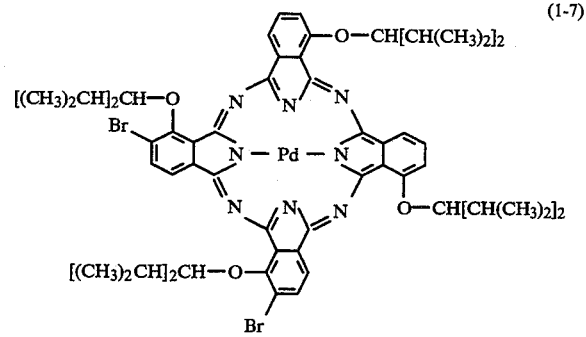
(1-7)

EXAMPLE 5

Seven grams of diiminoisoindoline represented by said formula (6-1), 3 g of diiminoisoindoline represented by the following formula (6-2), 2 g of palladium chloride, 4 g of DBU and 300 g of n-octyl alcohol were mutually mixed, and reaction was then carried out under reflux for 4 hours.

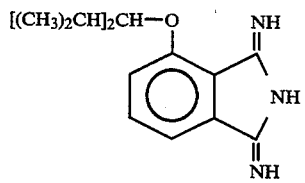
(6-2)

The resultant reaction mixture was poured into 1 liter of methanol, and the precipitated tar was then separated/purified by column chromatography to obtain 0.4 g of the following formula (3-6), 0.3 g of (1-8), 0.2 g of (3-7), 0.2 g of (3-8), 0.2 g of (1-9), 0.1 g of (3-9), 0.2 g of (1-10), 0.2 g of (3-2) and 0.2 g of (1-2). Physical properties of these compounds are set forth in Table 5.

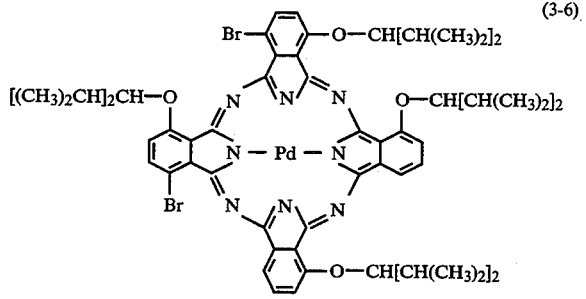
(3-6)

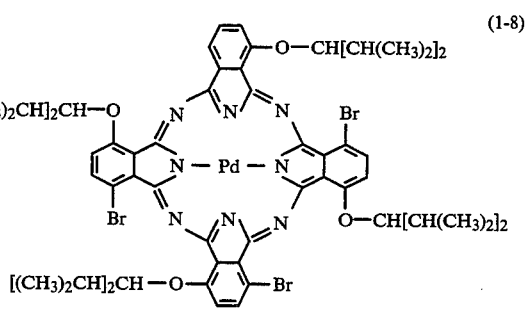
(1-8)

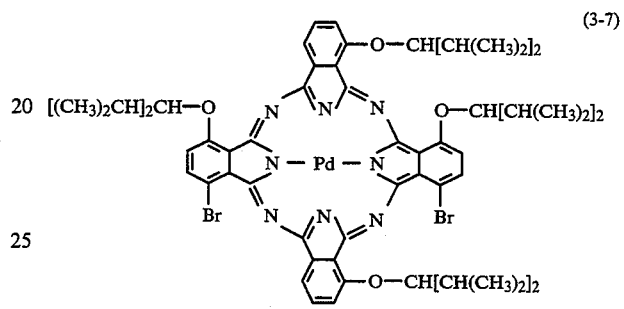
(3-7)

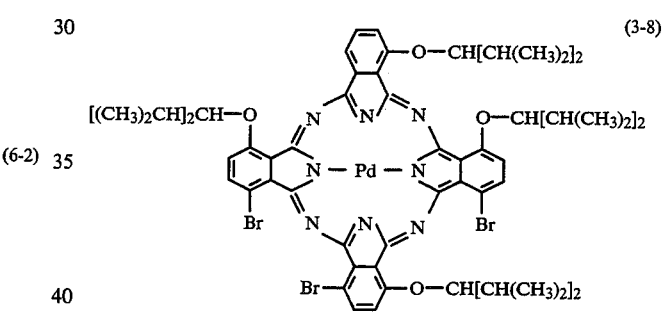
(3-8)

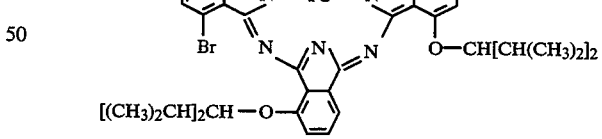
(1-9)

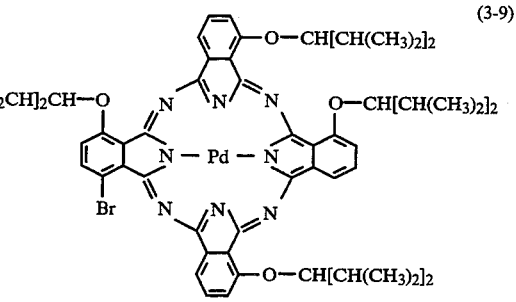
(3-9)

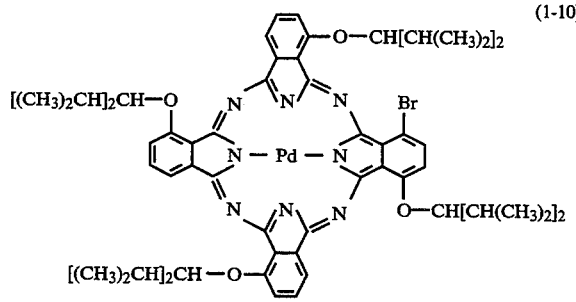

TABLE 5

| Compound No. | $\lambda_{max}$(nm) ($\epsilon_{max} \times 10^{-5}$) | mass (m/e) | Elemental Analysis (C,H,N) Found (Calcd.) |
|---|---|---|---|
| (3-6) | 698 (2.3) | 1233 | 58.31, 5.87, 9.01 (58.42, 5.72, 9.08) |
| (1-8) | 705 (2.2) | 1312 | 54.98, 5.28, 8.61 (54.91, 5.30, 8.54) |
| (3-7) | 699 (2.3) | 1233 | 58.52, 5.66, 9.03 (58.42, 5.72, 9.08) |
| (3-8) | 707 (2.2) | 1312 | 55.01, 5.27, 8.48 (54.91, 5.30, 8.54) |
| (1-9) | 698 (2.2) | 1233 | 58.33, 5.79, 9.15 (58.42, 5.72, 9.08) |
| (3-9) | 694 (2.3) | 1154 | 62.21 6.27, 9.48 (62.41, 6.20, 9.70) |
| (1-10) | 695 (2.2) | 1154 | 62.63, 6.79, 9.15 (62.41, 6.20, 9.70) |

EXAMPLE 6

Seven grams of diiminoisoindoline represented by the following formula (6-3), 2 g of diiminoisoindoline represented by the following formula (6-4), 2 g of palladium chloride, 4 g of DBU and 300 g of n-octyl alcohol were mutually mixed, and reaction was then carried out at 175° C. for 12 hours.

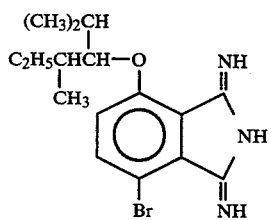

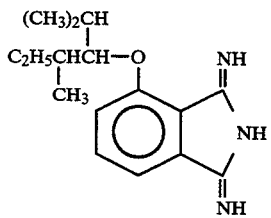

The resultant reaction mixture was poured into 1 liter of methanol, and the precipitated tar -was then separated/purified by column chromatography to obtain 0.3 g of the following formula (1-11), 0.4 g of (4-3), 0.2 g of (3-10), 0.2 g of (3-11), 0.2 9 of (4-4), 0.19 of (1-12), 0.2 g of (4-5), 0.2 g of (3-12) and 0.2 g of (4-6). Physical properties of these compounds are set forth in Table 6.

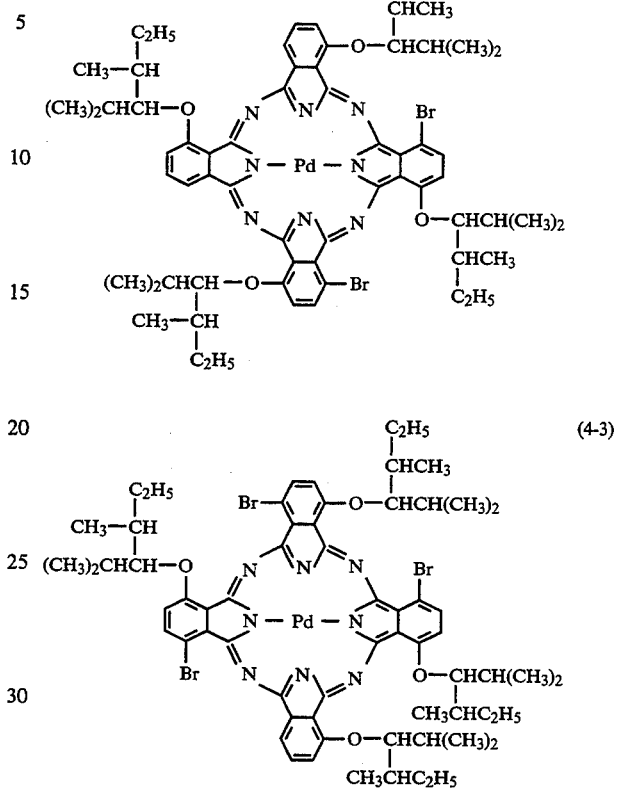

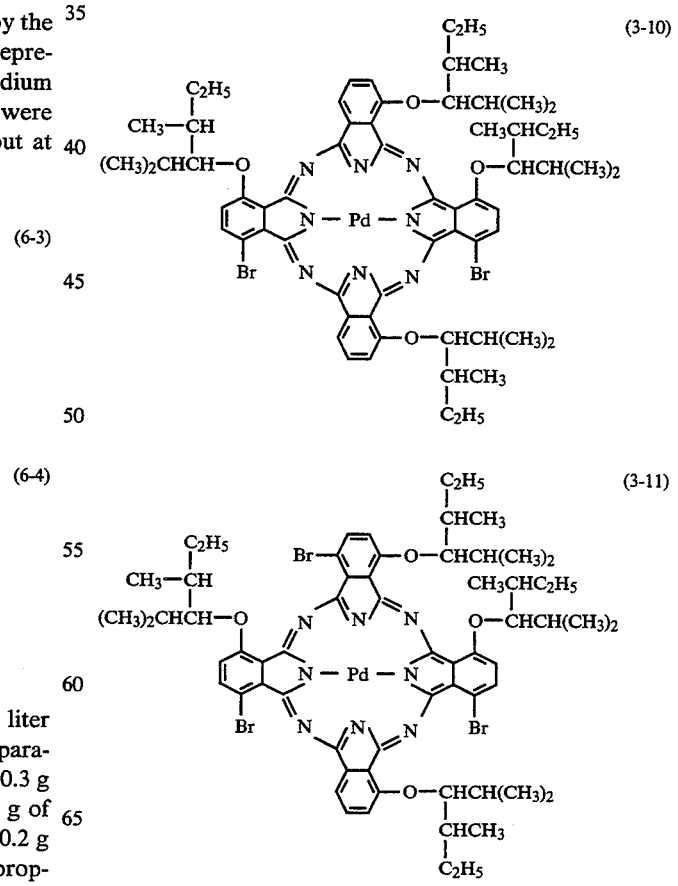

-continued

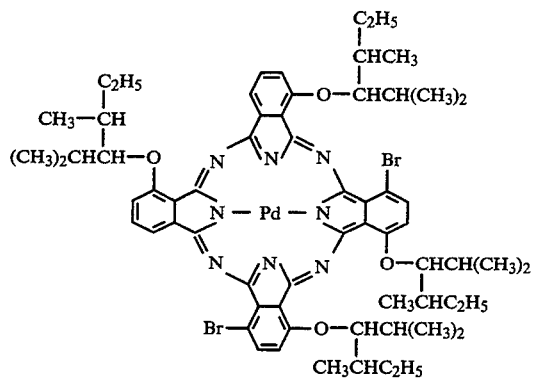
(4-4)

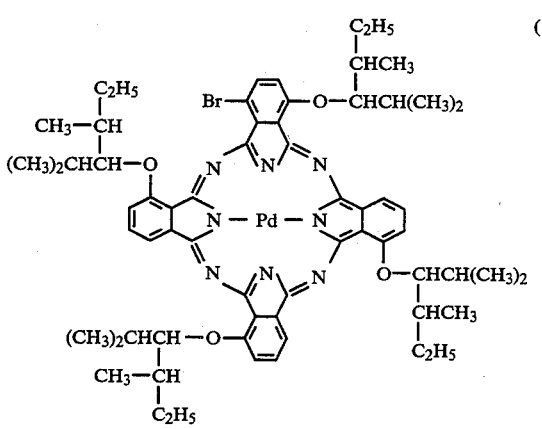
(1-12)

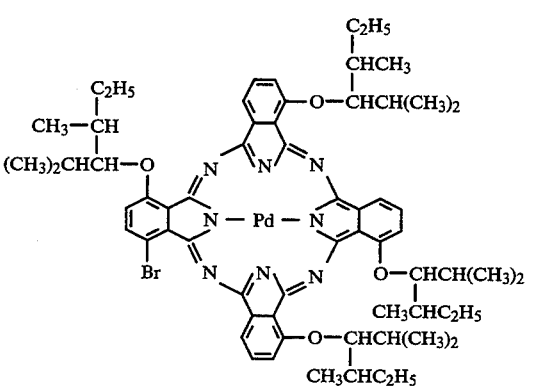
(4-5)

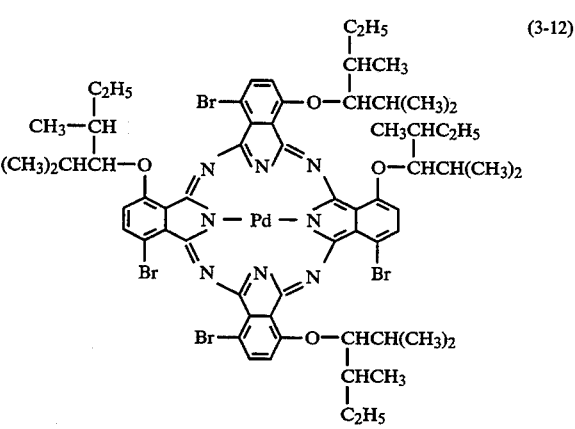
(3-12)

-continued

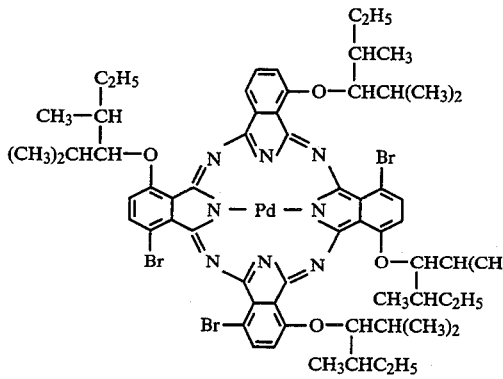
(4-6)

TABLE 6

| Compound No. | $\lambda_{max}$(nm) ($\epsilon_{max} \times 10^{-5}$) | mass (m/e) | Elemental Analysis (C,H,N) Found (Calcd.) |
|---|---|---|---|
| (1-11) | 698 (2.3) | 1289 | 59.11, 5.97, 8.51 (59.61, 6.10, 8.69) |
| (4-3) | 704 (2.2) | 1368 | 55.98, 5.28, 8.32 (56.16, 5.67, 8.19) |
| (3-10) | 700 (2.3) | 1289 | 59.52, 5.96, 8.73 (59.61, 6.10, 8.69) |
| (3-11) | 707 (2.2) | 1368 | 56.01, 5.27, 8.48 (56.16, 5.67, 8.19) |
| (4-4) | 699 (2.2) | 1289 | 59.33, 5.99, 8.45 (59.61, 6.10, 8.69) |
| (1-12) | 694 (2.3) | 1210 | 63.21 6.47, 9.38 (63.49, 6.58, 9.26) |
| (4-5) | 694 (2.2) | 1210 | 63.63, 6.79, 9.15 (63.49, 6.58, 9.26) |
| (3-12) | 715 (2.1) | 1447 | 53.21, 5.47, 7.38 (53.11, 5.29, 7.74) |
| (4-6) | 714 (2.1) | 1447 | 53.02, 5.18, 7.81 (53.11, 5.29, 7.74) |

EXAMPLE 7

Seven grams of diiminoisoindoline represented by the following formula (6-5), 3 g of diiminoisoindoline represented by the following formula (6-6), 2 g of palladium chloride, 4 g of DBU and 300 g of n-octyl alcohol were mutually mixed, and reaction was then carried out at 175° C. for 12 hours.

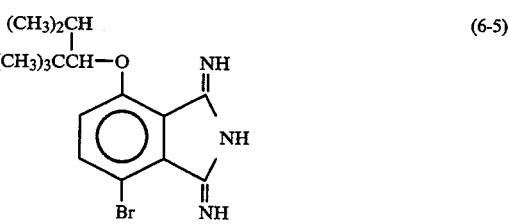
(6-5)

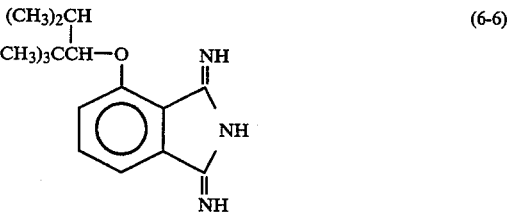
(6-6)

The resultant reaction mixture was poured into 1 liter of methanol, and the precipitated tar was then separated/purified by column chromatography to obtain 0.2 g of the following formula (1-13), 0.4 g of (1-14), 0.1 g of (4-7), 0.1 g of (4-8), 0.2 g of (3-13), 0.1 g of (3-14), 0.2 g of (4-9), 0.2 g of (1-15) and 0.2 g of (3-15). Physical properties of these compounds are set forth in Table 7.
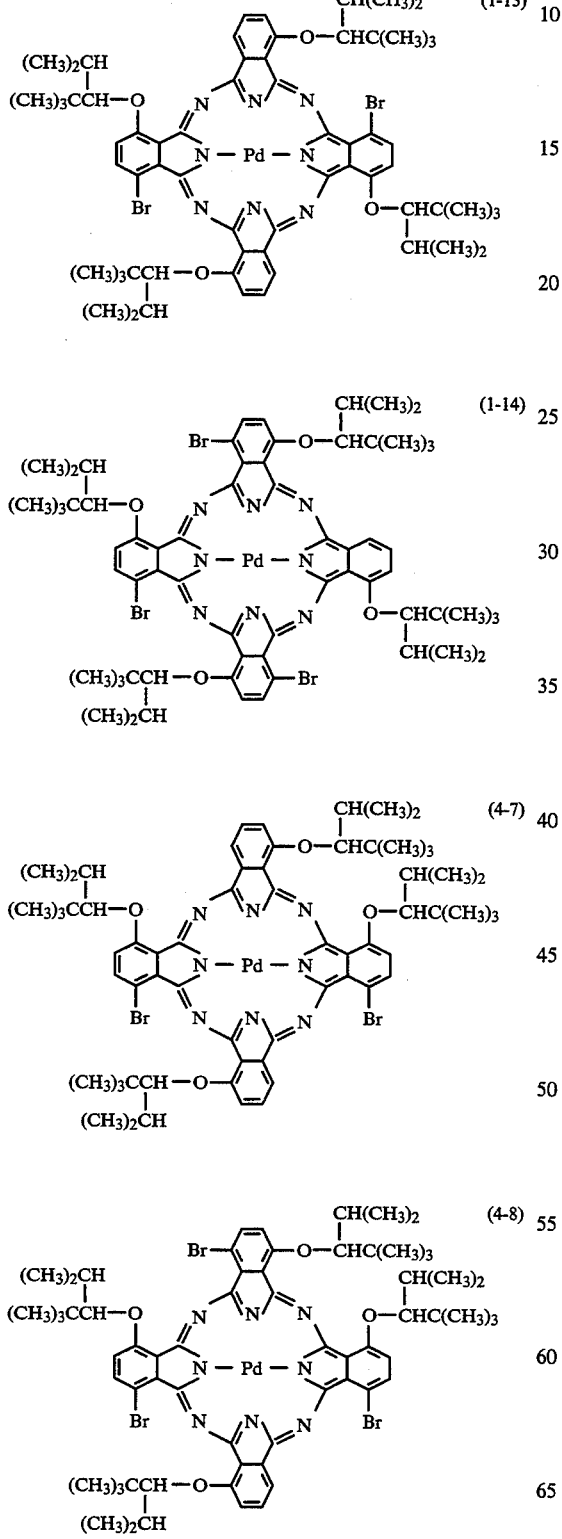
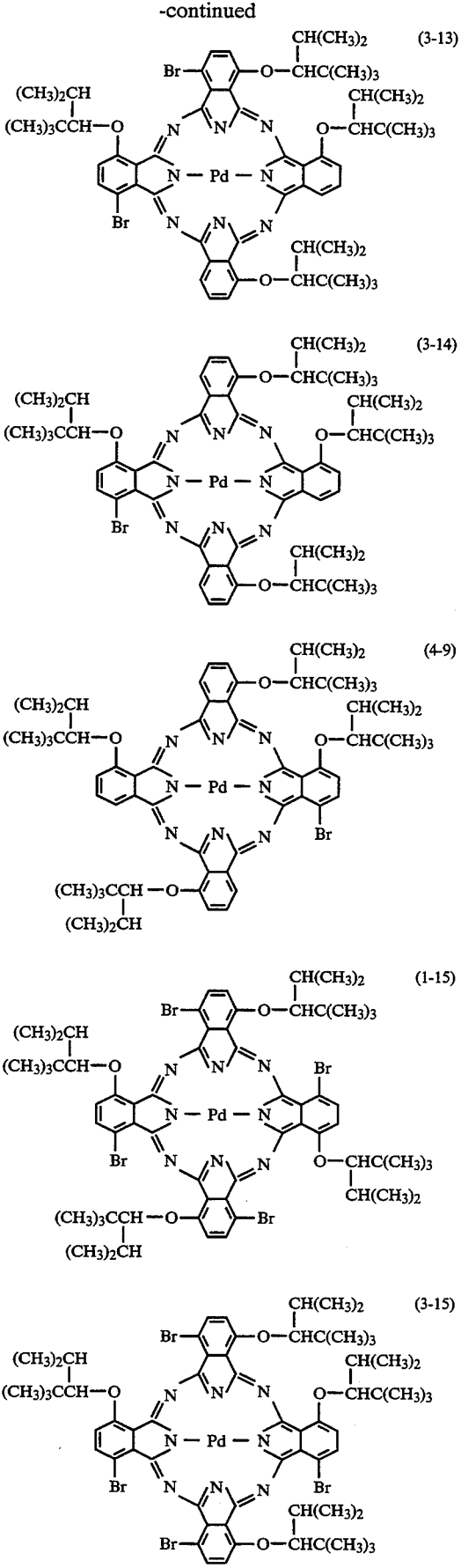

TABLE 7

| Compound No. | $\lambda_{max}$(nm) ($\epsilon_{max} \times 10^{-5}$) | mass (m/e) | Elemental Analysis (C,H,N) Found (Calcd.) |
|---|---|---|---|
| (1-13) | 702 (2.3) | 1289 | 59.11, 5.97, 8.51 (59.61, 6.10, 8.69) |
| (1-14) | 709 (2.2) | 1364 | 55.98, 5.28, 8.32 (56.16, 5.67, 8.19) |
| (4-7) | 705 (2.3) | 1289 | 59.52, 5.96, 8.73 (59.61, 6.10, 8.69) |
| (4-8) | 709 (2.2) | 1391 | 56.01, 5.27, 8.48 (56.16, 5.67, 8.19) |
| (3-13) | 703 (2.2) | 1289 | 59.33, 5.99, 8.45 (59.61, 6.10, 8.69) |
| (3-14) | 697 (2.3) | 1210 | 63.21 6.47, 9.38 (63.49, 6.58, 9.26) |
| (4-9) | 695 (2.2) | 1210 | 63.63, 6.79, 9.15 (63.49, 6.58, 9.26) |
| (1-15) | 718 (2.1) | 1447 | 53.21, 5.47, 7.38 (53.11, 5.29, 7.74) |
| (3-15) | 719 (2.1) | 1447 | 53.02, 5.18, 7.81 (53.11, 5.29, 7.74) |

EXAMPLE 8

Thirty grams of a compound represented by the above-mentioned formula (1-3) were dissolved in 1 liter of dimethylcyclohexane, and the resultant solution was then applied as thick as 120 nm on a polycarbonate substrate having grooves by a spin coating method. Next, gold was sputtered so as to have a thickness of 100 nm. Successively, an ultraviolet-curing resin was subjected to spin coating and then cured with ultraviolet rays. Its thickness was 6 μm. When the thus prepared optical recording medium for CD-WO was used to carry out recording at a linear velocity of 1.4 m/sec at an optimum power (8 mW) by the use of a laser beam of 780 nm, a record of 60 dB was obtained and recording properties ( the symmetry, jitter and cross talk of signals) were also excellent. Reflectance was 69%. The refractive index of this recording layer was 2.12 at 780 nm.

EXAMPLES 9 TO 16

The same procedure as in Example 8 was effected using the compounds obtained the preceding examples, to prepare optical recording media for CD-WO. For the thus obtained optical recording media, optimum power, recording sensitivity, symmetry, jitter and cross talk were inspected. The results are set forth in Table 8. Incidentally, reflectances all were between 65 and 72%.

TABLE 8

| Example | Compound | Optimum Power (mW) | Record (dB) | Symmetry | Jitter | Cross Talk |
|---|---|---|---|---|---|---|
| 8 | 2-1 | 7.8 | 62 | O | O | O |
| 9 | 3-2 | 8.1 | 63 | O | O | O |
| 10 | 3-4 | 6.7 | 61 | O | O | O |
| 11 | 1-9 | 7.3 | 60 | O | O | O |
| 12 | 4-3 | 7.1 | 62 | O | O | O |
| 13 | 3-11 | 7.3 | 61 | O | O | O |
| 14 | 4-5 | 7.5 | 61 | O | O | O |
| 15 | 3-14 | 6.9 | 61 | O | O | O |

COMPARATIVE EXAMPLES 1 TO 6

The same procedure as in Example 7 was effected using compounds (I-98) to (I-103) exemplified in Japanese Patent Application Laid-Open No. 62878/1991 to prepare optical recording media for CD-WO. Recording properties of these media are set forth in Table 9. In this connection, structures of the exemplified compounds (I-98) to (I-103) are as follows:

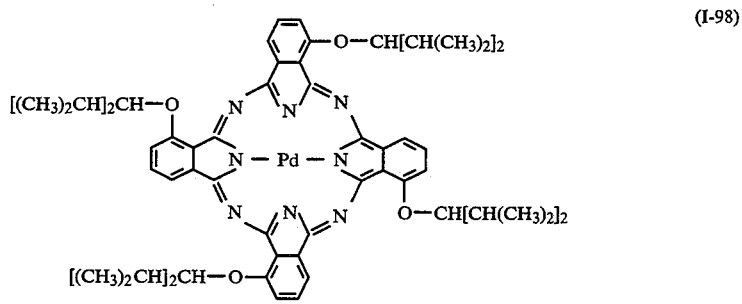

(I-98)

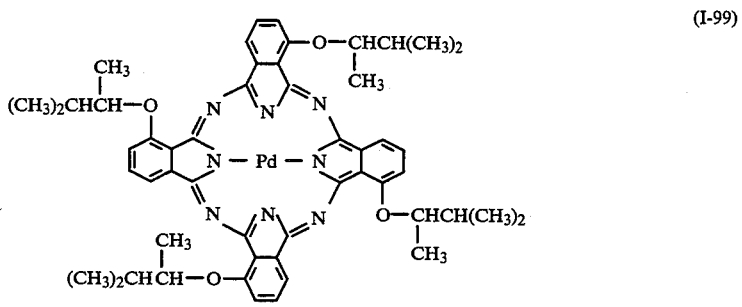

(I-99)

-continued

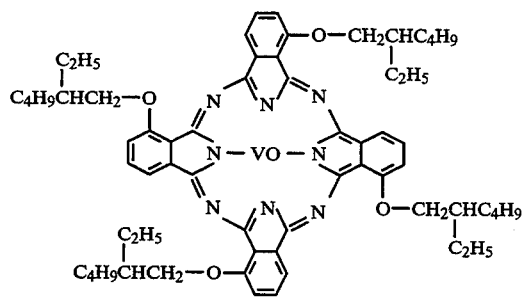

(I-100)

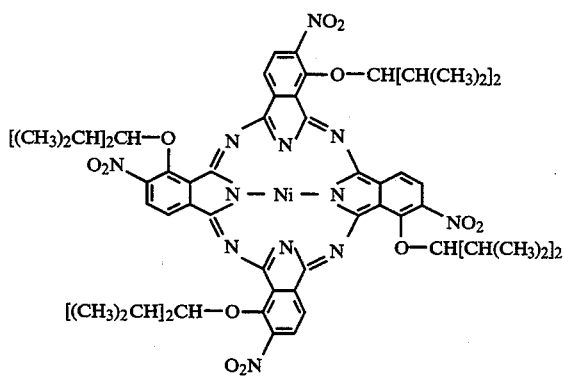

(I-101)

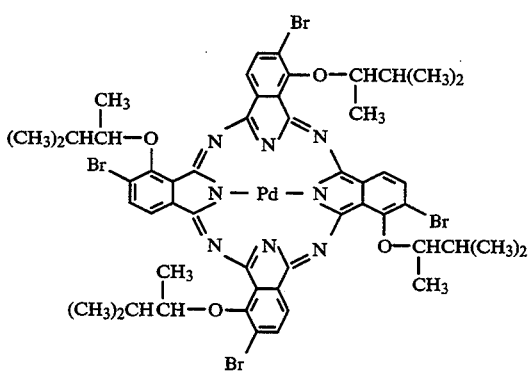

(I-102)

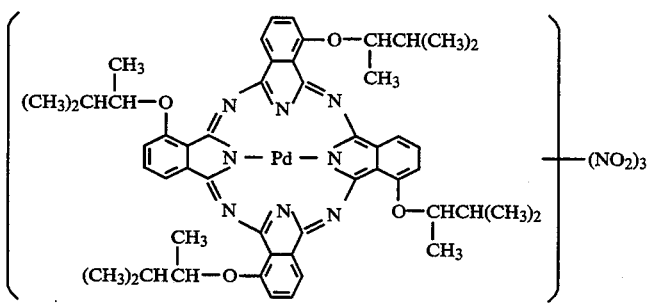

(I-103)

TABLE 9

| Comparative Example | Compound | Optimum Power (mW) | Record (dB) | Symmetry | Jitter | Cross Talk |
|---|---|---|---|---|---|---|
| 1 | I-98 | 8.8 | 55 | X | X | X |
| 2 | I-99 | 8.7 | 52 | X | X | X |
| 3 | I-100 | 8.1 | 43 | X | X | X |
| 4 | I-101 | 7.3 | 55 | X | X | X |
| 5 | I-102 | 9.1 | 52 | X | X | X |
| 6 | I-103 | 9.4 | 53 | X | X | X |

EXAMPLE 17

Fifteen grams of a mixture of palladium tetraα-(1,3-dimethylbutyloxy)phthalocyanines in which the ratio of the following formulae (10-1), (11-1), (9-1) and (12-1) was 20:30:30:20 were added to a mixed solvent of 50 g (38 ml) of dichloromethane, 50 g (76 ml) of n-hexane and 100 g (100 ml) of water.

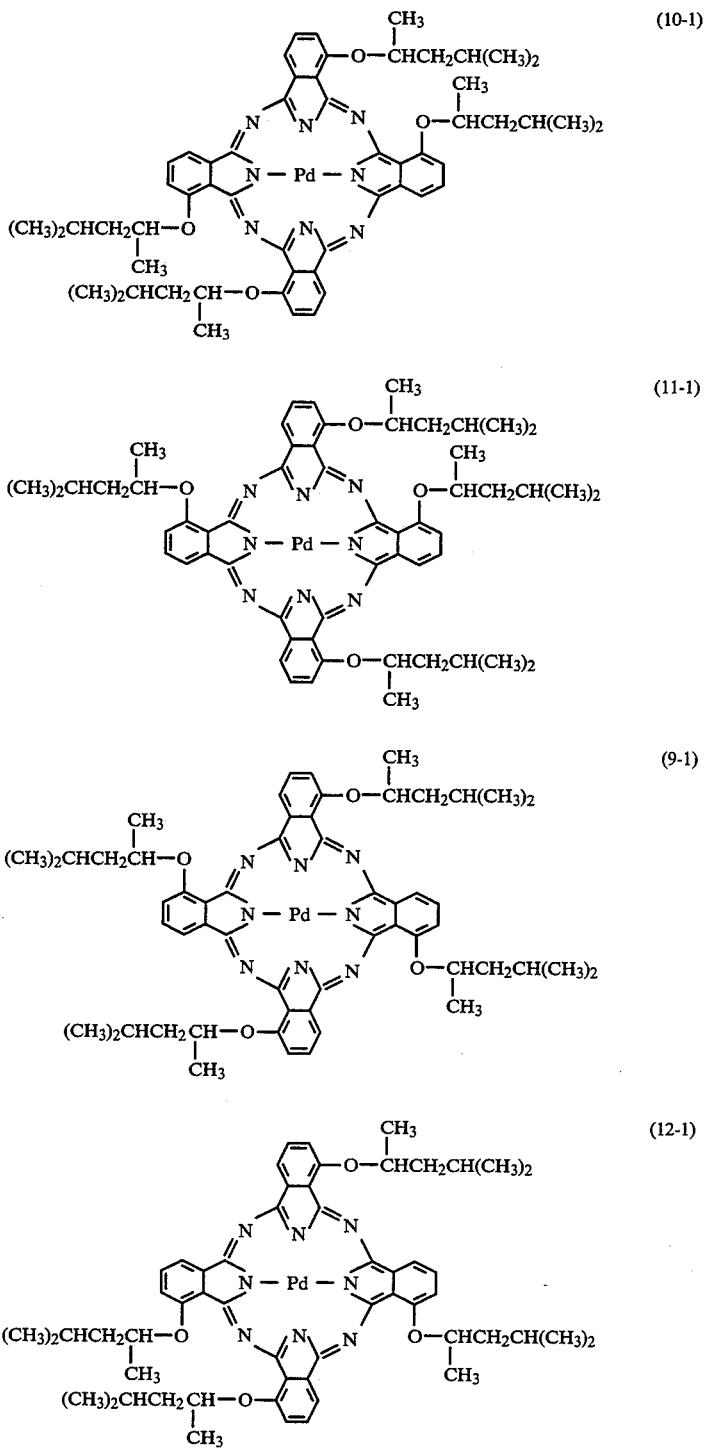

Furthermore, 9.5 g of bromine were added thereto, and reaction was then carried out at 40° C. for 2 hours. After cooling to 20° C., 50 g of toluene were added, followed by separation. Successively, the resultant organic solvent layer was washed with 100 g of a 10% aqueous sodium hydrogensulfite solution and 100 g of a 5% aqueous sodium hydrogencarbonate solution. The organic solvent was distilled off, and separation was then carried out by toluene-silicia gel chromatography to obtain 16 g of a mixture of brominated phthalocyanines represented by the following formulae (2-3), (3-16), (1-16) and (4-10). The maximum absorption wave length $\lambda_{max}$ of the mixture was 700 nm and $\epsilon_{max}$ was $1.6 \times 10^5$ g$^{-1}$cm$^2$.

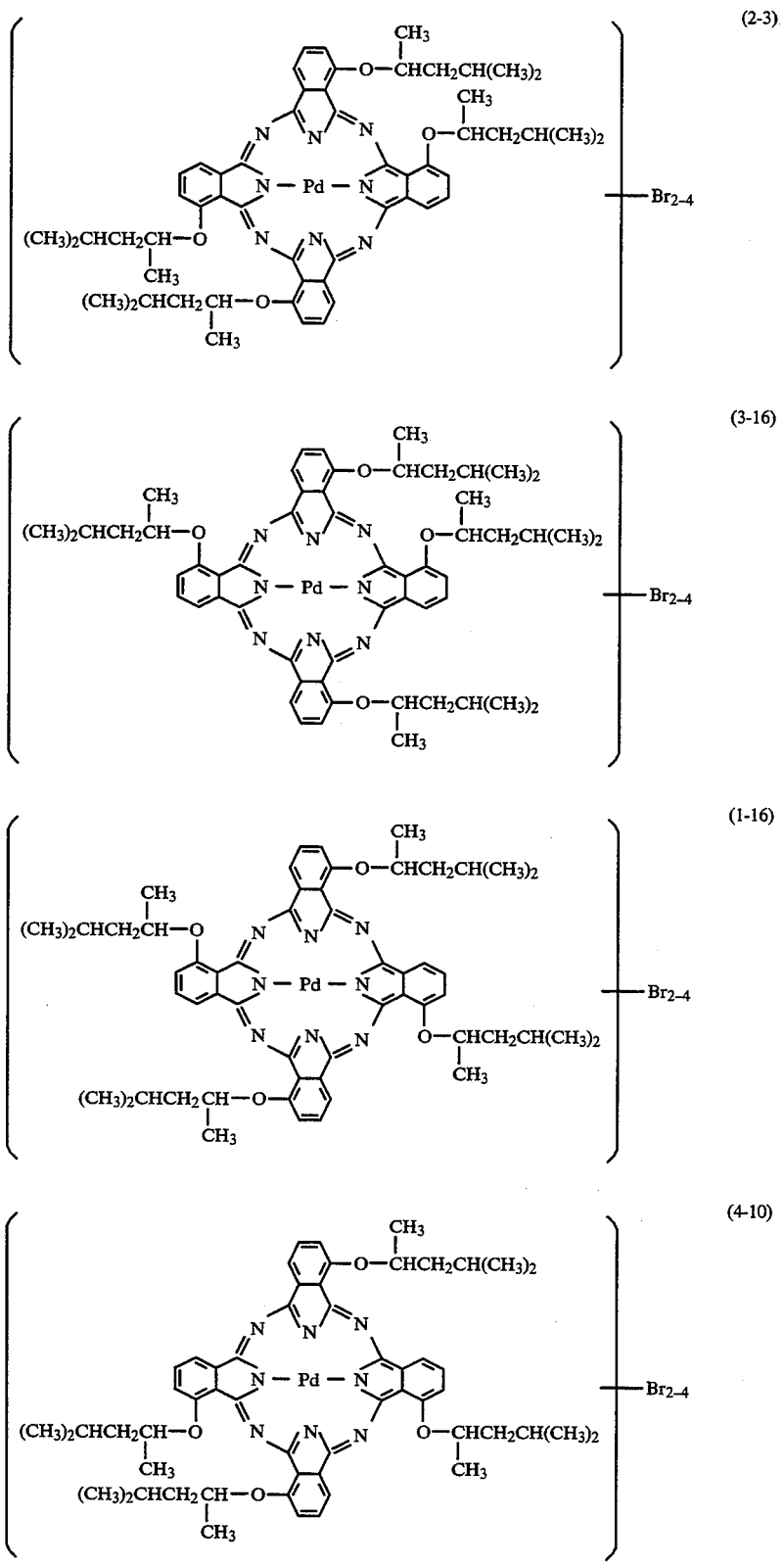
EXAMPLE 18
Fifteen grams (13.25 mmol) of a mixture of palladium tetraα-(1-iso-propyl-3-methylbutyloxy)phthalocyanines in which ratio of the following formulae (10-2), (11-2), (9-2) and (12-2) was 20:30:30:20 were added to a mixed solvent of 50 g (56 ml) of tetrahydrofuran, 50 g (76 ml) of n-hexane and 100 g (100 ml) of water.

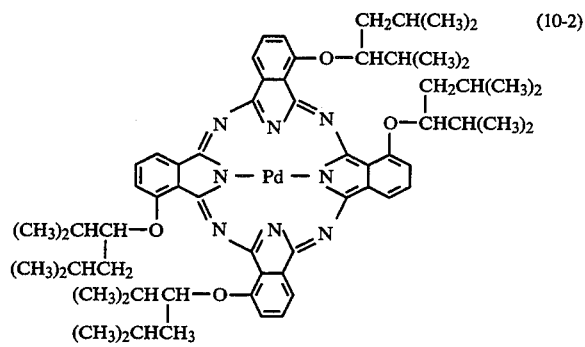 (10-2)

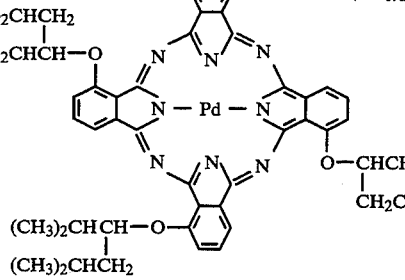 (9-2)

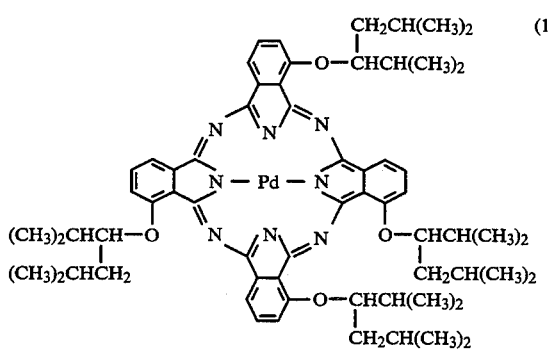 (11-2)

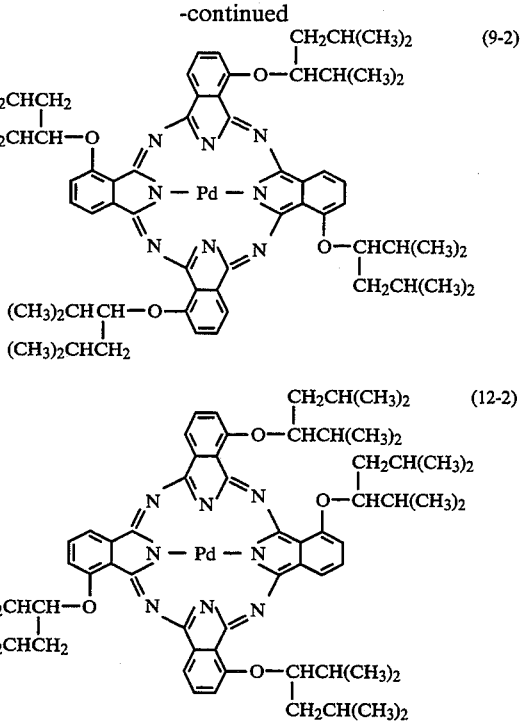 (12-2)

Furthermore, 15 g (93.86 mmol) of bromine were added thereto, and reaction was then carried out at 40° C. for 2 hours. After cooling to 20° C., 50 g of toluene were added, followed by separation. Successively, the resultant organic solvent layer was washed with 100 g of a 10% aqueous sodium hydrogensulfite solution and 100 g of a 5% aqueous sodium hydrogencarbonate solution. The organic solvent was distilled off, and separation was then carried out by toluene-silica gel chromatography to obtain 15 g of a mixture of brominated phthalocyanines represented by the following formulae (2-4), (3-17), (1-17) and (4-11).

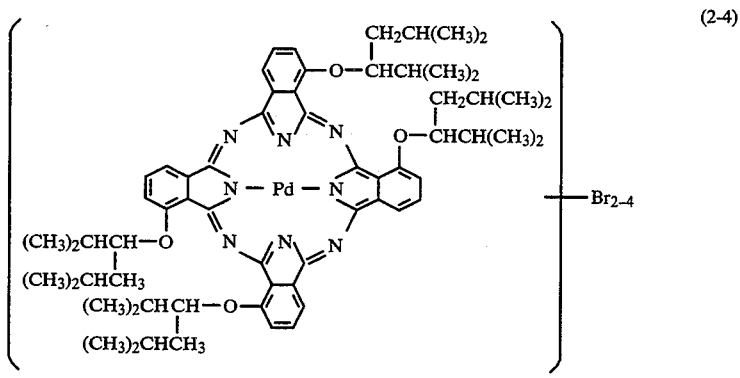 (2-4)

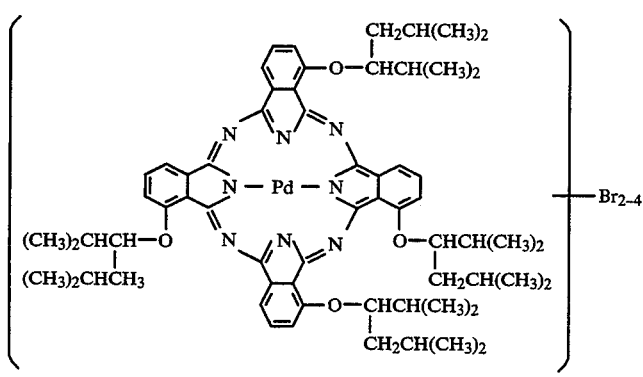

(3-17)

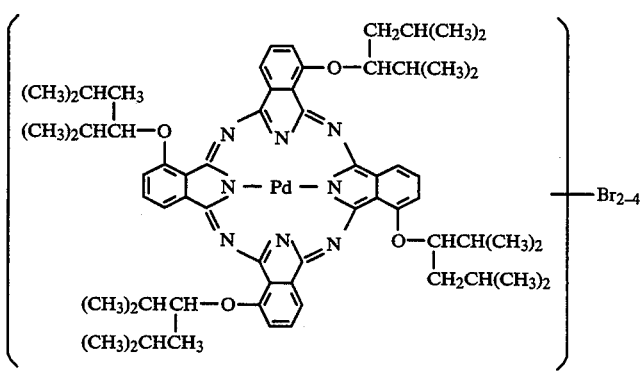

(1-17)

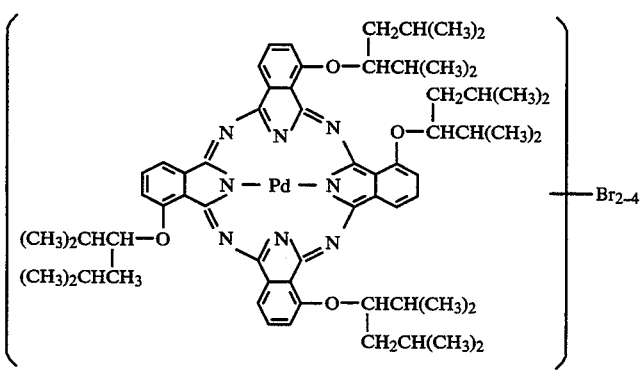

(4-11)

The liquid chromatogram of this mixture is shown in FIG. 1. A retention time and concentration of each peak are set forth in Table 10. The maximum absorption wave length $\lambda_{max}$ of the mixture was 706 nm and $\epsilon_{max}$ was $1.4 \times 10^5 \text{ g}^{-1}\text{cm}^2$, and a melting point was 149°–72° C.

TABLE 10

| Peak No. | Retention Time | Concentration |
|---|---|---|
| 1 | 5.892 | 0.004 |
| 2 | 16.145 | 35.3123 |
| 3 | 17.7 | 6.9134 |
| 4 | 18.345 | 3.7454 |
| 5 | 19.048 | 8.3346 |
| 6 | 19.972 | 13.2588 |
| 7 | 20.715 | 3.1194 |
| 8 | 21.613 | 2.224 |
| 9 | 22.55 | 8.873 |
| 10 | 24.283 | 0.9399 |
| 11 | 25.573 | 4.6923 |
| 12 | 26.915 | 6.4882 |
| 13 | 28.083 | 3.1528 |
| 14 | 29.717 | 1.5366 |
| 15 | 31.382 | 1.4054 |

TABLE 10-continued

| Peak No. | Retention Time | Concentration |
|---|---|---|
| Total | | 100 |

EXAMPLE 19

Fifty grams (46.48 mmol) of a mixture of palladium tetra$\alpha$-(1-iso-propyl-2-methylpropyloxy)phthalocyanines in which the ratio of the following formulae (10-3), (11-3), (9-3) and (4-3) was 2:80:15:3

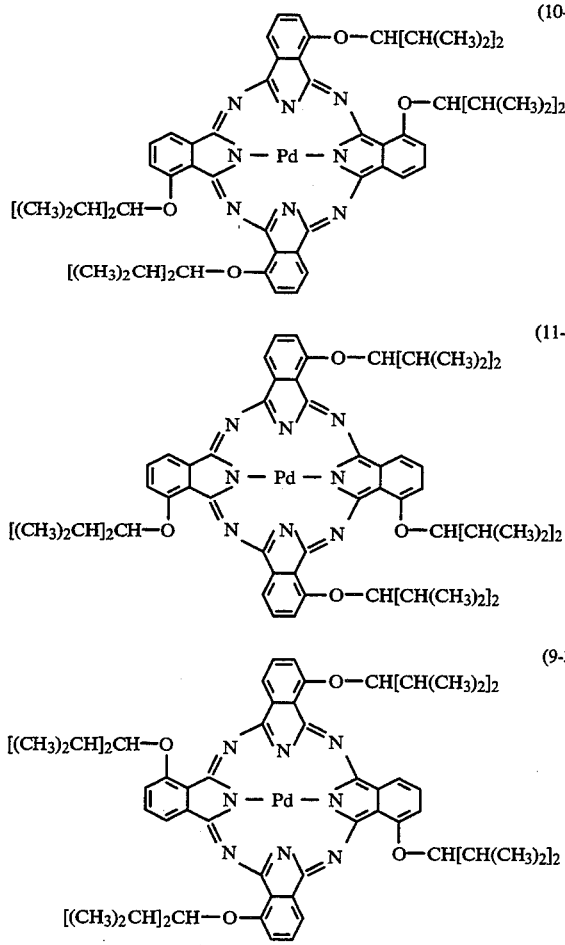

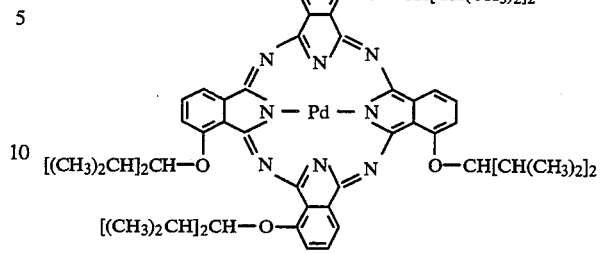

were dissolved in 300 g (208 ml) of 1,1,2-trichloroethane, and 100 g (100 ml) of water were added thereto. Next, a mixture of 22.7 g (142.03 mmol) of bromine and 63 g (44 ml) of 1,1,2-trichloroethane was added dropwise at 50° to 55° C., and reaction was then carried out at 55° to 60° C. for 1 hour. Afterward, 50 g of a 15% aqueous sodium hydrogensulfite solution were added, followed by washing. The resultant organic layer was added dropwise to 800 g of methanol, and the precipitated crystals were filtered, thereby obtaining 59.8 g of a mixture of brominated phthalocyanines represented by the formulae (2-5), (3-18), (1-18) and (4-12).

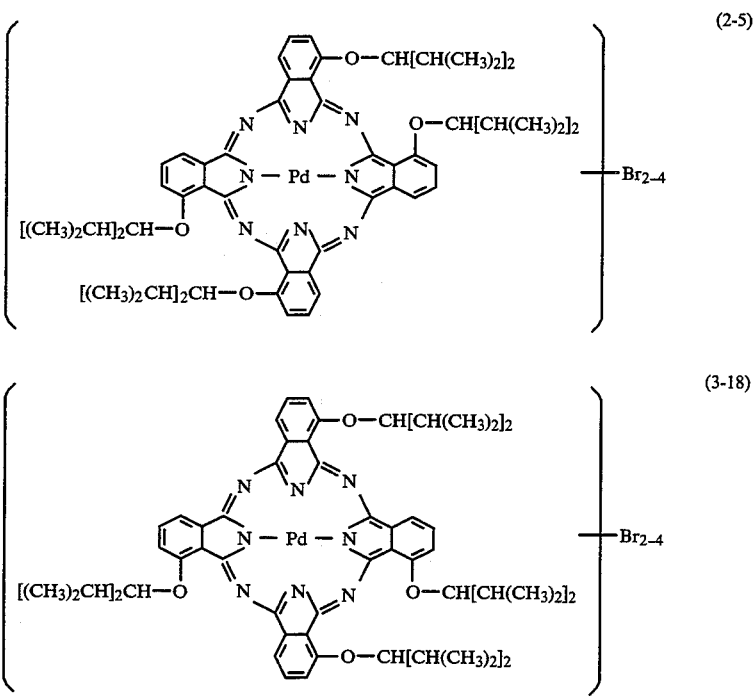

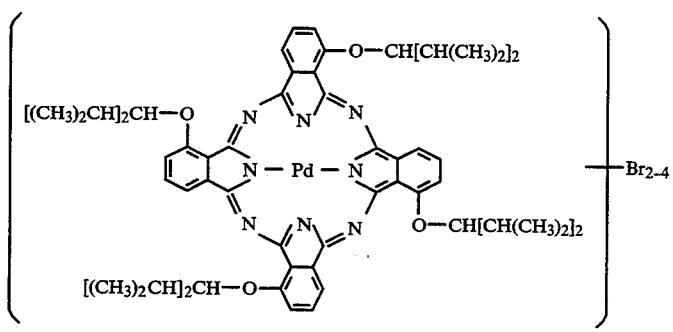

(1-18)

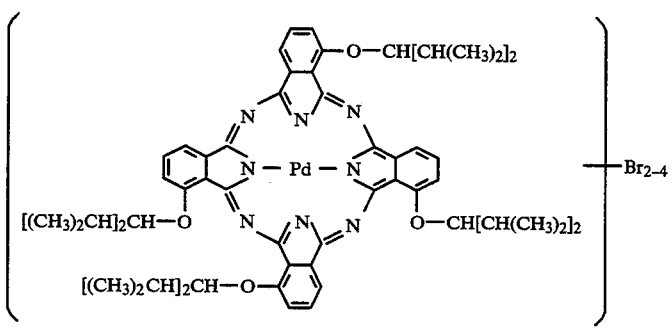

(4-12)

Figure 2:
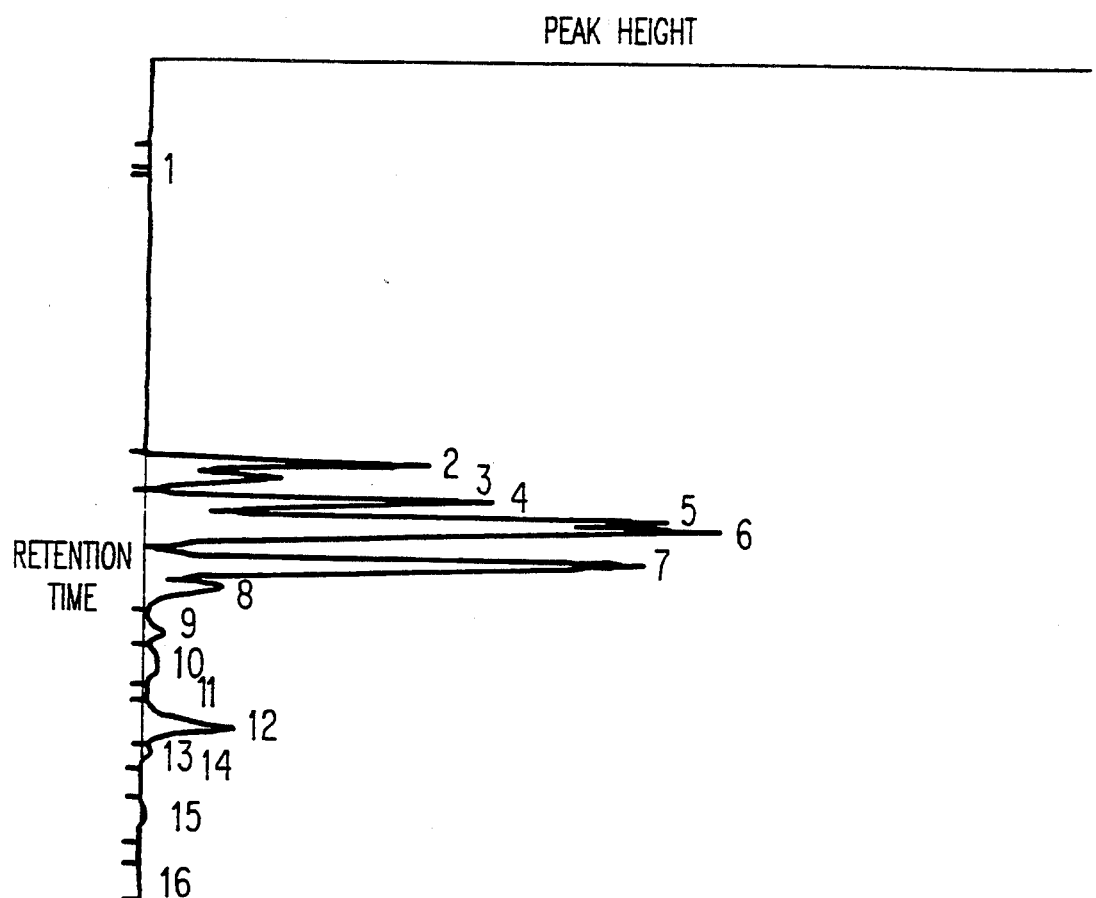
FIG. 2 is a liquid chromatogram of a brominated alkoxyphthalocynine mixture obtained in Example 19.

The liquid chromatogram of the mixture is shown in FIG. 2. A retention time and concentration of each peak are set forth in Table 11. The maximum absorption wave length $\lambda_{max}$ of the mixture was 706 nm, $\epsilon_{max}$ was $1.6 \times 10^5$ g$^{-1}$cm$^2$, and a melting point was 215°–45° C.

TABLE 11

| Peak No. | Retention Time | Concentration |
|---|---|---|
| 1 | 7.408 | 0.0137 |
| 2 | 23.008 | 8.5536 |
| 3 | 23.722 | 4.2271 |
| 4 | 24.992 | 12.3603 |
| 5 | 26.045 | 17.6083 |
| 6 | 26.553 | 19.6252 |
| 7 | 28.41 | 22.9657 |
| 8 | 29.59 | 4.299 |
| 9 | 32.058 | 1.4879 |
| 10 | 33.923 | 1.719 |
| 11 | 35.255 | 0.3461 |
| 12 | 37.122 | 5.5754 |
| 13 | 38.325 | 0.5243 |
| 14 | 39.858 | 0.234 |
| 15 | 41.59 | 0.3649 |
| 16 | 45.258 | 0.0957 |
| Total | | 100 |

EXAMPLE 20

Fifteen grams (13.25 mmol) of a mixture of palladium tetraα-(2-ethylhexyloxy)phthalocyanines in which the ratio of the following formulae (10-4), (11-4), (9-4) and (12-4) was 10:40:30:20

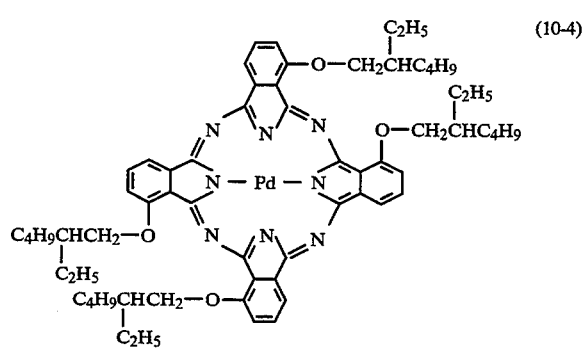

(10-4)

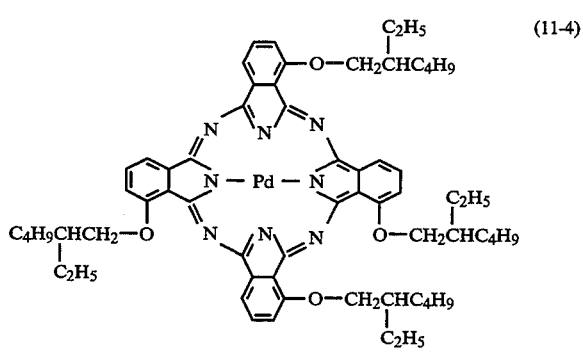

(11-4)

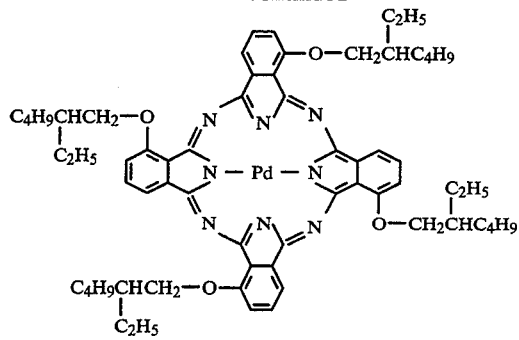

(9-4)

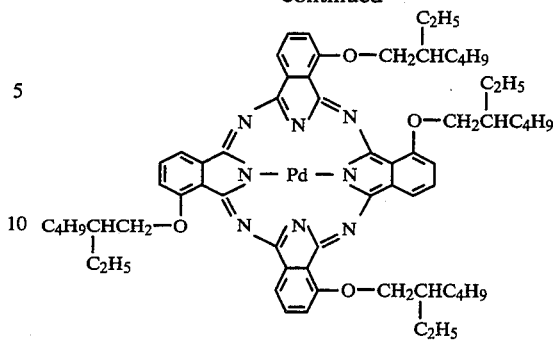

(12-4)

were added to a mixed solvent of 50 g (31 ml) of 1,1,2,2-tetrachloroethane, 50 g (63 ml) of ethylcyclohexane and 100 g (100 ml) of water. Next, a mixture of 6.2 g (39.42 mmol) of bromine was added, and reaction was then carried out at 60° C. for 2 hours. After cooling to 20° C., 50 g of toluene were added, followed by separation. Successively, the resultant organic solvent layer was washed with 100 g of a 10% aqueous sodium hydrogensulfite solution and 100 g of a 5% aqueous sodium hydrogencarbonate solution. The organic solvent was distilled off, and separation was then carried out by toluene-silica gel chromatography to obtain 16 g of a mixture of brominated phthalocyanines represented by the following formulae (2-6), (3-19), (1-19) and (4-13).

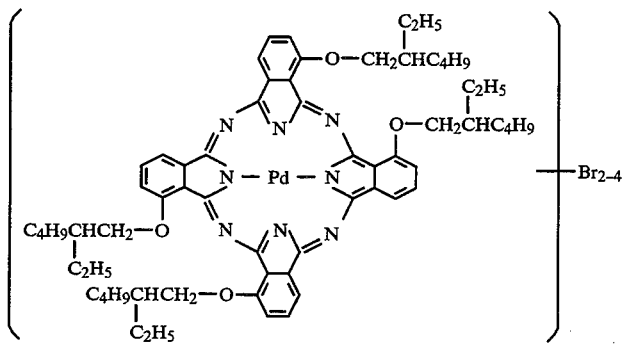

(2-6)

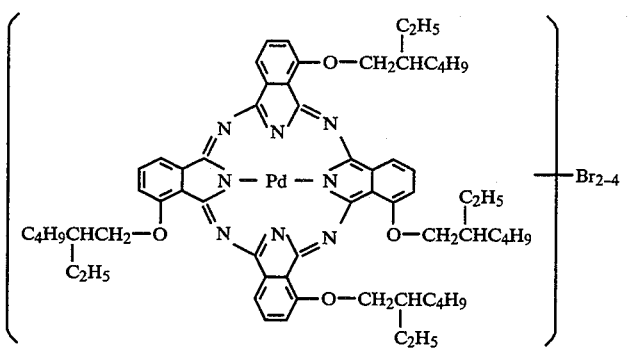

(3-19)

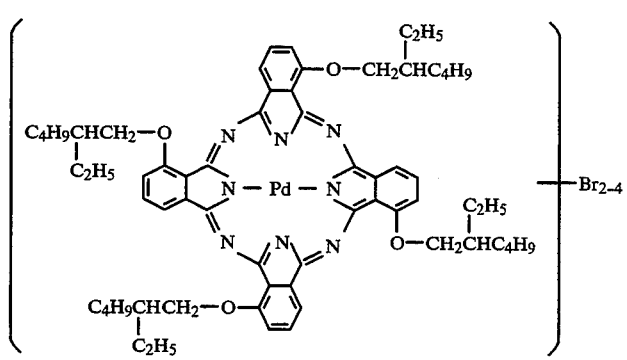
(1-19)

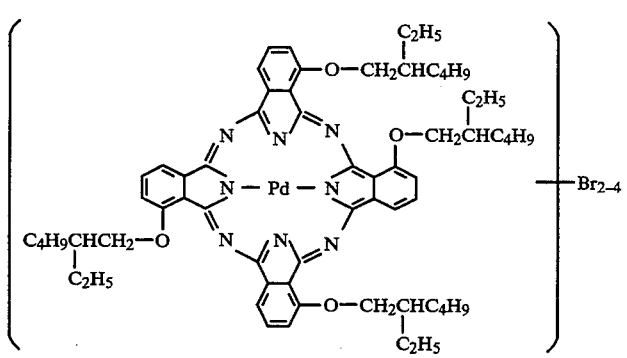
(4-13)

Figure 3:
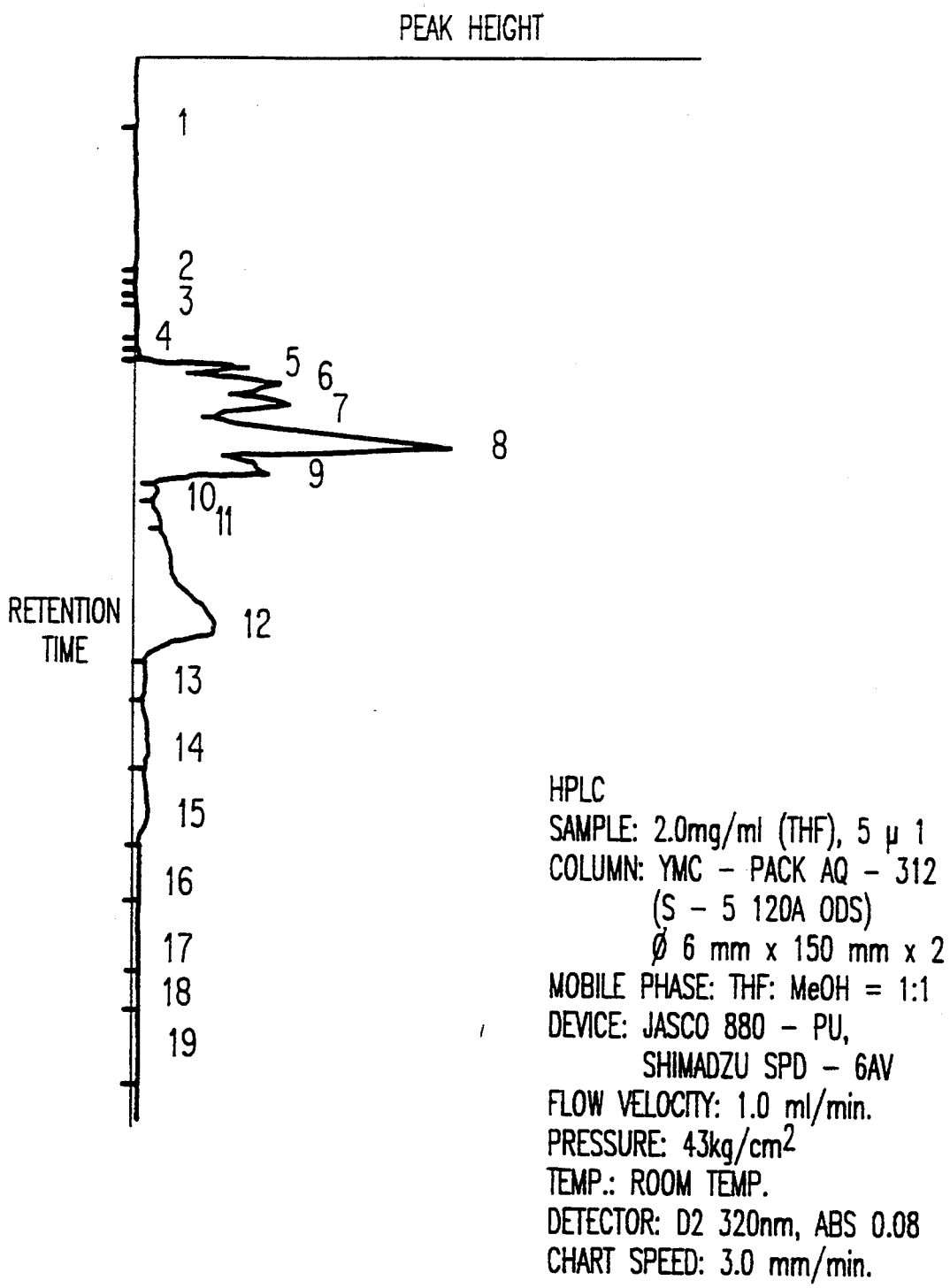
FIG. 3 is a liquid chromatogram of a brominated alkoxyphthalocynine mixture obtained in Example 20.

The liquid chromatogram of the mixture is shown in FIG. 3. A retention time and concentration of each peak are set forth in Table 12. The maximum absorption wave length $\lambda_{max}$ of the mixture was 695 nm, $\epsilon_{max}$ was $2.0\times10^5$ g$^{-1}$cm$^2$, and a melting point was 108°–50° C.

TABLE 12

| Peak No. | Retention Time | Concentration |
|---|---|---|
| 1 | 5.892 | 0.0031 |
| 2 | 14.158 | 0.0312 |
| 3 | 15.487 | 0.0261 |
| 4 | 18.673 | 0.0682 |
| 5 | 19.408 | 3.5649 |
| 6 | 20.422 | 9.9876 |
| 7 | 21.545 | 11.2846 |
| 8 | 24.07 | 28.6963 |
| 9 | 25.39 | 10.4533 |
| 10 | 26.208 | 1.3327 |
| 11 | 27.942 | 2.393 |
| 12 | 33.915 | 24.1779 |
| 13 | 36.875 | 1.2773 |
| 14 | 40.742 | 2.7678 |
| 15 | 44.742 | 2.54 |
| 16 | 48.342 | 0.5219 |
| 17 | 52.07 | 0.5587 |
| 18 | 54.602 | 0.2424 |
| 19 | 56.192 | 0.073 |
| Total | | 100 |

EXAMPLE 21

Ten grams (8.84 mmol) of a mixture of palladium tetraα-(1-iso-propyl-2-methylbutyloxy)phthalocyanines in which the ratio of the following formulae (10-5), (11-5), (9-5) and (12-5) was 10:55:30:5

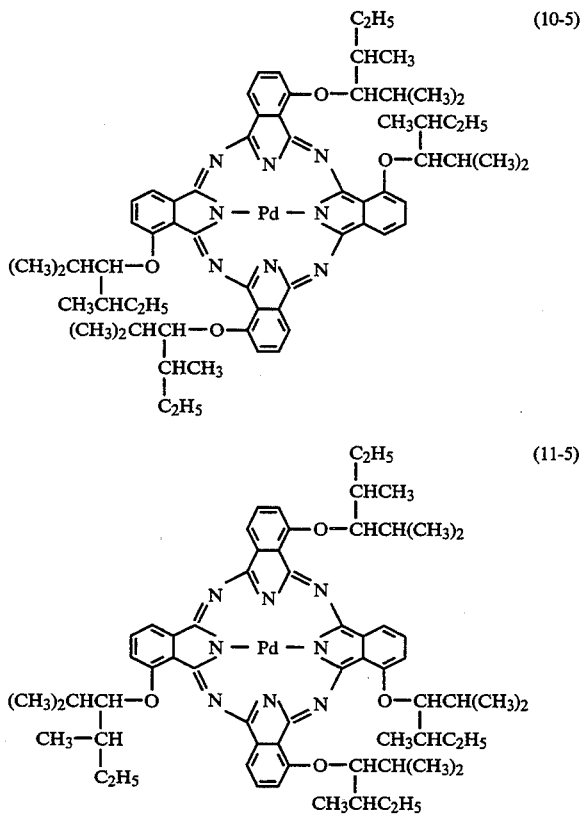

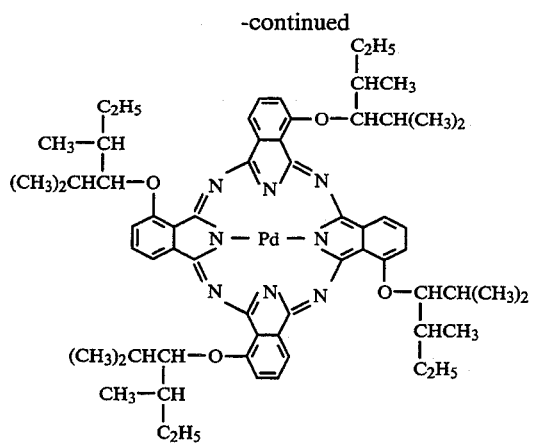

(9-5)

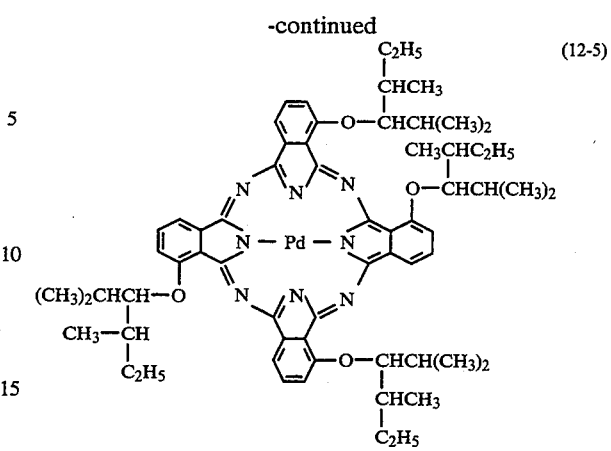

(12-5)

were dissolved in 48 g (30 ml) of 1,1,2,2-tetrachloroethane, and 20 g (20 ml) of water were added thereto. Next, a mixture of 5.51 g (34.48 mmol) of bromine and 16 g (10 ml) of 1,1,2,2-tetrachloroethane was added dropwise at 50° to 55° C., and reaction was then carried out at 55° to 60° C. for 1 hour. Afterward, 25 g of a 10% aqueous sodium hydrogensulfite solution were added, followed by washing. The resultant organic layer was added dropwise to 158 g of methanol, and the precipitated crystals were filtered, thereby obtaining 12.5 g of a mixture of a brominated phthalocyanines represented by the formulae (2-7), (3-20), (1-20) and (4-14).

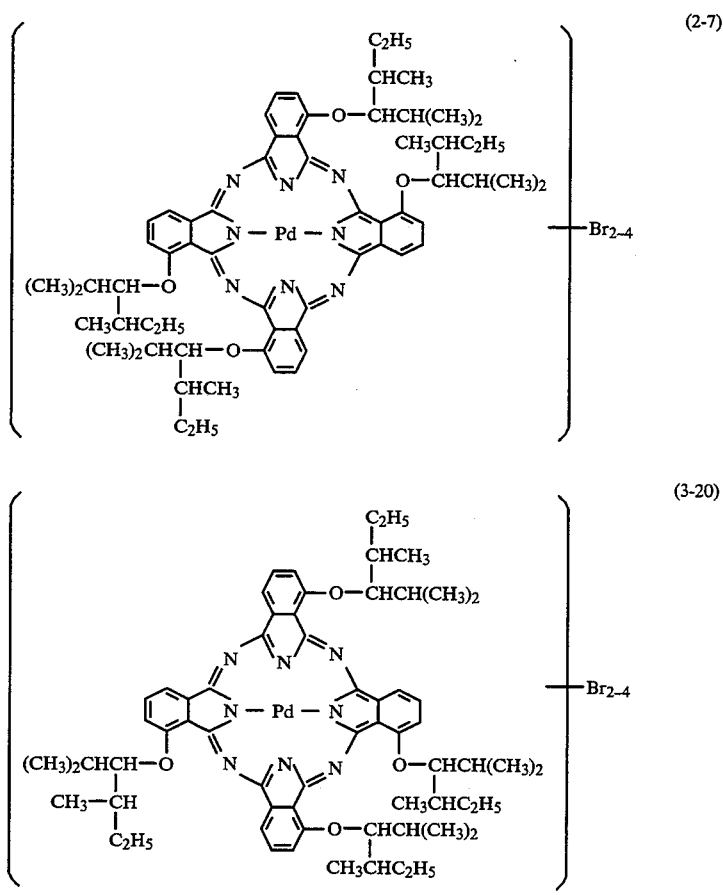

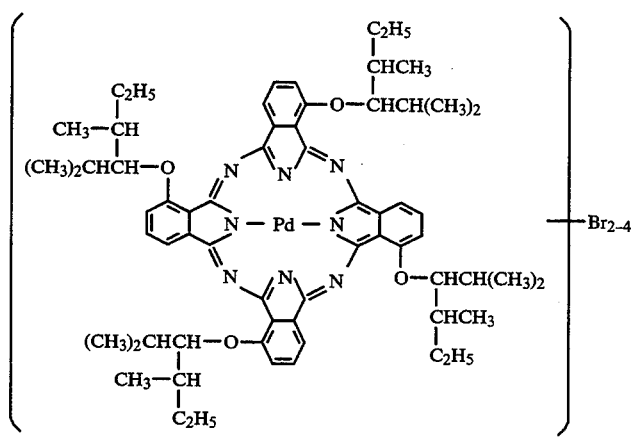

(1-20)

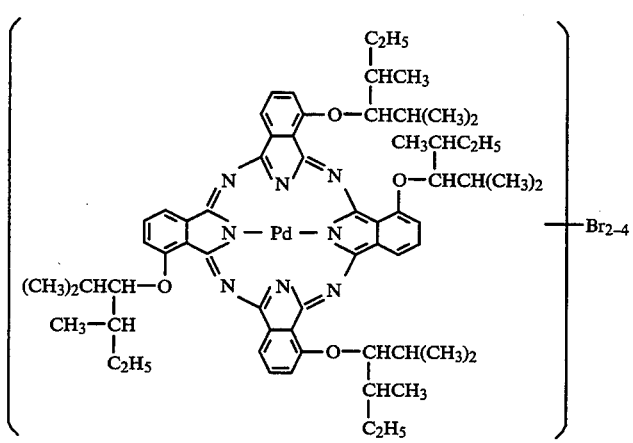

(4-14)

Figure 4:
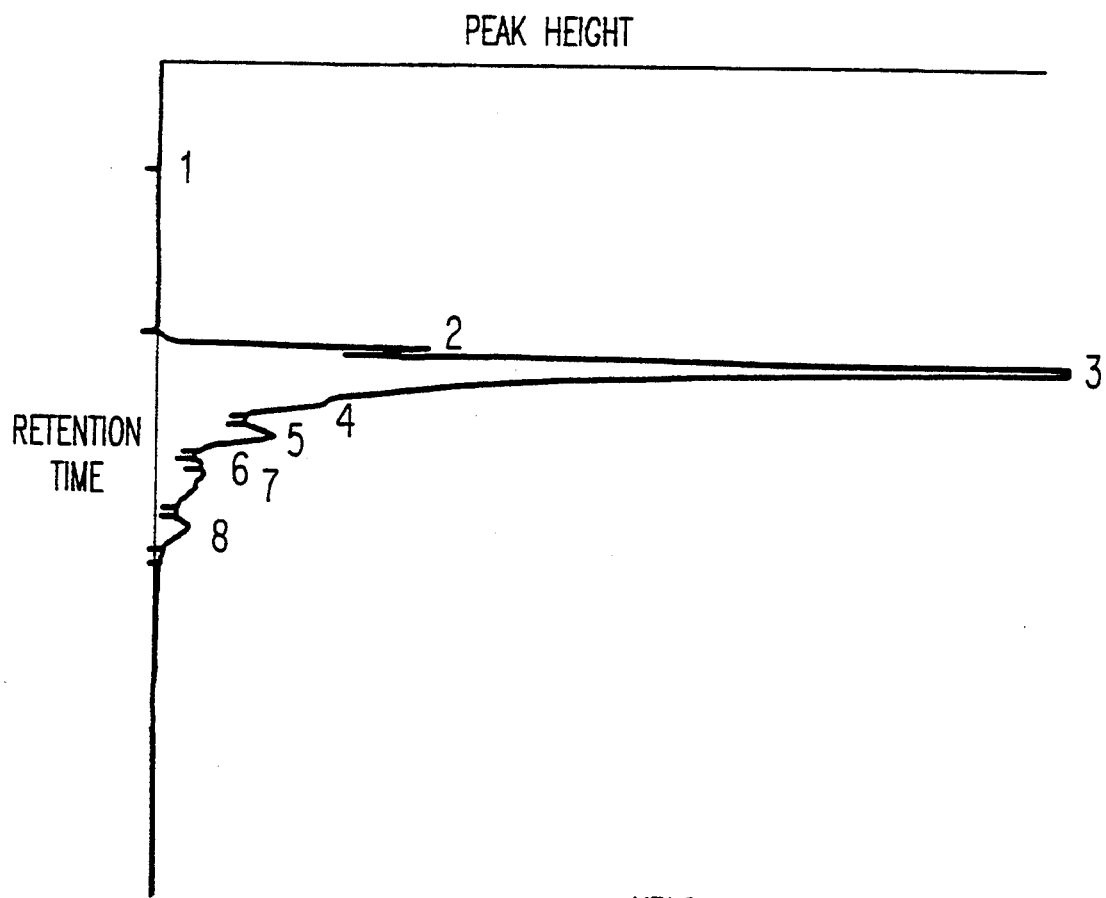
FIG. 4 is a liquid chromatogram of a brominated alkoxyphthalocynine mixture obtained in Example 21.

The liquid chromatogram of the mixture is shown in FIG. 4. A retention time and concentration of each peak are set forth in Table 13. The maximum absorption wave length $\lambda_{max}$ of the mixture was 706 nm, $\epsilon_{max}$ was $1.4\times10^5$ g$^{-1}$cm$^2$, and a melting point was 201°–28° C.

TABLE 13

| Peak No. | Retention Time | Concentration |
|---|---|---|
| 1 | 5.9 | 0.0037 |
| 2 | 14.82 | 6.5073 |
| 3 | 15.96 | 89.0199 |
| 4 | 18.242 | 0.1087 |
| 5 | 19.108 | 2.2992 |
| 6 | 20.542 | 0.2509 |
| 7 | 21.073 | 0.8823 |
| 8 | 23.572 | 0.928 |
| Total | | 100 |

EXAMPLE 22

Ten grams (8.84 mmol) of a mixture of palladium tetraα-(1-tert-butyl-2-methylpropyloxy)phthalocyanines in which the ratio of the following formulae (10-6), (11-6), (9-6) and (12-6) was 5:45:30:20:

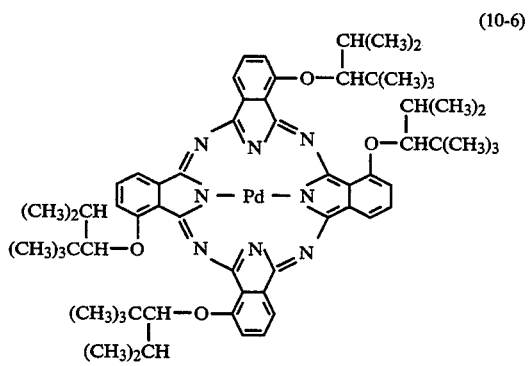

(10-6)

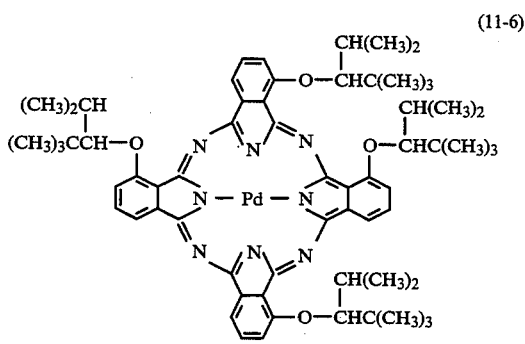

(11-6)

-continued

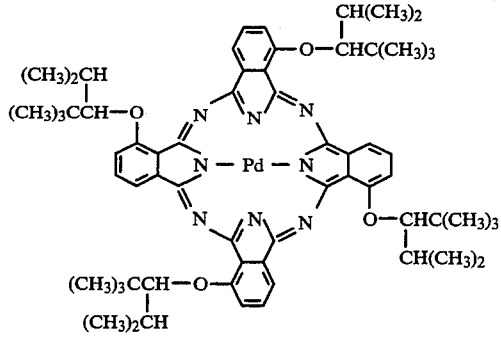
(9-6)

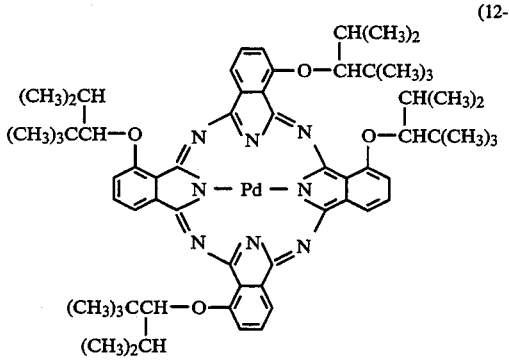
(12-6)

were dissolved in 56 g (39 ml) of 1,1,2-trichloroethane, and 20 g (20ml) of water were added thereto. Next, a mixture of 4.94 g (30.91 mmol) of bromine and 12 g (8 ml) of 1,1,2-trichloroethane was added dropwise at 50° to 55° C., and reaction was then carried out at 55° to 60° C. for 1 hour. Afterward, 20 g of a 10% aqueous sodium hydrogensulfite solution were added, followed by washing. The resultant organic layer was added dropwise to 135 g of methanol, and the precipitated crystals were filtered, thereby obtaining 12 g of a mixture of brominated phthalocyanines represented by the formula (2-8), (3-21), (1-21) and (4-15).

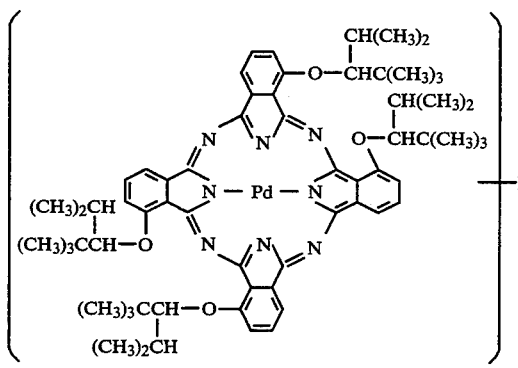
(2-8)

-continued

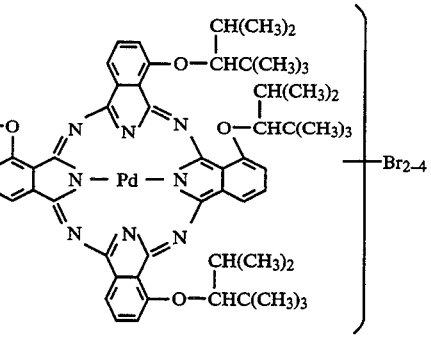
(3-21)

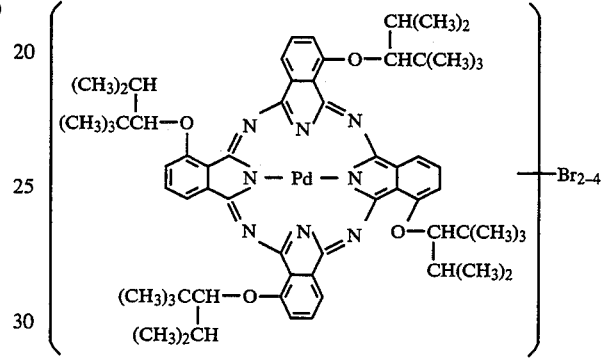
(1-21)

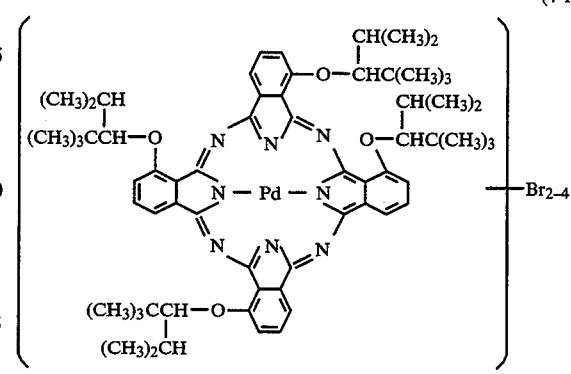
(4-15)

Figure 5:
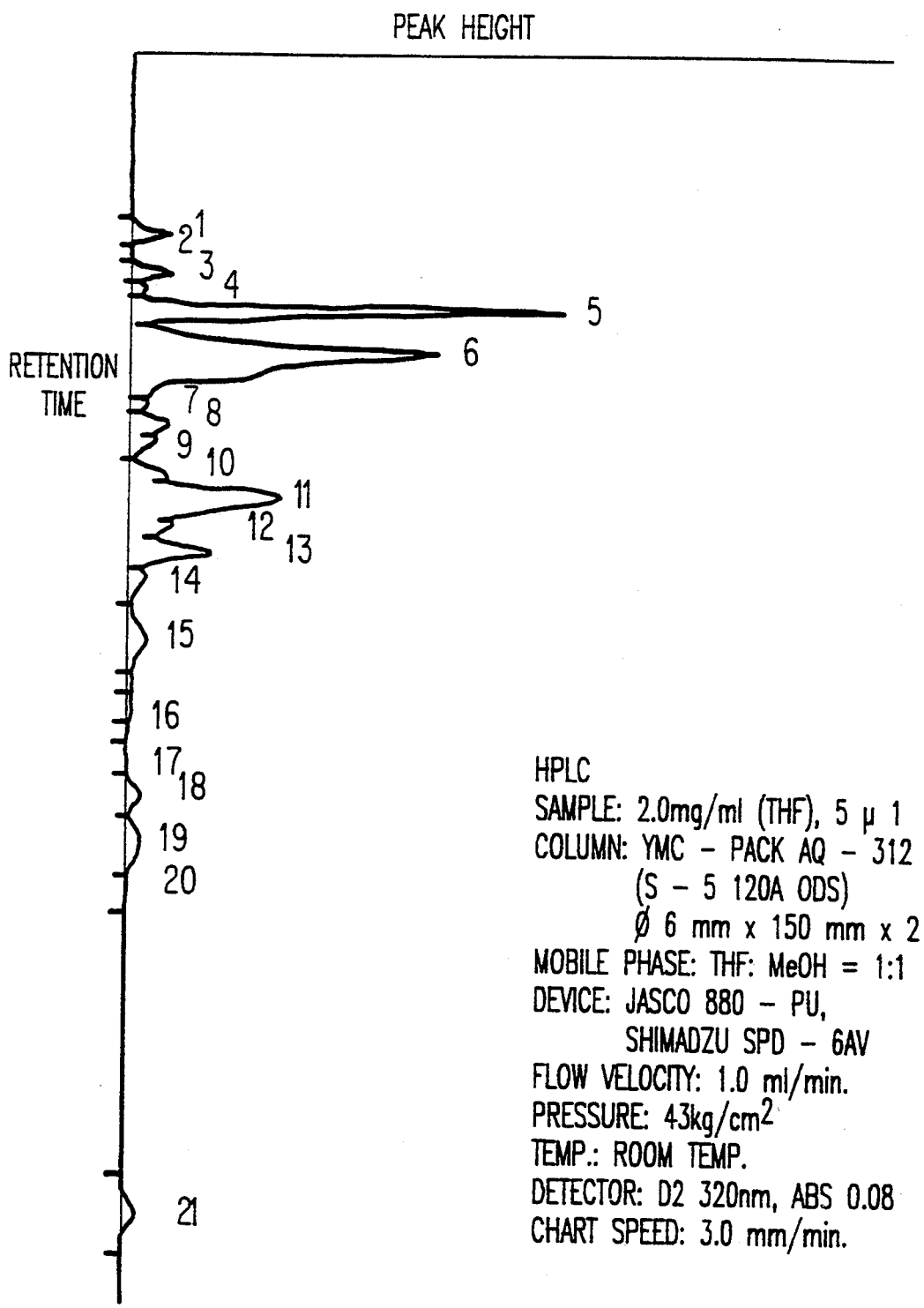
FIG. 5 is a liquid chromatogram of a brominated alkoxyphthalocynine mixture obtained in Example 22.

The liquid chromatogram of the mixture is shown in FIG. 5. A retention time and concentration of each peak are set forth in Table 14. The maximum absorption wave length $\lambda_{max}$ of the mixture was 705 nm, $\epsilon_{max}$ was $1.7 \times 10^5$ $g^{-1}cm^2$, and a melting point was 268°–86° C.

TABLE 14

| Peak No. | Retention Time | Concentration |
|---|---|---|
| 1 | 23.775 | 1.5088 |
| 2 | 24.99 | 0.0758 |
| 3 | 25.942 | 1.4933 |
| 4 | 26.948 | 0.6703 |
| 5 | 28.242 | 20.3779 |
| 6 | 30.742 | 36.4356 |
| 7 | 33.673 | 0.1498 |
| 8 | 34.808 | 2.6473 |
| 9 | 35.723 | 1.4776 |
| 10 | 37.738 | 2.0874 |
| 11 | 39.067 | 14.626 |
| 12 | 40.535 | 2.6031 |
| 13 | 42.178 | 6.0621 |
| 14 | 43.542 | 1.3456 |

TABLE 14-continued

| Peak No. | Retention Time | Concentration |
|---|---|---|
| 15 | 47.407 | 1.9147 |
| 16 | 51.138 | 0.1066 |
| 17 | 54.542 | 0.2127 |
| 18 | 56.338 | 1.51 |
| 19 | 58.805 | 2.5835 |
| 20 | 61.592 | 0.3165 |
| 21 | 80.675 | 1.7949 |
| Total |  | 100 |

EXAMPLE 23

Fifteen grams (15.57 mmol) of a mixture of palladium tetraα-(1,2-dimethylpropyloxy)phthalocyanines in which the ratio of the following formulae (10-7), (11-7), (9-7) and (12-7) was 10:40:30:20:

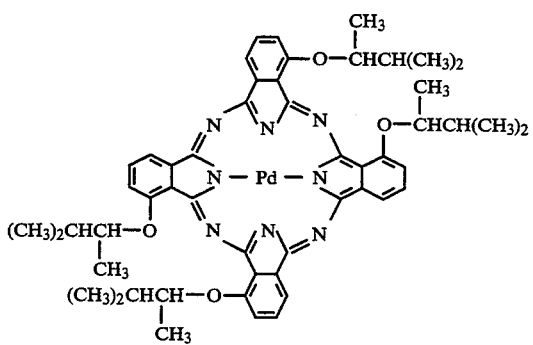
(10-7)

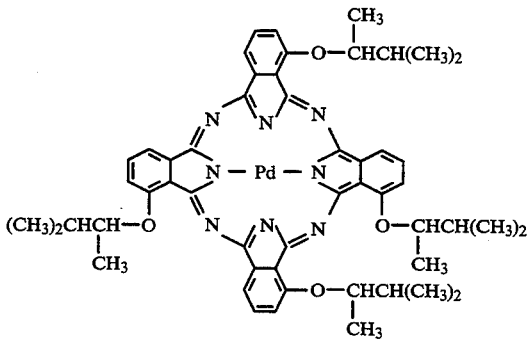
(11-7)

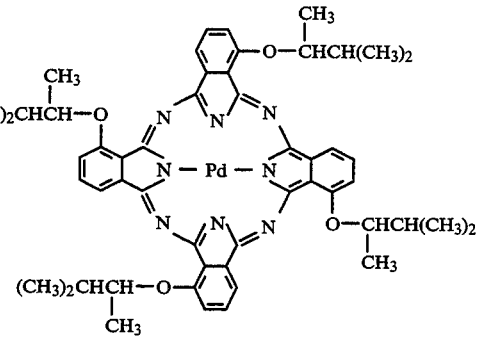
(9-7)

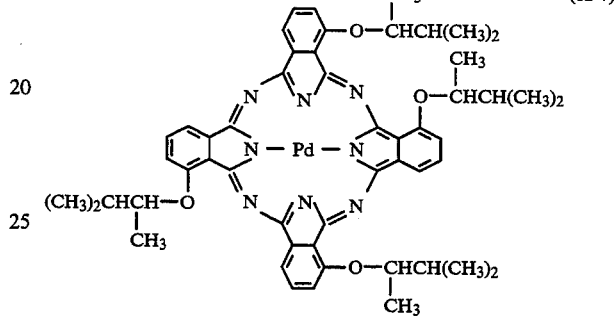
(12-7)

were added to a mixed solvent of 120 g (75 ml) of 1,1,2,2-tetrachloroethane and 100 g (100 ml) of water. Next, 6.2 g (38.79 mmol) of bromine were added, and reaction was then carried out at 60° C. for 2 hours. After cooling to 20° C., separation was carried out. Successively, the resultant organic solvent layer was washed with 100 g of a 10% aqueous sodium hydrogensulfite solution and 100 g of a 5% aqueous sodium hydrogencarbonate solution. The separated organic layer was added dropwise to 240 g of methanol, and the precipitated crystals were then filtered to obtain 16 g of a mixture of brominated phthalocyanines represented by the following formulae (2-9), (3-22), (1-22) and (4-16). The maximum absorption wave length $\lambda_{max}$ of the mixture was 702 nm, $\epsilon_{max}$ was $1.5 \times 10^5 \, g^{-1} cm^2$, and a melting point was 172°–220° C.

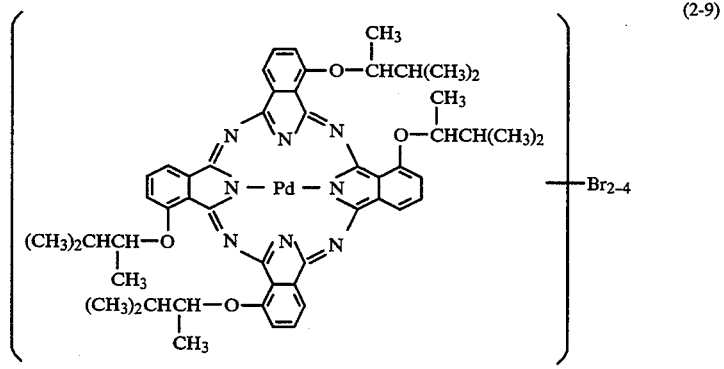
(2-9)

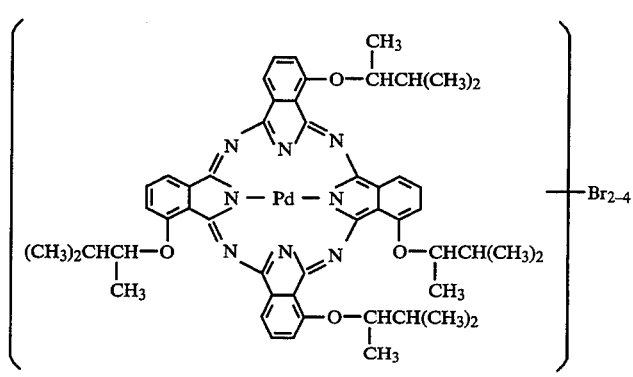
(3-22)
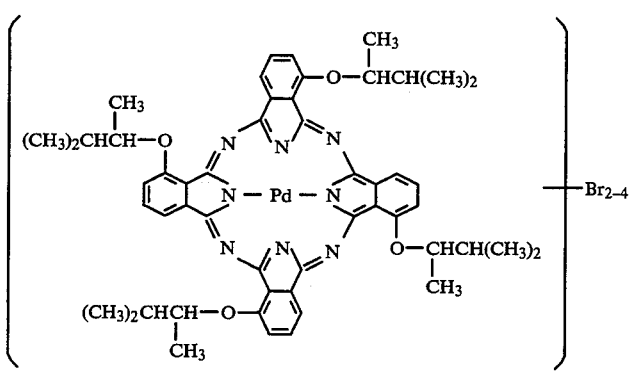
(1-22)
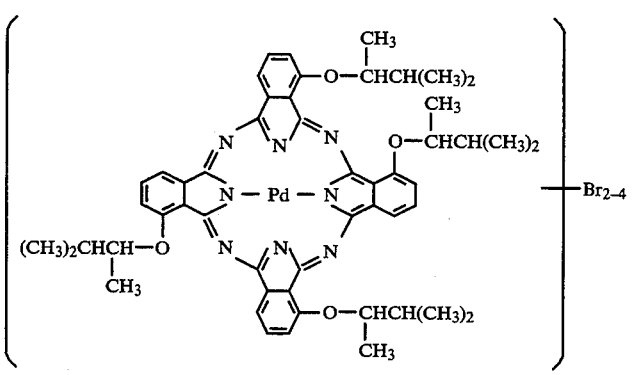
(4-16)
EXAMPLE 24
Fifteen grams (13.95 mmol) of a mixture of palladium tetraα-(1-iso-propylbutyloxy)phthalocyanines in which the ratio of the following formulae (10-8), (11-8), (9-8) and (12-8) was 10:50:30:10
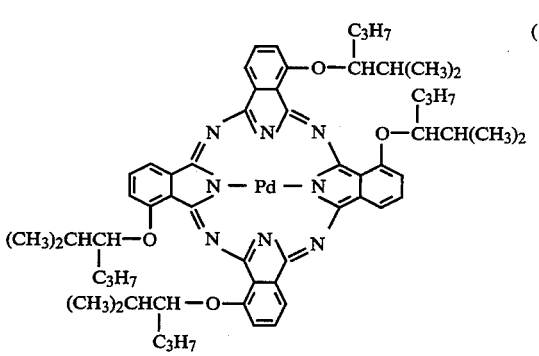
(10-8)
-continued
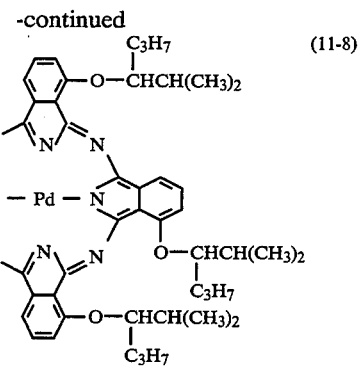
(11-8)

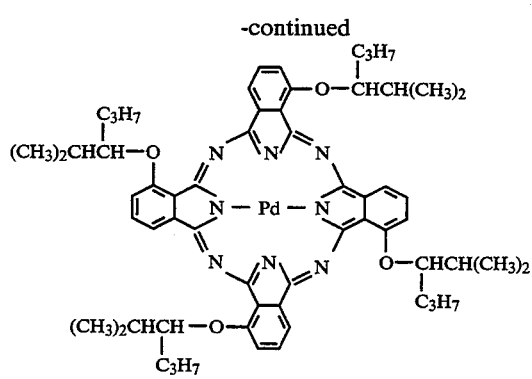

(9-8)

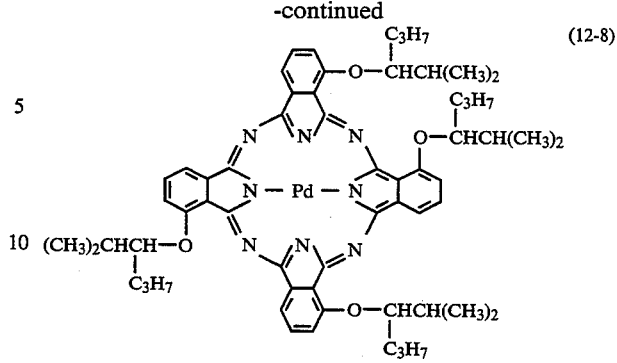

(12-8)

were added to a mixed solvent of 50 g (56 ml) of tetrahydrofuran, 50 g (76 ml) of n-hexane and 100 g (100 ml) of water. Next, 7.2 g (45.05 mmol) of bromine were added, and reaction was then carried out at 60° C. for 2 hours. After cooling to 20° C., 50 g of toluene were added, followed by separation. Successively, the resultant organic solvent layer was washed with 100 g of a 10% aqueous sodium hydrogensulfite solution and 100 g of a 5% aqueous sodium hydrogencarbonate solution. The organic solvent was distilled off, and separation was then carried out through toluene-silica gel chromatography to obtain 16 g of a mixture of brominated phthalocyanines represented by the following formulae (2-10), (3-23), (1-23) and (4-17).

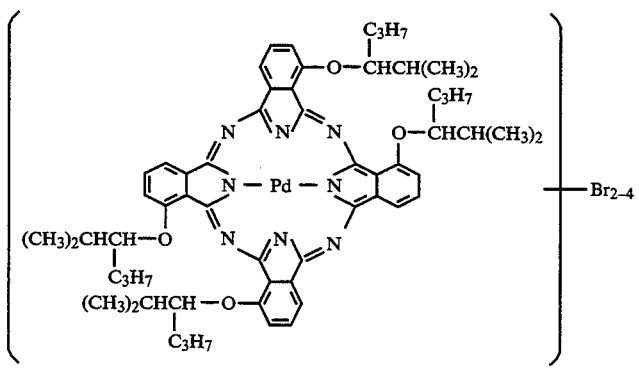

(2-10)

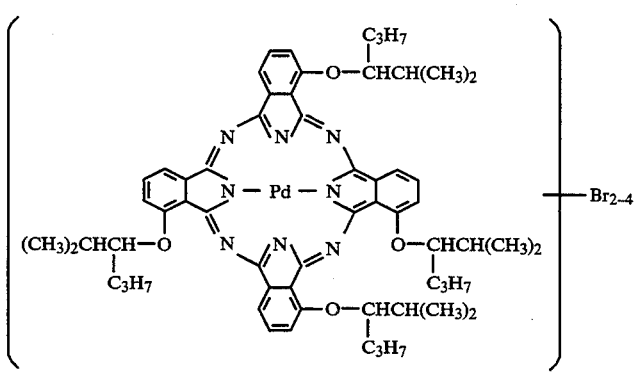

(3-23)

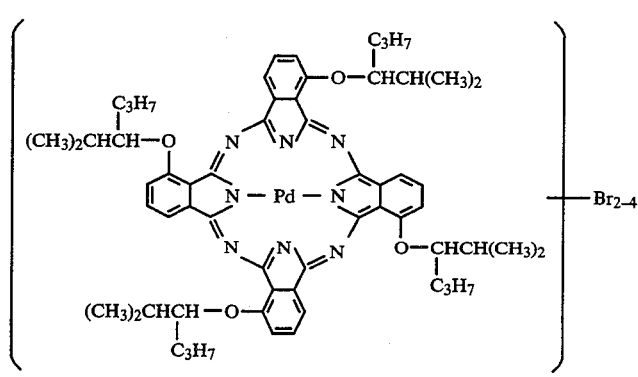

(1-23)

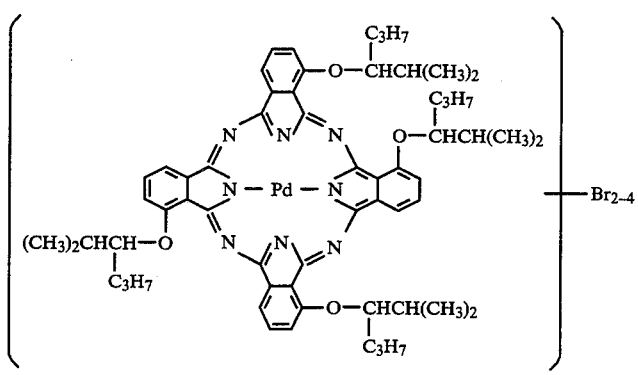

(4-17)

Figure 6:
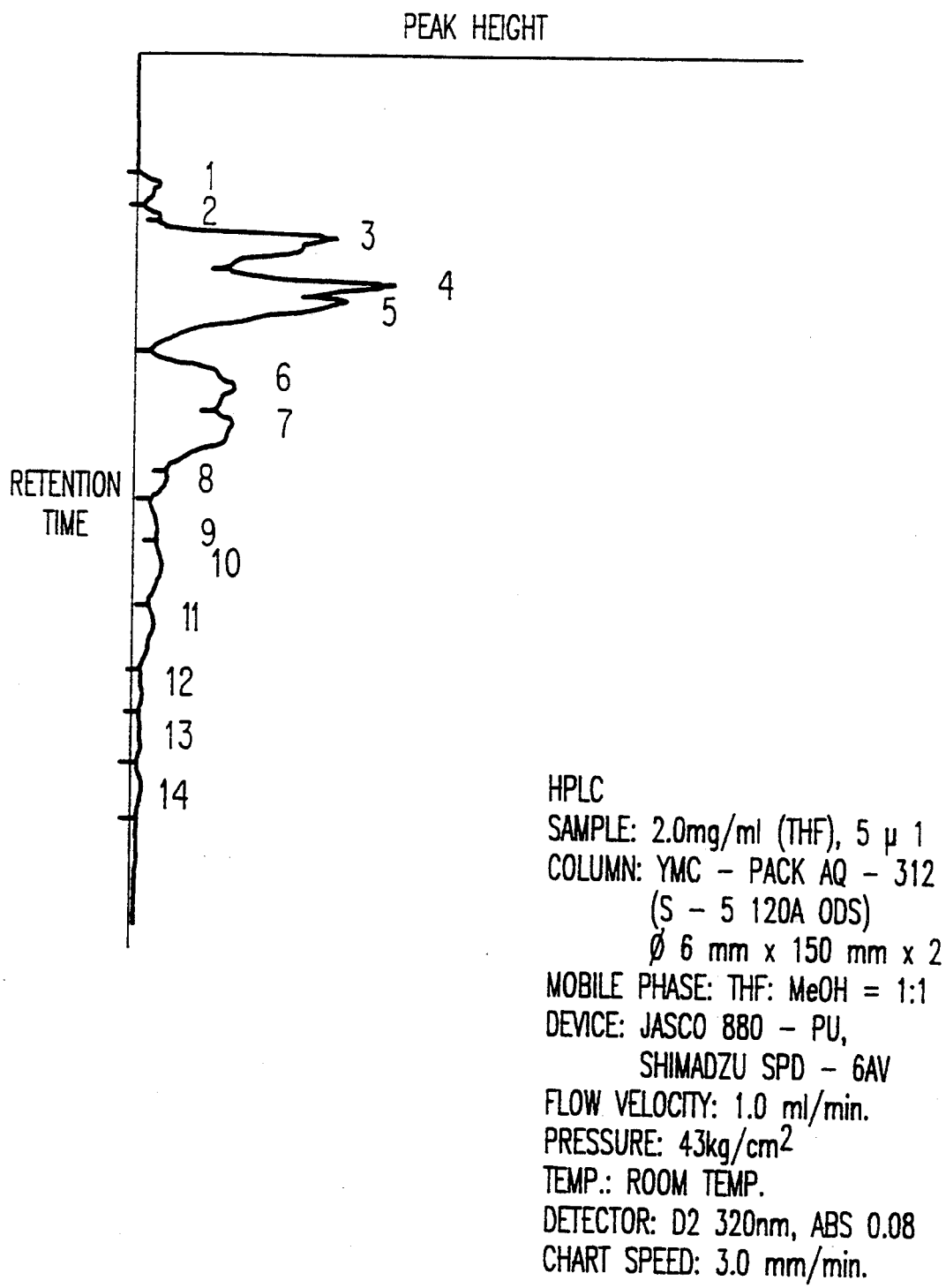
FIG. 6 is a liquid chromatogram of a brominated alkoxyphthalocynine mixture obtained in Example 24.

The liquid chromatogram of the mixture is shown in FIG. 6. A retention time and concentration of each peak are set forth in Table 15. The maximum absorption wave length $\lambda_{max}$ of the mixture was 705 nm, $\epsilon_{max}$ was $1.5 \times 10^5$ g$^{-1}$cm$^2$, and a melting point was 149°–203° C.

TABLE 15

| Peak No. | Retention Time | Concentration |
|---|---|---|
| 1 | 27.217 | 1.287 |
| 2 | 29.017 | 0.7368 |
| 3 | 30.29 | 19.2416 |
| 4 | 33.06 | 17.039 |
| 5 | 33.855 | 18.6948 |
| 6 | 38.598 | 14.3601 |
| 7 | 40.732 | 15.0406 |
| 8 | 43.667 | 2.2369 |
| 9 | 46.788 | 2.6558 |
| 10 | 48.665 | 4.4521 |
| 11 | 51.933 | 2.6343 |
| 12 | 55.533 | 0.6101 |
| 13 | 58.595 | 0.589 |
| 14 | 61.2 | 0.422 |
| Total | | 100 |

EXAMPLE 25

Fifteen grams (14.71 mmol) of a mixture of palladium tetraα-(1-iso-propylpropyloxyphthalocyanines in which the ratio of the following formulae (10-9), (11-9), (9-9) and (12-9) was 10:45:35:15

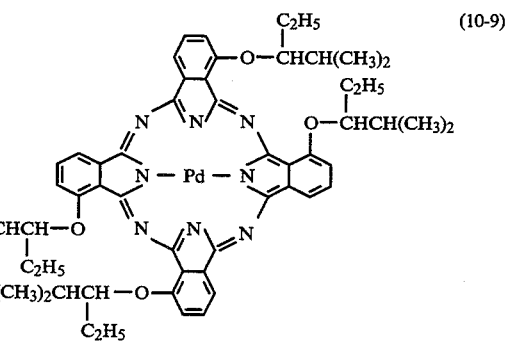

(10-9)

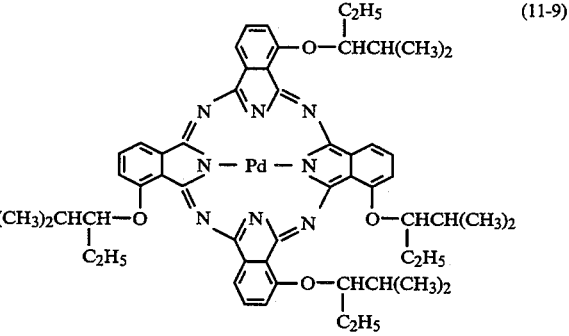

(11-9)

-continued

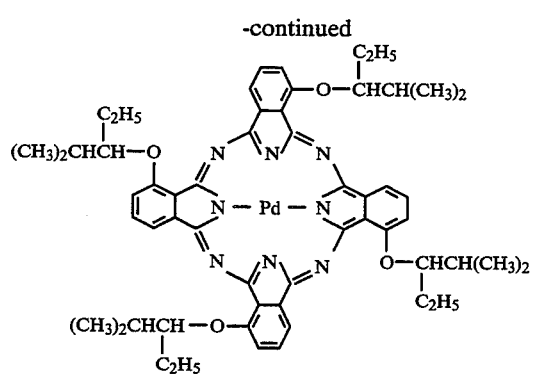
(9-9)

-continued

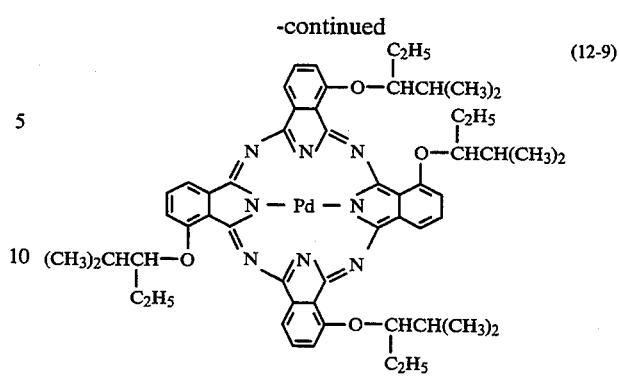
(12-9)

were added to a mixed solvent of 150 g (94 ml) of carbon tetrachloride and 100 g (100 ml) of water. Next, 7.2 g (45.05 mmol) of bromine were added, and reaction was then carried out at 60° C. for 3 hours. After the solution was cooled to 20° C., followed by separation. Successively, the resultant organic solvent layer was washed with 100 g of a 10% aqueous sodium hydrogensulfite solution and 100 g of a 5% aqueous sodium hydrogencarbonate solution. The organic solvent was distilled off, and separation was then carried out by toluene-silica gel chromatography to obtain 15 g of a mixture of brominated phthalocyanines represented by the following formulae (2-11), (3-24), (1-24) and (4-18).

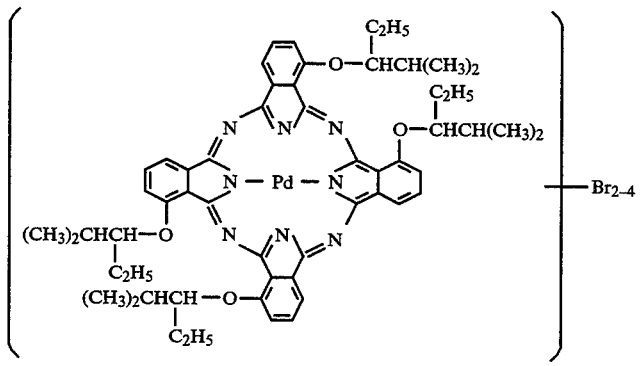
(2-11)

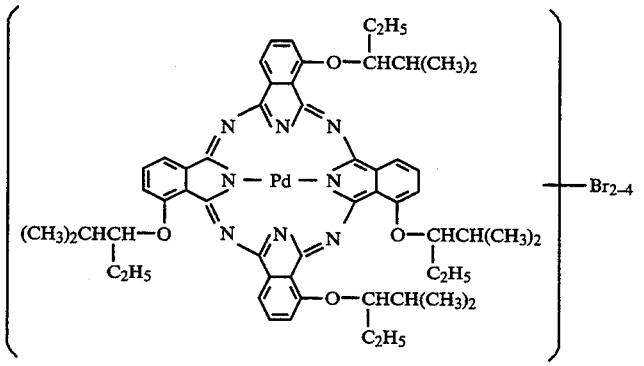
(3-24)

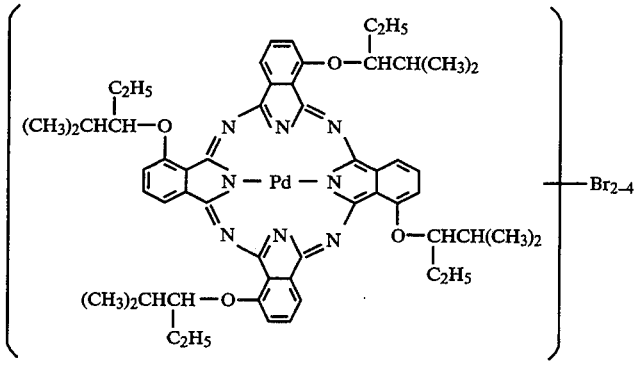

(1-24)

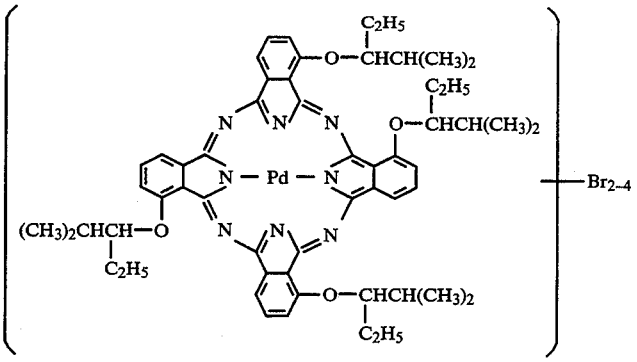

(4-18)

Figure 7:
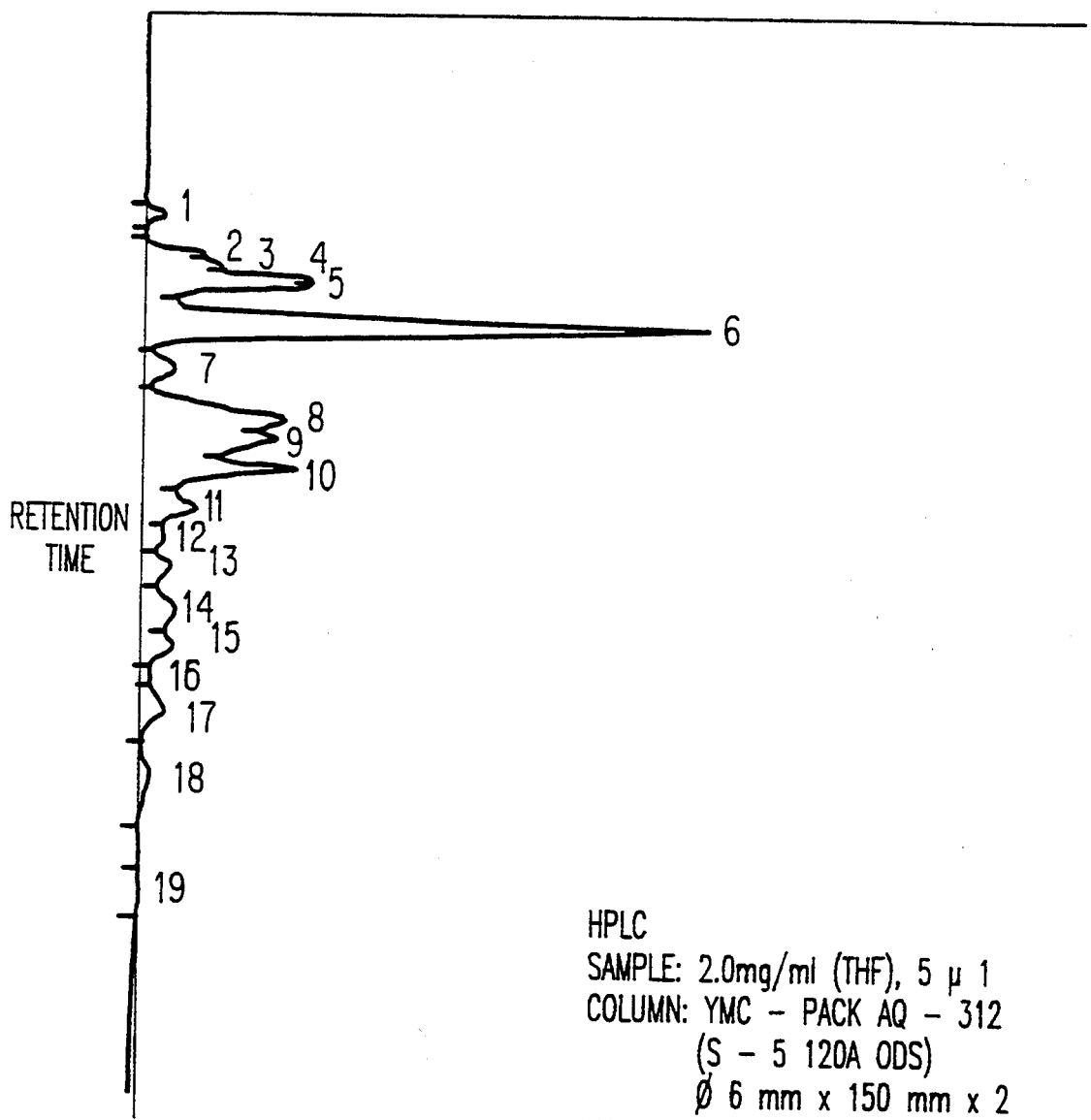
FIG. 7 is a liquid chromatogram of a brominated alkoxyphthalocynine mixture obtained in Example 25.

The liquid chromatogram of the mixture is shown in FIG. 7. A retention time and concentration of each peak are set forth in Table 16. The maximum absorption wave length $\lambda_{max}$ of the mixture was 705 nm, $\epsilon_{max}$ was $1.5 \times 10^5$ g$^{-1}$cm$^2$, and a melting point was 190°–242° C.

TABLE 16

| Peak No. | Retention Time | Concentration |
|---|---|---|
| 1 | 24.4 | 0.5385 |
| 2 | 26.4 | 1.8936 |
| 3 | 27.033 | 2.7709 |
| 4 | 27.728 | 5.1211 |
| 5 | 28.033 | 5.4332 |
| 6 | 30.295 | 32.6837 |
| 7 | 32.467 | 2.3957 |
| 8 | 35.2 | 11.1743 |
| 9 | 36.158 | 9.2337 |
| 10 | 37.84 | 9.6109 |
| 11 | 39.907 | 4.3202 |

TABLE 16-continued

| Peak No. | Retention Time | Concentration |
|---|---|---|
| 12 | 41.333 | 1.712 |
| 13 | 42.933 | 2.4794 |
| 14 | 45.265 | 3.7565 |
| 15 | 47 | 2.503 |
| 16 | 48.732 | 0.5462 |
| 17 | 50.467 | 2.357 |
| 18 | 53.898 | 1.2538 |
| 19 | 60.067 | 0.2164 |
| Total | | 100 |

EXAMPLE 26

Fifteen grams (14.71 mmol) of a mixture of palladium tetra$\alpha$-(1,2-dimethylbutyloxy)phthalocyanines in which the ratio of the following formula (10-10), (11-10), (9-10), and (12-10) was 10:45:35:15

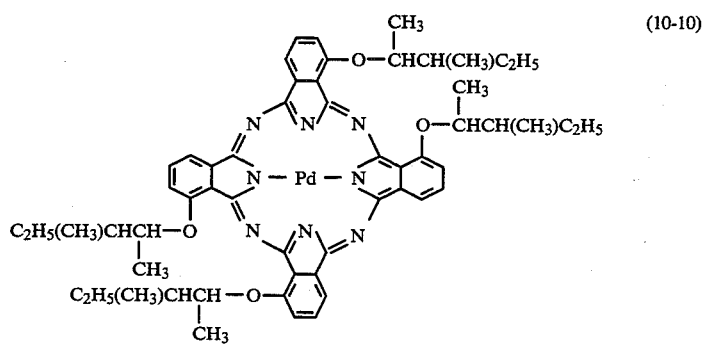

(10-10)

-continued

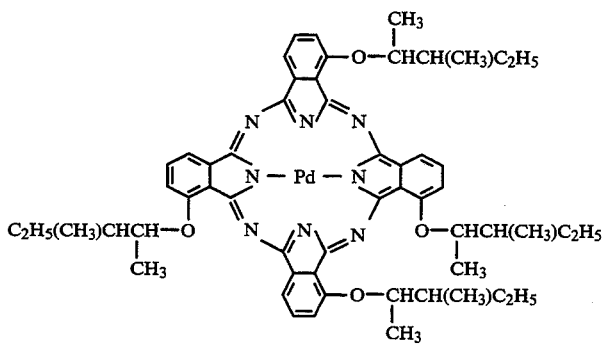
(11-10)

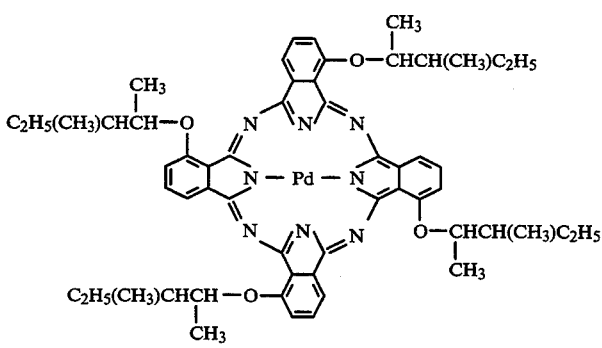
(9-10)

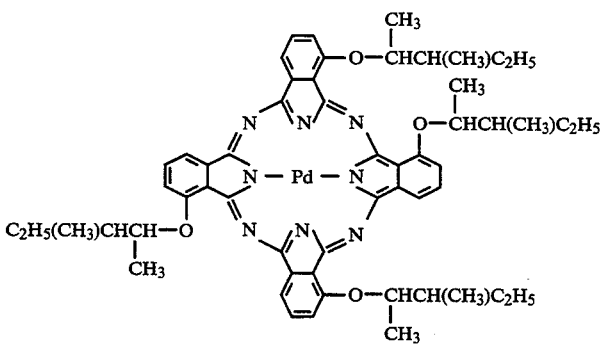
(12-10)

were added to a mixed solvent of 150 g (94 ml) of carbon tetrachloride and 50 g (50 ml) of water. Next, 7.2 g (45.05 mmol) of bromine were added, and reaction was then carried out at 60° C. for 3 hours. After the solution was cooled to 20° C., followed by separation. Successively, the resultant organic solvent layer was washed with 100 g of a 10% aqueous sodium hydrogensulfite solution and 100 g of a 5% aqueous sodium hydrogencarbonate solution. The organic solvent was distilled off, and separation was then carried out by toluene-silica gel chromatography to obtain 15 g of a mixture of brominated phthalocyanines represented by the following formulae (2-12), (3-25), (1-25) and (4-19).

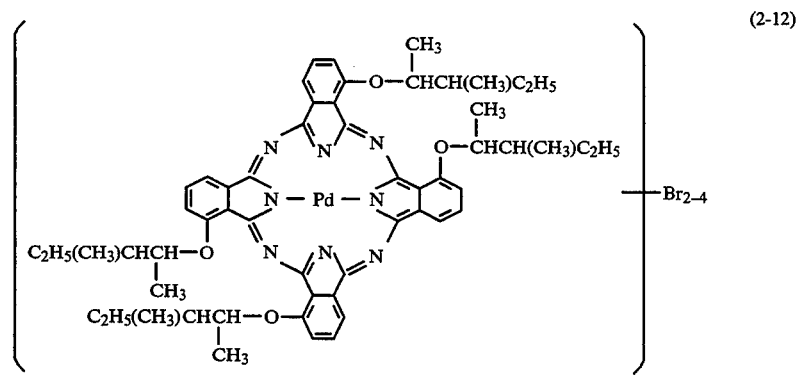
(2-12)

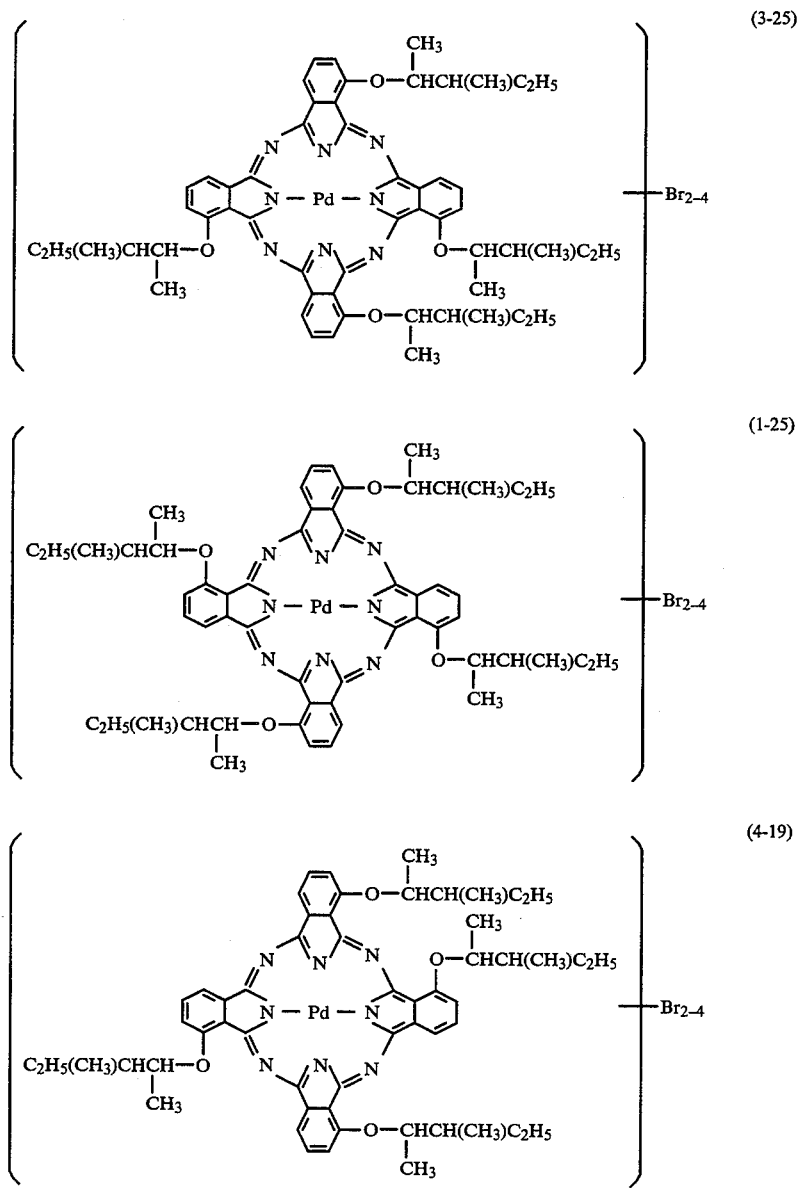

(3-25)

(1-25)

(4-19)

Figure 8:
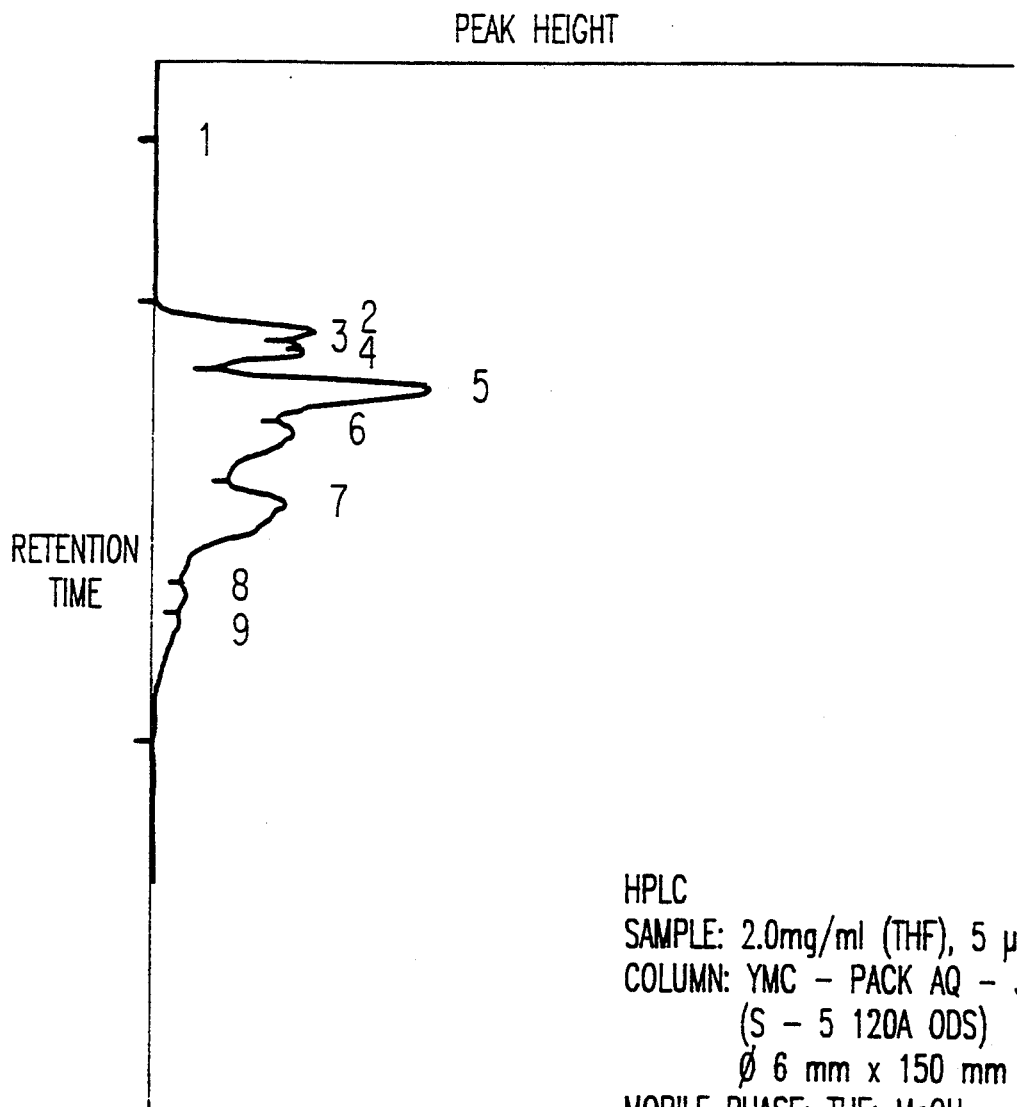
FIG. 8 is a liquid chromatogram of a brominated alkoxyphthalocynine mixture obtained in Example 26.

The liquid chromatogram of the mixture is shown in FIG. 8. A retention time and concentration of each peak are set forth in Table 17. The maximum absorption wave length $\lambda_{max}$ of the mixture was 702 nm, $\epsilon_{max}$ was $1.5 \times 10^5 \, g^{-1} cm^2$, and a melting point was 153°–230° C.

TABLE 17

| Peak No. | Retention Time | Concentration |
|---|---|---|
| 1 | 5.892 | 0.0035 |
| 2 | 15.733 | 10.0303 |
| 3 | 16.43 | 3.7456 |
| 4 | 16.745 | 6.2047 |
| 5 | 18.633 | 30.4854 |
| 6 | 20.733 | 19.1149 |
| 7 | 24.232 | 23.7787 |
| 8 | 28.6 | 2.8332 |
| 9 | 30.065 | 3.8037 |
| Total | | 100 |

EXAMPLE 27

Fifteen grams (14.52 mmol) of a mixture of copper tetraα-(1-iso-propyl-2-methylpropyloxy)phthalocyanines in which the ratio of the following formula (10-11), (11-11), (9-11) and (12-11) was 10:45:35:15

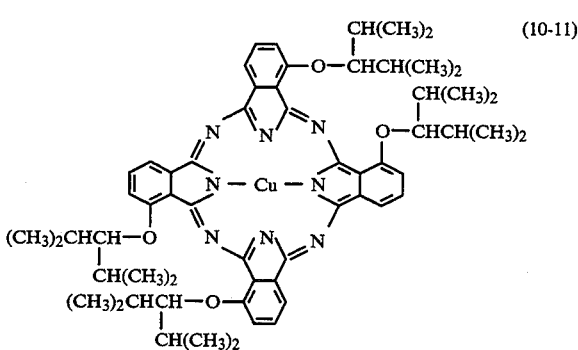

(10-11)

-continued

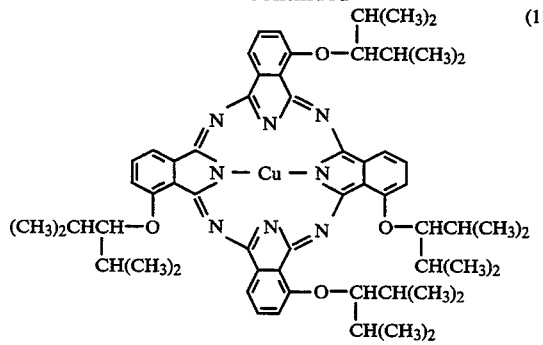
(11-11)

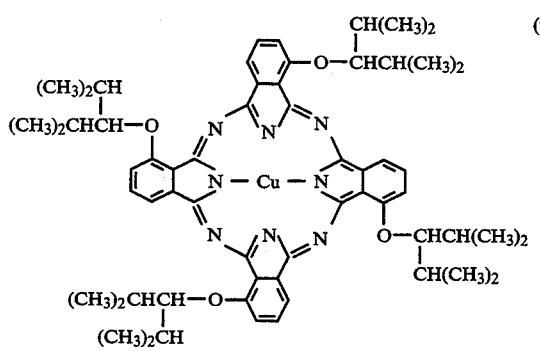
(9-11)

-continued

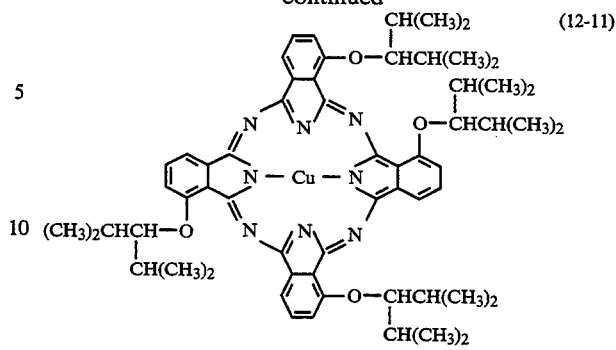
(12-11)

were added to a mixed solvent of 150 g (94 ml) of carbon tetrachloride and 80 g (80 ml) of water. Next, 3.6 g (22.52 mmol) of bromine were added, and reaction was then carried out at 60° C. for 3 hours. The reaction solution was cooled to 20° C., followed by separation. Successively, the resultant organic solvent layer was washed with 100 g of a 10% aqueous sodium hydrogensulfite solution and 100 g of a 5% aqueous sodium hydrogencarbonate solution. The organic solvent was distilled off, and separation was then carried out by toluene-silica gel chromatography to obtain 15 g of a mixture of brominated phthalocyanines represented by the following formulae (2-13), (3-26), (1-26) and (4-20).

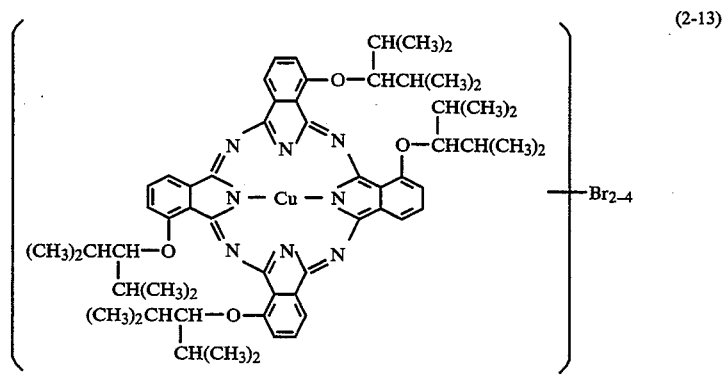
(2-13)

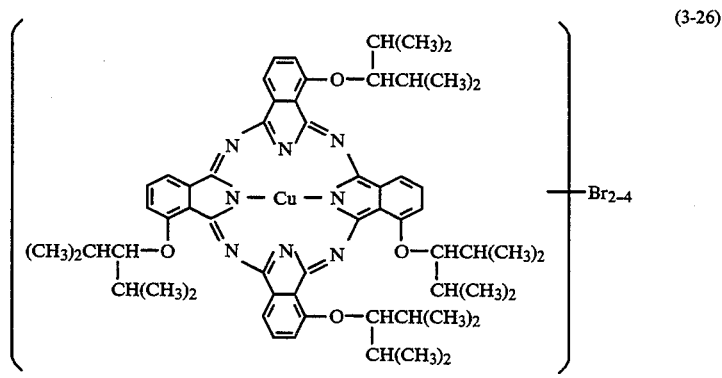
(3-26)

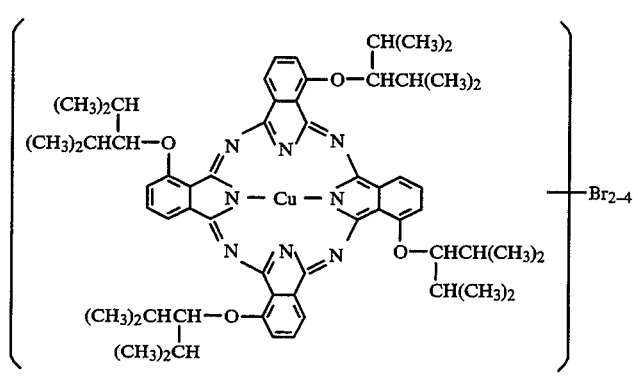

(1-26)

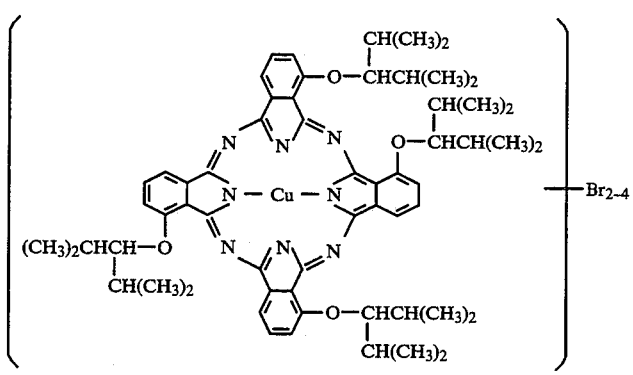

(4-20)

The liquid chromatogram of the mixture is shown in FIG. 9. A retention time and concentration of each peak are set forth in Table 18. The maximum absorption wave length $\lambda_{max}$ of the mixture was 708 nm, $\epsilon_{max}$ was $2.8 \times 10^5$ g$^{-1}$cm$^2$, and a melting point was 195°–240° C.

TABLE 18

| Peak No. | Retention Time | Concentration |
|---|---|---|
| 1 | 6.967 | 0.1361 |
| 2 | 13.2 | 1.1805 |
| 3 | 13.965 | 27.5883 |
| 4 | 14.425 | 44.2342 |
| 5 | 15.242 | 11.1951 |
| 6 | 16.167 | 2.7052 |
| 7 | 16.855 | 2.4921 |
| 8 | 17.467 | 3.1933 |
| 9 | 18.33 | 6.0078 |
| 10 | 19.065 | 0.7638 |
| 11 | 20.767 | 0.3368 |
| 12 | 21.39 | 0.0794 |
| 13 | 22.167 | 0.0874 |
| Total | | 100 |

EXAMPLE 28

Fifteen grams (15.43 mmol) of a mixture of nickel tetraα-(1,2-dimethylbutyloxy)phthalocyanines in which the ratio of the following formulae (10-12), (11-12), (9-12) and (12-12) was 10:45:35:15

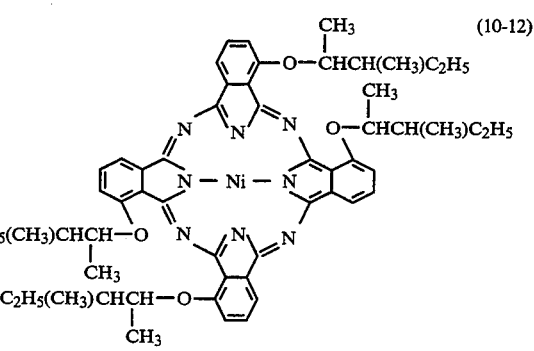

(10-12)

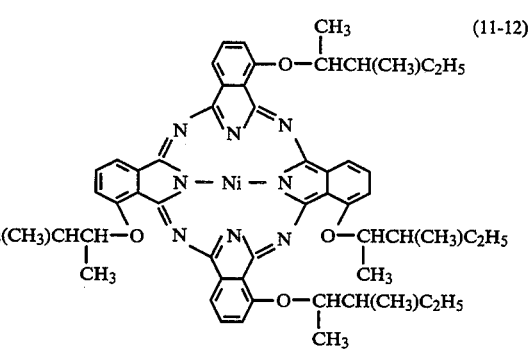

(11-12)

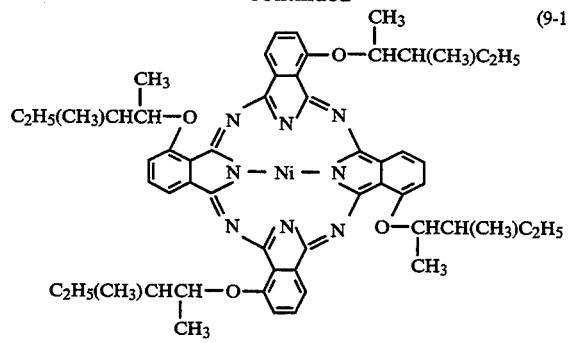

(9-12)

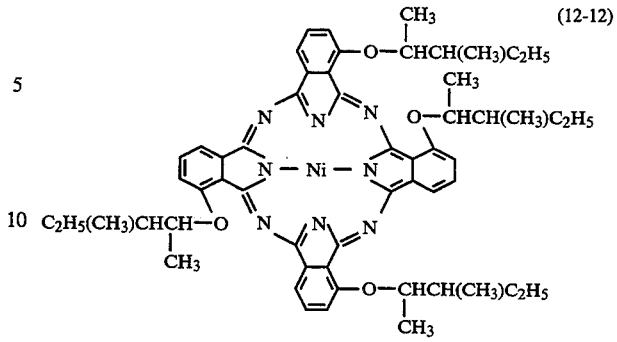

(12-12)

were added to a mixed solvent of 100 g (69 ml) of 1,1,2-trichloroethane and 50 g (50 ml) of water. Next, 3.2 g (20.02 mmol) of bromine were added, and reaction was then carried out at 60° C. for 2 hours. After cooling to 30° C., 20 g of a 10% aqueous sodium hydrogensulfite solution were added to wash the solution. After separation, the organic layer was added dropwise to 360 g of methanol, and the precipitated crystals were then filtered to obtain 16.2 g of a mixture of brominated phthalocyanines represented by the following formulae (2-14), (3-27), (1-27) and (4-21). The maximum absorption wave length $\lambda_{max}$ of the mixture was 708 nm, and $\epsilon_{max}$ was $2.1 \times 10^5$ g$^{-1}$cm$^2$.

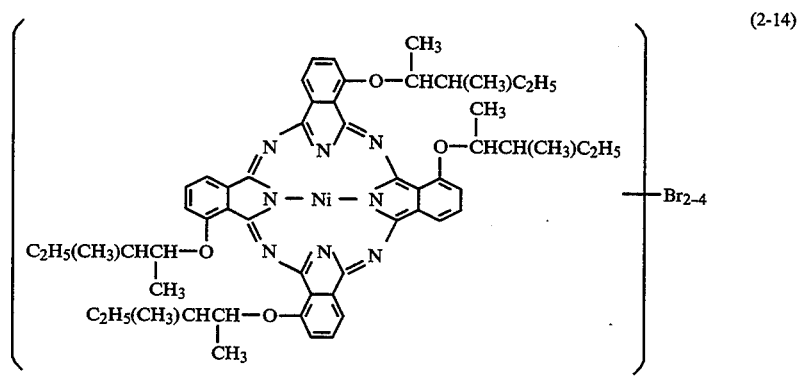

(2-14)

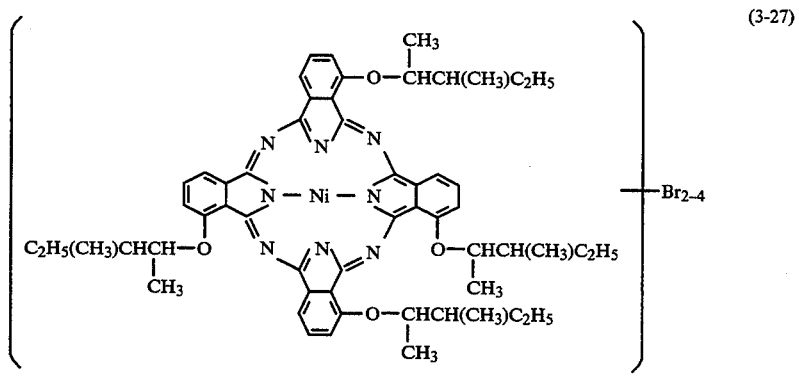

(3-27)

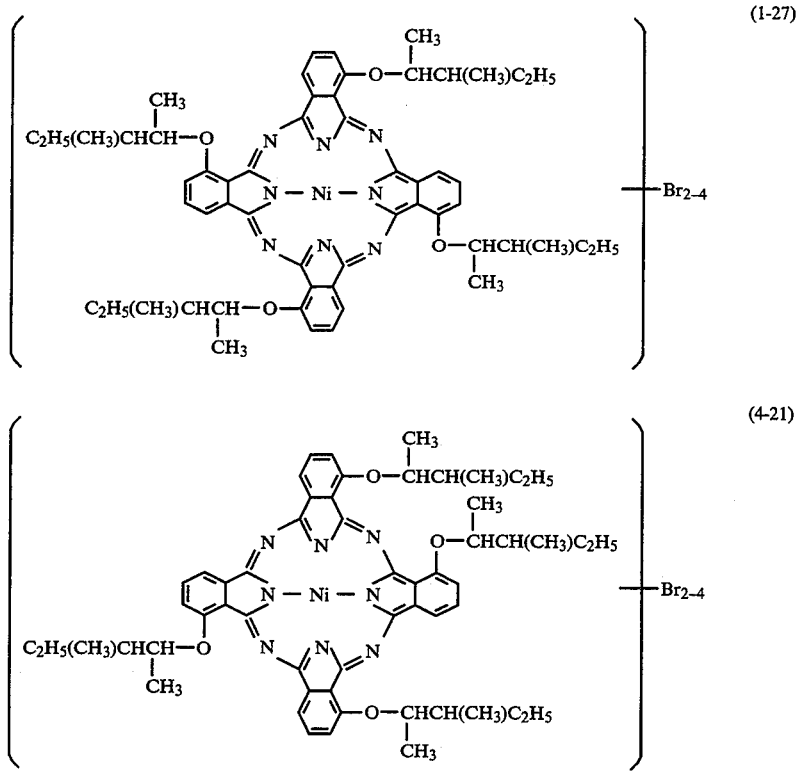

EXAMPLE 29

Six grams of the mixture synthesized in Example 18 were dissolved (30 g/l concentration) in 200 ml of cyclooctane, and the mixture solution was applied on a polycarbonate substrate by a spin coating method. Here, industrially continuous coating properties and film formation properties were tested, and the results were good. A film thickness was 120 nm. The film of gold having a thickness of 50 nm was formed thereon by sputtering. An ultraviolet-setting acrylic resin was further applied thereon by the spin coating method and then irradiated with ultraviolet rays to cure the resin. Thus, a CD-WO optical recording medium was prepared. A reflectance was 70%. A sensitivity was 65 dB of CN ratio when recording was carried out by using a semiconductor laser at 1.4 m/sec, 7 mW and 785 nm. Furthermore, the obtained optical recording medium was excellent in humidity resistance and light resistance.

EXAMPLES 30 TO 32

Optical recording media for CD-WO were prepared following the same procedure as in Example 29 by the use of mixtures obtained in the above-mentioned examples, and industrially continuous coating properties and film formation properties were tested. For the obtained optical recording media for CD-WO, optimum power and recording sensitivity were inspected. The results are set forth in Table 19. Incidentally, reflectances were in the range of 65 to 72%.

TABLE 19

| Example | Mixture | Optimum Power (mW) | Recording Sensitivity (dB) | Coating Properties | Film Formation Properties |
|---|---|---|---|---|---|
| 29 | Example 18 | 7.0 | 65 | Good | Good |
| 30 | Example 19 | 7.0 | 63 | Good | Good |
| 31 | Example 21 | 6.9 | 63 | Good | Good |
| 32 | Example 22 | 7.1 | 62 | Good | Good |

COMPARATIVE EXAMPLES 7 TO 14

In the preparation of the media of Examples 8 to 15, industrially continuous coating properties and film formation properties were tested as in Example 29. The results are set forth in Table 20.

TABLE 20

| Example | Compound | Optimum Power (mW) | Recording Sensitivity (dB) | Coating Properties | Film Formation Properties |
|---|---|---|---|---|---|
| 7 | 2-1 (Example 8) | 7.8 | 62 | Spin coater Filter clogged | Slightly uneven |
| 8 | 3-2 (Example 9) | 8.1 | 63 | Spin coater Filter clogged | Slightly uneven |
| 9 | 3-4 (Example 10) | 6.7 | 61 | Spin coater Filter clogged | Slightly uneven |
| 10 | 1-9 (Example 11) | 7.3 | 60 | Spin coater Filter clogged | Slightly uneven |
| 11 | 4-3 (Example 12) | 7.1 | 62 | Good | Slightly uneven |

TABLE 20-continued

| Example | Compound | Optimum Power (mW) | Recording Sensitivity (dB) | Coating Properties | Film Formation Properties |
|---|---|---|---|---|---|
| 12 | 3-11 (Example 13) | 7.3 | 61 | Good | Slightly uneven |
| 13 | 4-5 (Example 14) | 7.5 | 61 | Good | Slightly uneven |
| 14 | 3-14 (Example 15) | 6.9 | 61 | Good | Slightly uneven |

EXAMPLE 33

Two grams (1.96 mmol) of palladium tetraα-(2-methylpentoxy)phthalocyanine having the formula (9-13)

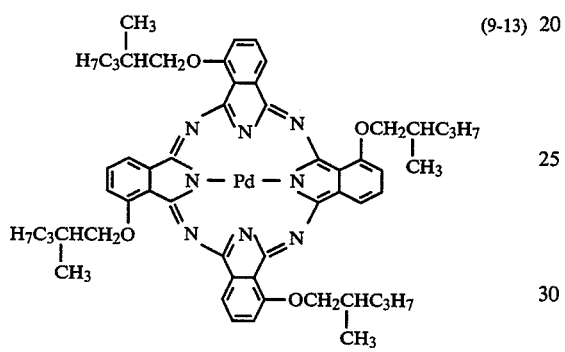
(9-13)

were dissolved in 40 g (61 ml) of n-hexane, and 10 g (10 ml) of water were then added. Next, 2.1 g (15.56 mmol) of sulfuryl chloride were added dropwise at 25° to 30° C., and the solution was heated up to 60 to 65° C. Reaction was then carried out at 60° to 65° C. for 3 hours, and 10 g of a 10% aqueous sodium hydrogensulfite solution were added to wash the solution. The reaction solution was washed with 30% g of water three times and then dried over anhydrous sodium sulfate, and n-hexane was distilled off to obtain 2.4 g of a deep green solid.

The thus obtained solid was purified by silica gel chromatography (a development solvent was toluene). Yield was 2.0 g.

Visible light absorption: $\lambda_{max}$=690 nm, $\log\epsilon_g$=5.0 (toluene).

According to elemental analysis, it was apparent that the number of the substituted chlorine atoms was 4.3. Yield was 87.3%.

| Elemental analysis: $C_{56}H_{59.7}N_8O_4Cl_{4.3}Pd$ | | | | |
|---|---|---|---|---|
| | C | H | N | Cl |
| Calcd. (%) | 57.60 | 5.15 | 9.60 | 13.06 |
| Found (%) | 57.64 | 5.22 | 9.48 | 12.85 |

According to liquid chromatography analysis, the product was a mixture of two isomers, and each single component was separated through a column and identified by NMR and MS analysis. As a result, it was apparent that the two isomers were compounds represented the formula (1-28) (present ratio 70%) and the formula (1-29) (present ratio 30%)

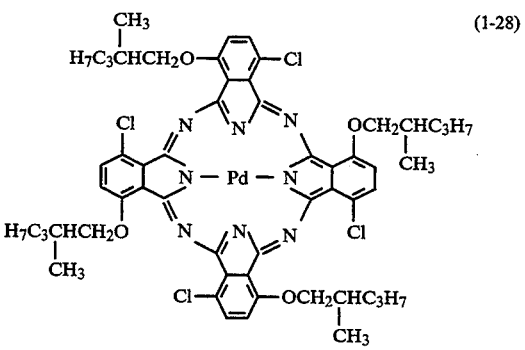
(1-28)

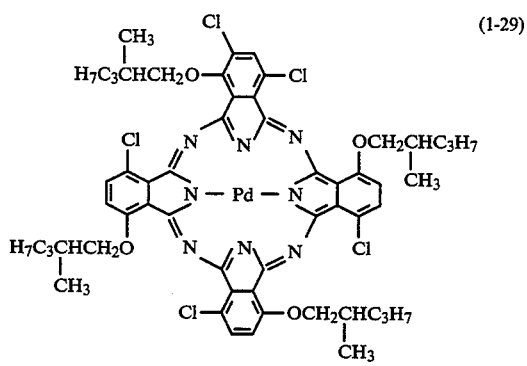
(1-29)

EXAMPLE 34

Ten grams (10.29 mmol) of nickel tetraα-(1,3-dimethylbutyloxy)phthalocyanine having the formula (11-13)

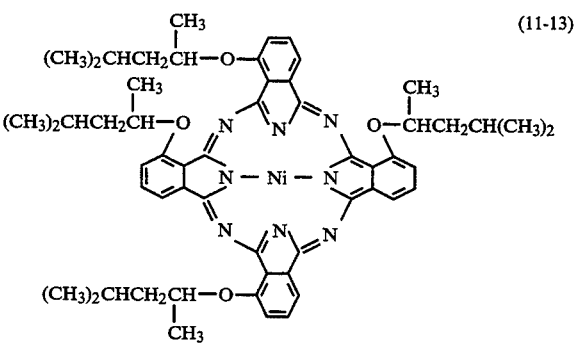
(11-13)

were dissolved in 140 g (212 ml) of n-hexane, and 50 g (50 ml) of water were added. Next, a mixture solution of 6.0 g (37.54 mmol) of bromine and 10 ml of acetic acid was added dropwise at 25° to 30° C., and the solution was then heated up to 60° to 65° C. Reaction was carried out at 60° to 65° C. for 2 hours, and 50 g of a 10% aqueous sodium hydrogensulfite solution were added to wash the solution. The reaction solution was washed with 100 g of water three times and then dried over anhydrous sodium sulfate, and n-hexane was distilled off to obtain 11.0 g of a deep green solid.

The thus obtained solid was purified by the use of silica gel chromatography (a development solvent was toluene).

Yield was 9.7 g.

Visible light absorption: $\lambda_{max}$=704.5 nm, $\log\epsilon_g$=5.1 (toluene).

According to elemental analysis, it was apparent that the number of the substituted bromine atoms was 1.9. Yield was 84.3%.

Elemental analysis: $C_{56}H_{62.1}N_8O_4Br_{1.9}Ni$

|  | C | H | N | Br |
|---|---|---|---|---|
| Calcd. (%) | 59.96 | 5.58 | 9.99 | 13.53 |
| Found (%) | 60.25 | 5.81 | 9.45 | 13.72 |

According to liquid chromatography analysis, the product was a mixture of two isomers, and each single component was separated through a column and identified by NMR and MS analysis. As a result, it was apparent that the two isomers were compounds represented by the formula (3-28) (present ratio 90%) and the formula (3-29) (present ratio 10%).

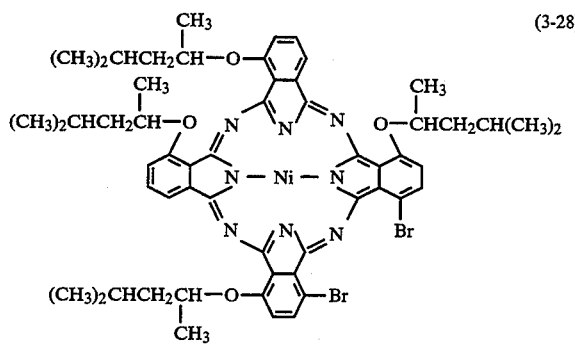
(3-28)

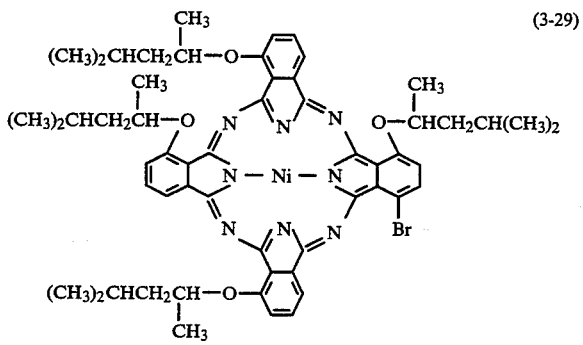
(3-29)

EXAMPLE 35

Five grams (4.65 mmol) of a mixture of palladium tetraα-(1-isopropyl-2-methylpropyloxy)phthalocyanines in which the ratio of the above-mentioned formulae (12-3) and (10-3) was 90:5 were dissolved in 35 g (53 ml) of n-hexane and 45 g (51 ml) of tetrahydrofuran, and 25 g (25 ml) of water were further added. Next, a mixture solution of 2.4 g 15.02 mmol) of bromine and 5 g of acetic acid was added dropwise at 25° to 30° C., and the solution was then heated up to 50° to 55° C. Reaction was carried out at 50° to 55° C. for 2 hours, and 30 g of a 10% aqueous sodium hydrogensulfite solution were added to wash the solution. The reaction solution was washed with 50 g of water three times and then dried over anhydrous sodium sulfate. The n-hexane and the tetrahydrofuran were distilled off to obtain 6.5 g of a deep green solid.

The thus obtained solid was purified by silica gel chromatography (a development solvent was toluene/n-hexane=1/1). Yield was 5.3 g.

Visible light absorption: $\lambda_{max}=706$ nm, $\log\epsilon_g=5.1$ (toluene).

According to elemental analysis, it was apparent that the number of the substituted bromine atoms was 2.8. Yield was 89.3%.

Elemental analysis: $C_{60}H_{69.2}N_8O_4Br_{2.8}Pd$

|  | C | H | N | Br |
|---|---|---|---|---|
| Calcd. (%) | 55.58 | 5.38 | 8.64 | 17.26 |
| Found (%) | 54.42 | 5.73 | 8.54 | 17.08 |

According to liquid chromatography and MS analysis, the product was a mixture of two isomers of the above-mentioned formulae (4-12) and (2-5).

EXAMPLE 36

Fifty grams (46.8 mmol) of a mixture of palladium tetraα-(1-isopropyl-2-methylpropyloxy)phthalocyanines in which the ratio between the above-mentioned formulae (11-3) and (9-3) was 90:10 were dissolved in 318 g (200 ml) of 1,1,2,2-tetrachloroethane and 630 g (800 ml) of ethylcyclohexane, and 500 g (500 ml) of water were further added. Next, a mixture solution of 21.2 g (132.65 mmol) of bromine and 64 g (40 ml ) of 1,1,2,2-tetrachloroethane was added dropwise at 55° to 60° C. and reaction was then carried out at 55° to 60° C. for 1 hour, and 250 g of a 10% aqueous sodium hydrogensulfite solution were added to wash the solution. The reaction solution was washed with 500 g of water three times and then dried over anhydrous sodium sulfate. The reaction solution was concentrated and then purified by the use of silica gel chromatography (a development solvent was toluene/n-hexane=1/1). Yield was 56.1 g.

Visible light absorption: $\lambda_{max}=706$ nm, $\log\epsilon_g=5.1$ (toluene).

According to elemental analysis, it was apparent that the number of the substituted bromine atoms was 2.8. Yield was 93.0%.

Elemental analysis: $C_{60}H_{69.2}N_8O_4Br_{2.8}Pd$

|  | C | H | N | Br |
|---|---|---|---|---|
| Calcd. (%) | 55.58 | 5.38 | 8.64 | 17.26 |
| Found (%) | 56.28 | 5.42 | 8.36 | 17.23 |

According to liquid chromatography and MS analysis, the product was a mixture of isomers of the above-mentioned formulae (3-18) and (1-18).

EXAMPLE 37

Fifty grams (46.48 mmol) of a mixture of palladium tetraα-(1-isopropyl-2-methylpropyloxy ) phthalocyanines in which the ratio of the above-mentioned formulae (11-3) to (9-3) was 90:10 were dissolved in 288 g (200 ml ) of 1,1,2-trichloroethane, and 100 g (100 ml) of water were then added. Next, a mixture solution of 22.3 g (139.53 mmol) of bromine and 58 g (36 ml ) of 1,1,2-trichloroethane was added dropwise at 55° to 60° C. and reaction was then carried out at 55° to 60° C. for 1 hour, and 50 g of a 10% aqueous sodium hydrogensulfite solution were added to wash the solution. The resultant organic layer was added dropwise to 790 g of methanol, and the precipitated crystals were filtered. Yield was 59.8 g.

Visible light absorption: $\lambda_{max}=706.5$ nm, $\log\epsilon_g=5.1$ (toluene).

According to elemental analysis, it was apparent that the number of the substituted bromine atoms was 3.0. Yield was 98.0%.

| Elemental analysis: $C_{60}H_{69}N_8O_4Br_3Pd$ | | | | |
|---|---|---|---|---|
| | C | H | N | Br |
| Calcd. (%) | 54.91 | 5.30 | 8.59 | 18.27 |
| Found (%) | 55.60 | 5.04 | 8.64 | 18.36 |

According to liquid chromatography and MS analysis, the product was a mixture of isomers of the above-mentioned formulae (3-18) and (1-18).

EXAMPLE 38

Ten grams (8.73 mmol) of a mixture of copper tetraα-(1-isopropyl-2-methylpropyloxy)phthalocyanines in which the ratio between the following formulae (11-14) and (10-13) was 90:10

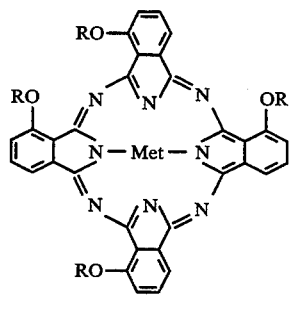

(11-14)

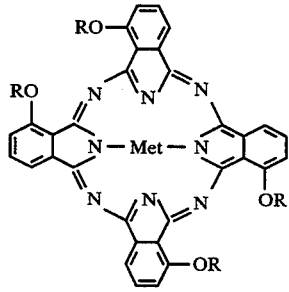

(10-13)

Met = Cu
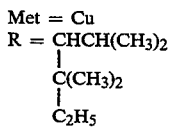

were dissolved in 54 g (40 ml) of 1,1,1-trichloroethane, and 20 g (20 ml) of water were then added. Next, a mixture solution of 4.19 g (26.22 mol) of bromine and 11 g (8 ml) of 1,1,1-trichloroethane was added dropwise at 45° to 50° C., and reaction was then carried out at 50° to 55° C. for 2 hours, and 20 g of a 10% aqueous sodium hydrogensulfite solution were added to wash the solution. The resultant organic layer was added dropwise to 152 g of methanol, and the precipitated crystals were filtered.

Yield (amount) was 11.8 g, and yield (ratio) was 97.5%.

Visible light absorption: $\lambda_{max}=718.0$ nm, $\log\epsilon_g=5.1$ (toluene).

According to elemental analysis, it was apparent that the number of the substituted bromine atoms was 3.0.

| Elemental analysis: $C_{68}H_{85}N_8O_4Br_3Cu$ | | | | |
|---|---|---|---|---|
| | C | H | N | Br |
| Calcd. (%) | 59.11 | 6.20 | 8.11 | 17.35 |
| Found (%) | 59.41 | 5.92 | 8.00 | 17.53 |

According to liquid chromatography analysis, the product was a mixture of three isomers, and each single component was separated through a column and identified by NMR and MS. As a result, it was apparent that the three isomers were compounds represented by the formula (3-30) (present ratio 50%), the formula (3-31) (present ratio 40%) and the formula (2-15).

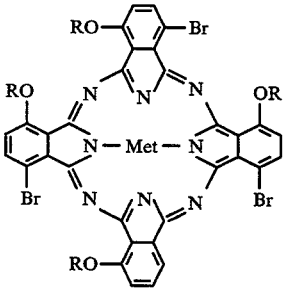

(3-30)

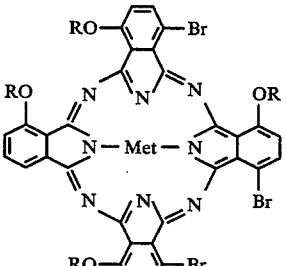

(3-31)

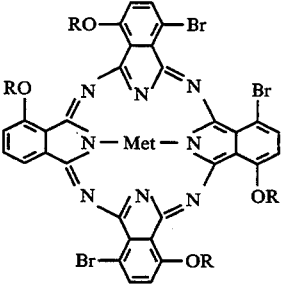

(2-15)

Met = Cu
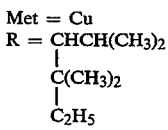

COMPARATIVE EXAMPLE 15

Ten grams (9.81 mmol) of a mixture of palladium tetraα-(1,3-dimethylbutyloxy)phthalocyanines having the formulae (9-14)

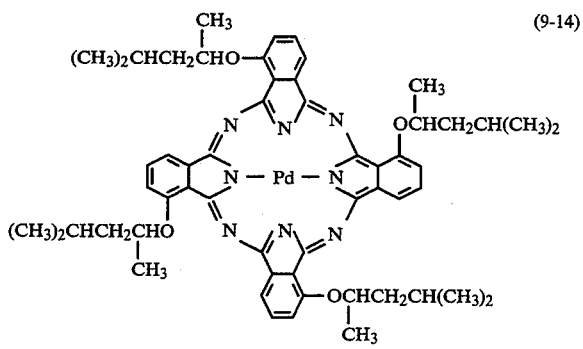

(9-14)

| Elemental analysis: $C_{56}H_{60.4}N_8O_4Br_{3.6}Pd$ | | | | |
|---|---|---|---|---|
| | C | H | N | Br |
| Calcd. (%) | 51.91 | 4.71 | 8.56 | 21.58 |
| Found (%) | 52.42 | 4.83 | 8.77 | 21.77 |

According to liquid chromatography and MS analysis, it was apparent that the product was a compound represented by the formula (1-30).

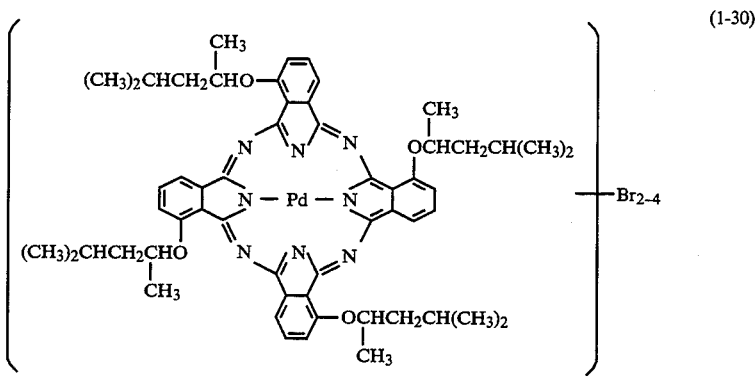

(1-30)

were dissolved in 400 g (251 mmol) of carbon tetrachloride, and a mixture solution of 12.5 g (78.21 mmol) of bromine and 10 g of acetic acid was added dropwise at 25° to 30° C., and the solution was then heated up to 60° to 65° C. Reaction was carried out at 60° to 65° C. for 10 minutes and at this point of time, a blackish green solid was precipitated. Under this state, the reaction was performed at 60° to 65° C. for 4 hours, and 50 g of a 10% aqueous sodium hydrogensulfite solution were then added to wash the solution. 200 g of chloroform were added to the reaction solution to dissolve the solid, washed with 200 g of water 3 times, and then dried over anhydrous sodium sulfate. Carbon tetrachloride was distilled off to obtain a deep green solid.

The thus obtained solid was purified by silica gel chromatography (a development solvent was toluene). Yield was 6.7 g, and 3 g of the raw material were recovered.

Visible light absorption: $\lambda_{max}=699.5$ nm, $log\epsilon_g=5.1$ (toluene).

According to elemental analysis, it was apparent that the number of the substituted bromine atoms was 3.6.

Yield was 52.4%, and there was no water in the solvent, and therefore the reaction did not proceed sufficiently and effective bromination could not be achieved.

COMPARATIVE EXAMPLE 16

Five grams (4.65 mmol) of a mixture of palladium tetraα-(1-isopropyl-2-methylbutyloxy)phthalocyanines in which the ratio of the formula (11-3) to the formula (9-3) was 90:10 were dissolved in 58 g (40 ml) of 1,1,2-trichloroethane, and a mixture solution of 2.23 g (13.95 mmol) of bromine and 6 g (4 ml) of 1,1,2-trichloroethane was added dropwise at 50° to 55° C. in order to introduce three bromine atoms on the average, and reaction was carried out at 55° to 60° C. for 1 hour. 10 g of a 15% aqueous sodium hydrogensulfite solution were then added to wash the solution. The resultant organic layer was added dropwise to 80 g of methanol, and the precipitated crystals were filtered. Yield was 5.3 g.

Visible light absorption: $\lambda_{max}=696.0$ nm, $log\epsilon_g=5.3$ (toluene).

According to elemental analysis, it was apparent that the number of the substituted bromine atoms was 1.0.

| Elemental analysis: $C_{60}H_{71}N_8O_4Br_1Pd$ | | | | |
|---|---|---|---|---|
| | C | H | N | Br |
| Calcd. (%) | 62.42 | 6.20 | 9.71 | 6.92 |
| Found (%) | 62.60 | 6.04 | 9.54 | 7.08 |

According to liquid chromatography and MS analysis, the product was a mixture of isomers having the following formulae (3-32) and (1-31), and the desired three-substituted product could not be obtained.

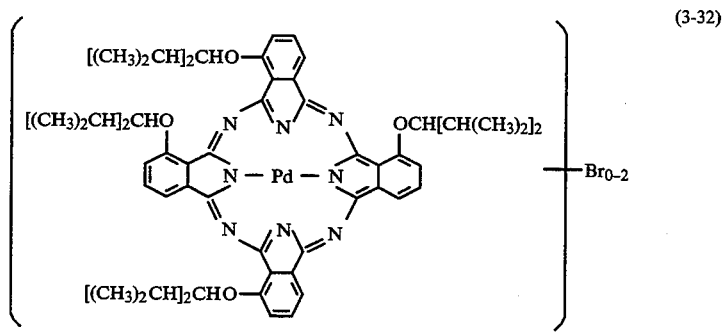

(3-32)

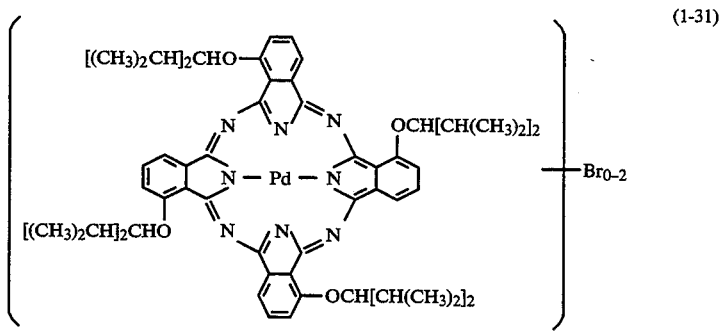

(1-31)

As described above, in the present invention, a halogenated alkoxyphthalocyanine which can be obtained by halogenating a phthalocyanine having, at the α-position, an alkoxy group having 2 to 4 of the secondary, tertiary or quaternary carbon atoms in all contains 5 or more isomers. Therefore, the alkoxyphthalocyanine is excellent in solubility in a solvent and film formation properties in a coating process. Furthermore, an absorption wave length can be changed by adjusting the amount of the halogen atoms to be introduced. Moreover, the phthalocyanine compound of the present invention has an alkoxy group having a large steric hindrance and the halogen atoms, and therefore it can provide recording layers of optical recording media having excellent sensitivity.

We claim:

1. A method for preparing a halogenated phthalocyanine compound represented by the formula (20)

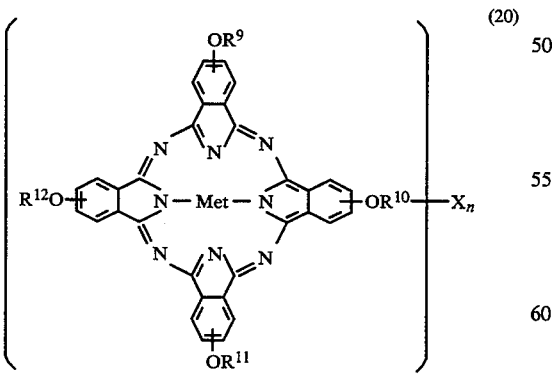

(20)

wherein each of $R^9$ to $R^{12}$ independently is a substituted or unsubstituted alkyl group; and Met is two hydrogen atoms, a divalent metallic atom, a trivalent or a tetravalent metallic derivative; X is chlorine, bromine or iodine; and n is $1 \leq n \leq 12$, which comprises reacting a phthalocyanine compound represented by the formula (19)

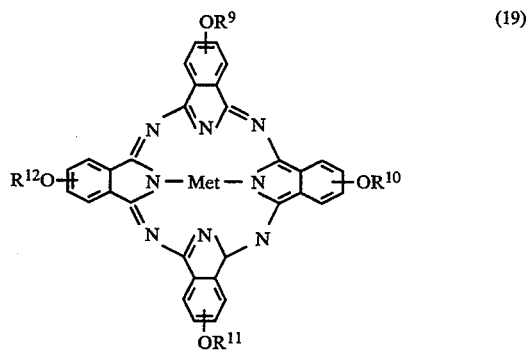

(19)

wherein $R^9$ to $R^{12}$ and Met have the same meanings as in the formula (20), with a halogenating agent at 20° to 90° C. in a mixed solvent of an organic solvent and water.

2. The method for preparing a halogenated phthalocyanine compound according to claim 1 wherein said phthalocyanine compound is a compound represented by the formula (21), (22), (23) or (24)

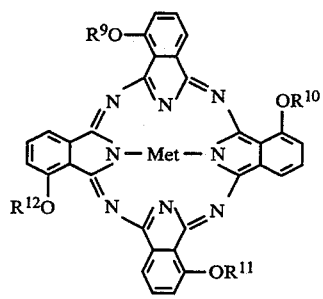 (21)

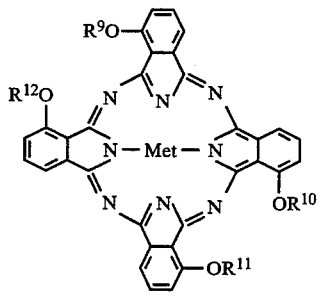 (22)

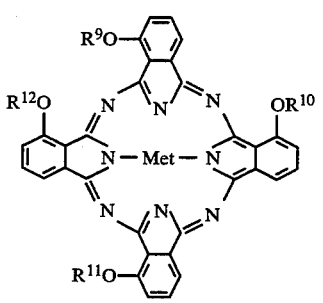 (23)

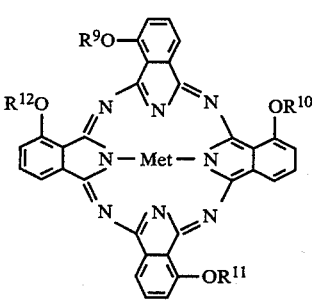 (24)

wherein $R^9$ to $R^{12}$ and Met have the same meanings as in the formula (19), or a mixture of these compounds; and said halogenated phthalocyanine compound is a compound represented by the formula (25), (26), (27) or (28)

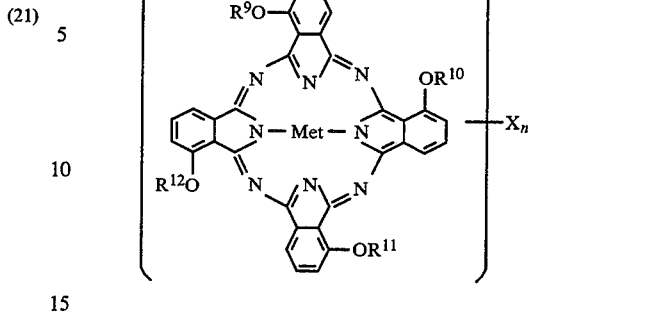 (25)

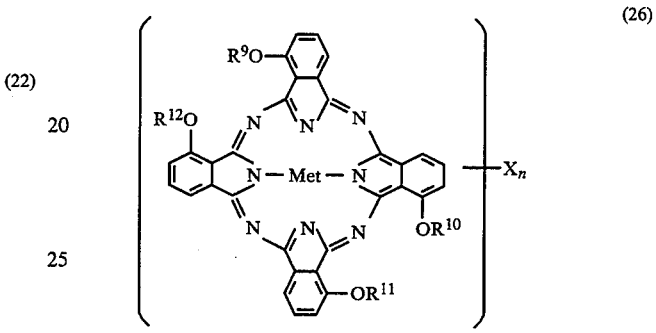 (26)

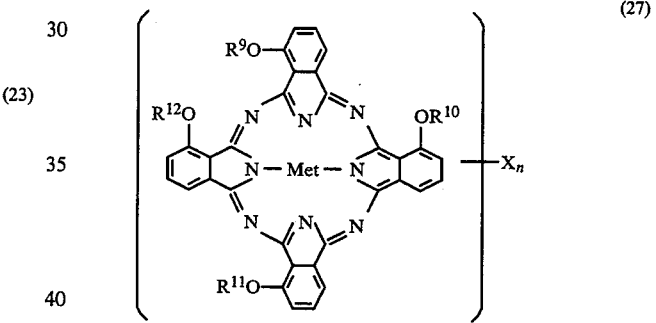 (27)

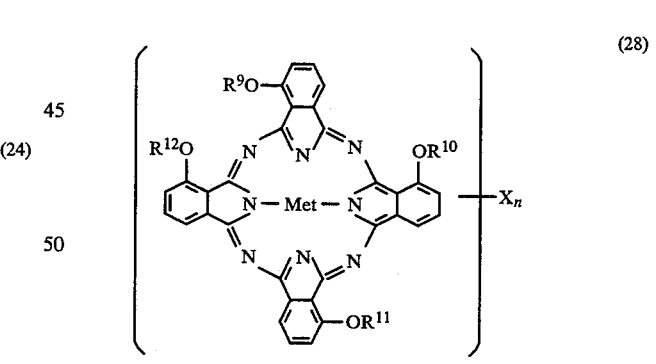 (28)

wherein $R^9$ to $R^{12}$, Met, X and n have the same meanings as in the formula (20), or a mixture of these compounds.

3. The method for preparing a halogenated phthalocyanine compound according to claim 2 wherein at least one of $R^9$ to $R^{12}$ is a branched alkyl group.

4. The method for preparing a halogenated phthalocyanine compound according to claim 3 wherein $R^9$ to $R^{12}$ are secondary alkyl groups.

5. The method for preparing a halogenated phthalocyanine compound according to claim 1 wherein X is bromine; n is $1 \leq n \leq 4$; and Met is Pd, Cu, Ni, Co or VO.

6. The method for preparing a halogenated phthalocyanine compound according to claim 1 wherein said halogenating agent is bromine.

7. The method for preparing a halogenated phthalocyanine compound according to claim 1 wherein said organic solvent forms two layers with water.

8. The method for preparing a halogenated phthalocyanine compound according to claim 7 wherein said organic solvent is one or more selected from saturated hydrocarbons, ethers and halogenated hydrocarbons.

9. The method for preparing a halogenated phthalocyanine compound according to claim 8 wherein said organic solvent is one or more selected from the group consisting of n-hexane, n-pentane, n-octane, cyclohexane, methylcyclohexane, ethylcyclohexane, tetrahydrofuran, n-butyl ether, n-propyl ether, isopropyl ether, carbon tetrachloride, chloroform, dichloromethane, 1,1,1-trichloroethane, 1,1,2-trichloroethane and 1,1,2,2-tetrachloroethane.

10. The method for preparing a halogenated phthalocyanine compound according to claim 1 wherein the amount of said organic solvent is 2 to 200 times by weight as much as that of said phthalocyanine compound and said mixture.

11. The method for preparing a halogenated phthalocyanine compound according to claim 1 wherein the amount of water is 0.1 to 5 times by weight as much as that of said organic solvent.

12. The method for preparing a halogenated phthalocyanine compound according to claim 1 wherein the amount of said halogenating agent is in a molar ratio of 1-16 to said phthalocyanine compound and said mixture.

13. The method for preparing a halogenated phthalocyanine compound according to claim 10 wherein the amount of said organic solvent is 4 to 10 times by weight as much as that of said phthalocyanine compound and said mixture.

14. The method for preparing a halogenated phthalocyanine compound according to claim 12 wherein the amount of bromine is in a molar ratio of 1-4 to said phthalocyanine compound and said mixture.

* * * * *